US009222080B2

(12) United States Patent
Qasba et al.

(10) Patent No.: US 9,222,080 B2
(45) Date of Patent: Dec. 29, 2015

(54) ALPHA 1-3 N-GALACTOSYLSTRANSFERASE WITH ALTERED DONOR SPECIFICITIES, COMPOSITIONS AND METHODS OF USE

(71) Applicants: Pradman K. Qasba, Bethesda, MD (US); Boopathy Ramakrishnan, Frederick, MD (US); Elizabeth Boeggeman, Bethesda, MD (US); Marta Pasek, Frederick, MD (US)

(72) Inventors: Pradman K. Qasba, Bethesda, MD (US); Boopathy Ramakrishnan, Frederick, MD (US); Elizabeth Boeggeman, Bethesda, MD (US); Marta Pasek, Frederick, MD (US)

(73) Assignee: The United States of America, as represented by the Secretary, Department of Health & Human Services, Rockville, MD (US)

(*) Notice: Subject to any disclaimer, the term of this patent is extended or adjusted under 35 U.S.C. 154(b) by 0 days.

(21) Appl. No.: 13/860,946

(22) Filed: Apr. 11, 2013

(65) Prior Publication Data
US 2013/0243690 A1    Sep. 19, 2013

Related U.S. Application Data

(63) Continuation of application No. 12/674,638, filed as application No. PCT/US2007/018678 on Aug. 22, 2007, now Pat. No. 8,425,901.

(51) Int. Cl.
| | |
|---|---|
| *C12N 9/10* | (2006.01) |
| *C12P 19/26* | (2006.01) |
| *C12P 21/00* | (2006.01) |

(52) U.S. Cl.
CPC ............... *C12N 9/1051* (2013.01); *C12P 19/26* (2013.01); *C12P 21/005* (2013.01)

(58) Field of Classification Search
CPC .................................................. C12N 9/1051
See application file for complete search history.

(56) References Cited

FOREIGN PATENT DOCUMENTS

WO    WO 2005/051429    * 6/2005

OTHER PUBLICATIONS

Henion et al. 1994; Defining the minimal size of catalytically active primate alpha 1, 3 galactosyltransferase: structure-function studies on recombinant truncated enzyme. Glycobiology. 4(2): 193-201.*
Taniguchi et al., "UDP-N-Acetylgalactosamine:globoside Alpha-3-N Acetylgalactosaminyltransferase EC-2.4.1.88 Purification, Characterization, and some Properties", Journal of Biological Chemistry, vol. 257, No. 18, 1982, pp. 10631-10637.
Database UniProt [Online] May 10, 2005, "RecName: Full=Globoside alpha-1, 3-N-acetylgalactosaminyltransfera e 1 ; EC=<A HREF ="http://srs.ebi.ac.us/srsbin/cgi-bin/wgetz?[enzyme=ECNumber:2.4.1.88]+-e">2.4.1.88</A>; AltName: Full=Forssman glycolipid Sunthetase;" XP002491765, retrieved from EBI accession No. UniProt:Q8VI38.
Database EMBL [Online] Jan. 31, 1990, "Bovine alpha 1-3 galactosyltransferase mRNA completed cds." XP002491766 retrieved from EBI accession No. J04989.
Database UniProt [Online] Apr. 1, 1990, "RecName: Full=N-acetyl-lactosaminide alpha-1,3-galactosyltransferase; EC=<A HREF="http://srs.ebi.ac.uk/srsbin/cgi-bin/wgetz?[enzyme-ECNumber:2.4.1.87]+-e">2.4.1.87</A;AltName: Full=UDP-galactose:beta-D-galactosyl-1,4-N-acetyl-D-glucosaminide alpha-1,3-galactosyltransferase; Short=Galactosyltransfer" XP002491767 retrieved from EBI accession No. UniProt:P14769.
Qasba et al., "Mutant Glycosyltransferases Assist in the Development of a Targeted Drug Delivery System and Contrast Agents for MRI." The AAPS Journal 2006, vol. 8, No. 1, 2006, pp. E190-E195, XP002491763.
Hang et al., "Probing Glycosyltransferase Activities with the Staudinger Ligation." Journal of the American Chemical Society, vol. 126, No. 1, Jan. 14, 2004, pp. 6-7, XP002491764.
Qasba et al., "Substrate-induced conformational changes in glycosyltransferases." Trends in Biochemical Sciences, vol. 30, No. 1, Jan. 1, 2005, pp. 53-62, XP004710941.
Boix et al., "Structural Basis of Ordered Binding of Donor and Acceptor Substrates to the Retaining Glycosyltransferase, alpha-1,3-Galactosyltransferase." Journal of Biological Chemistry, vol. 277, No. 31, Aug. 2, 2002 pp. 28310-28318, XP002491823.
The International Search Report for corresponding international application serial No. PCT/US2007/018678, filed Aug. 22, 2007.
The Written Opinion for corresponding international application serial No. PCT/US2007/018678, filed Aug. 22, 2007.

* cited by examiner

*Primary Examiner* — Karen Cochrane Carlson
(74) *Attorney, Agent, or Firm* — Locke Lord LLP; Bryan D. Zerhusen; Gabriel J. McCool

(57) ABSTRACT

The invention generally features compositions and methods based on the structure-based design of alpha 1-3 N-Acetyl-galactosaminyltransferase (alpha 3 GalNAc-T) enzymes from alpha 1-3galactosyltransferase (a3Gal-T) that can transfer 2'-modified galactose from the corresponding UDP-derivatives due to substitutions that broaden the alpha 3Gal-T donor specificity and make the enzyme a3 GalNAc-T.

9 Claims, 5 Drawing Sheets

FIG. 5

Mutations in the donor substrate binding site, hinge region and near DXD motif

| Enzyme | Gal activity | GalNAc activity | Galketo activity |
|---|---|---|---|
| a1,3-Gal-........$^{191}$P........$^{228}$Q.....$^{247}$QA$^{248}$......$^{278}$Y......$^{280}$HAA$^{282}$.........$C^{338}$........$W^{356}$ | 100% | 0% | n/a |
| *Mutations in the sugar donor binding site* | | | |
| a1,3-Gal-T..........$^{191}$P.....$^{228}$Q.....$^{247}$QA$^{248}$......$^{278}$Y........$^{280}$TGG$^{280}$..........$C^{338}$......$W^{356}$ | 18% | 10% | n/a |
| a1,3-Gal-T..........$^{191}$P....$^{228}$Q.....$^{247}$QA$^{248}$......$^{278}$Y........$^{280}$SGG$^{280}$..........$C^{338}$......$W^{356}$ | 1.1% | 11% | n/a |
| *Mutations in the hinge region and the sugar donor binding site* | | | |
| a1,3-Gal-T ..........$^{191}$S.....$^{228}$Q.....$^{247}$QA$^{248}$......$^{278}$Y........$^{280}$SGG$^{280}$..........$C^{338}$......$W^{356}$ | 10% | 14% | n/a |
| a1,3-Gal-T............$^{191}$A.....$^{228}$Q ....$^{247}$QA$^{248}$......$^{278}$Y........$^{280}$SGG$^{280}$..........$C^{338}$......$W^{356}$ | 18% | 26% | efficient transfers |
| *Mutations close to DXD and hinge region and the sugar donor binding site* | | | |
| a1,3-Gal-T ..........$^{191}$P.....$^{228}$M.....$^{247}$QA$^{248}$......$^{278}$Y........$^{280}$SGG$^{280}$..........$C^{338}$......$W^{356}$ | 15% | 50% | efficient transfers |
| a1,3-Gal-T ..........$^{191}$A.....$^{228}$M.....$^{247}$QA$^{248}$......$^{278}$Y........$^{280}$SGG$^{280}$..........$C^{338}$......$W^{356}$ | 17% | 60% | efficient transfers |

ALPHA 1-3 N-GALACTOSYLTRANSFERASE WITH ALTERED DONOR SPECIFICITIES, COMPOSITIONS AND METHODS OF USE

RELATED APPLICATIONS/PATENTS & INCORPORATION BY REFERENCE

This application is a Continuation of U.S. application Ser. No. 12/674,638, filed Feb. 22, 2010 and to be issued as U.S. Pat. No. 8,425,901, which is a U.S. National Phase Application pursuant to 35 U.S.C. §371, of PCT International Application Ser. No. PCT/US2007/018678, filed Aug. 22, 2007, designating the United States and published in English on Feb. 26, 2009 as publication WO 2009/025646 A1. The entire disclosure of the aforementioned patent applications are incorporated herein by this reference.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported [in part] by the Intramural Research Program of the NIH, National Cancer Institute, Center for Cancer Research. This research has been funded in part with Federal funds from the National Cancer Institute, NIH, under contract No. N01-C0-12400. The Government may have certain rights in this invention.

FIELD OF THE INVENTION

The invention relates generally to the structure-based design of alpha 1-3 N-Acetylgalactosaminyltransferase (alpha 3 GalNAc-T) enzymes from alpha 1-3 galactosyltransferase (a3Gal-T). The novel alpha 1-3 GalNAc-transferases described herein can transfer 2'-modified galactose from the corresponding UDP-derivatives due to substitutions that broaden the alpha 3Gal-T donor specificity and make the enzyme a3 GalNAc-T.

BACKGROUND OF THE INVENTION

The present invention relates to the field of glycobiology, and specifically to glycosyltransferases, a superfamily of enzymes that are involved in synthesizing the carbohydrate moieties of glycoproteins, glycolipids and glycosaminoglycans. The present invention provides the structure-based design of novel glycosyltransferases and their biological applications.

Glycans can be classified as linear or branched sugars. The linear sugars are the glycosaminoglycans comprising polymers of sulfated disaccharide repeat units that are O-linked to a core protein, forming a proteoglycan aggregate (Raman et al. 2005). The branched glycans are found as N-linked and O-linked sugars on glycoproteins or on glycolipids (Lowe et al., 2003). These carbohydrate moieties of the linear and branched glycans are synthesized by a super family of enzymes, the glycosyltransferases (GTs), which transfer a sugar moiety from a sugar donor to an acceptor molecule. Although GTs catalyze chemically similar reactions in which a monosaccharide is transferred from an activated derivative, such as a UDP-sugar, to an acceptor, very few GTs bear similarity in primary structure.

Eukaryotic cells express several classes of oligosaccharides attached to proteins or lipids. Animal glycans can be N-linked via beta-GlcNAc to Asn (N-glycans), O-linked via -GalNAc to Ser/Thr (O-glycans), or can connect the carboxyl end of a protein to a phosphatidylinositol unit (GPI-anchors) via a common core glycan structure.

The structural information of glycosyltransferases has revealed that the specificity of the sugar donor in these enzymes is determined by a few residues in the sugar-nucleotide binding pocket of the enzyme, which is conserved among the family members from different species. This conservation has made it possible to reengineer the existing glycosyltransferases with broader sugar donor specificities. Mutation of these residues generates novel glycosyltransferases that can transfer a sugar residue with a chemically reactive functional group to N-acetylglucosamine (GlcNAc), galactose (Gal) and xylose residues of glycoproteins, glycolipids and proteoglycans (glycoconjugates). Thus, there is potential to develop mutant glycosyltransferases to produce glycoconjugates carrying sugar moieties with reactive groups that can be used in the assembly of bio-nanoparticles to develop targeted-drug delivery systems or contrast agents for medical uses.

Accordingly, methods to synthesize N-acetylglucosamine linkages have many applications in research and medicine, including in the development of pharmaceutical agents and improved vaccines that can be used to treat disease.

SUMMARY OF THE INVENTION

As described below, the present invention features the structure-based design of alpha 1-3 N-Acetylgalactosaminyltransferase (alpha 3 GalNAc-T) enzymes from alpha 1-3galactosyltransferase (a3Gal-T). The novel alpha 1-3 GalNAc-transferases described herein can transfer 2'-modified galactose from the corresponding UDP-derivatives due to substitutions that broaden the alpha 3Gal-T donor specificity and make the enzyme a3 GalNAc-T.

In one aspect the invention provides a polypeptide fragment of an alpha 1,3 N-acetylgalactosaminyltransferase (alpha 3GalNaC T) that retains the ability to transfer a sugar with a chemically reactive functional group from a sugar donor to a sugar acceptor.

In one embodiment, the polypeptide fragment comprises a donor substrate-binding site, a hinge region and a DXD motif. In another embodiment the polypeptide fragment comprises one or more substitutions in the donor substrate-binding site. In a further embodiment, the polypeptide fragment comprises one or more substitutions in the hinge region. In still another embodiment, polypeptide fragment comprises one or more substitutions near the DXD motif.

In a related embodiment, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a a methionine (M) at amino acid position 228 of (SEQ ID NO:21).

In another aspect, the invention features a polypeptide fragment of an alpha 1,3 N-acetylgalactosaminyltransferase (alpha3GalNAc-T) that transfers a sugar with a chemically reactive functional group from a sugar donor to a sugar acceptor, wherein the polypeptide fragment comprises and one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20

In one embodiment of the above-mentioned aspects, the sugar acceptor is selected from the group consisting of galactose beta 1,4 GlcNac and galactose beta 1,4 glucose.

In another embodiment of the above-mentioned aspects, the sugar with a chemically reactive functional group is selected from the group consisting of UDP-GalNAc, UDP-galactose, and UDP-galactose analogues.

In one embodiment, the UDP-galactose analogue comprises an azido group, a keto group or a thiol group.

In another embodiment, the azido group, the keto group or the thiol group is substituted at the C2 position of galactose. In a further embodiment, the one or more agents are linked to a sugar moiety of the sugar donor. In one embodiment, the one or more agents is selected from the group consisting of: single chain antibodies, bacterial toxins, growth factors, therapeutic agents, targeting agents, contrast agents, chemical labels, radiolabels, and fluorescent labels.

In another aspect, the invention features a polypeptide fragment of an alpha 1,3 N-Acetylgalactosaminyltransferase (alpha3GalNac-T) that retains that ability to transfer a sugar with a chemically reactive functional group from a sugar donor to a sugar acceptor and catalyzes the formation of an oligosaccharide. In one embodiment, the oligosaccharide is a disaccharide or a trisaccharide. In another embodiment, the trisaccharide is selected from the group consisting of: GalNAc alpha1-3Galbeta 1-4Gal, GalNAc alpha1-3-Galbeta 1-4GlcNAc, 2'-modified-Gal alpha 1-3 Gal beta 1-4Gal or 2'-modified-Galalpha 1-3-Gal beta 1-4GlcNAc. In one embodiment, the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In another aspect, the invention features an isolated nucleic acid molecule comprising a nucleotide sequence which is at least 60% homologous to the nucleotide sequence of SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19 or a complement thereof.

In still another aspect, the invention features an isolated nucleic acid molecule which encodes a polypeptide comprising an amino acid sequence at least about 50% homologous to the amino acid sequence of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In one embodiment, the expression cassette or vector comprises the nucleic acid of the aspects as described herein.

In another aspect, the invention features an expression cassette or vector comprising a nucleic acid segment encoding a polypeptide fragment from an alpha 1,3 N acetylgalactosaminyltransferase (alpha 3Gal NAcT that transfers a sugar with a chemically reactive functional group from a sugar donor to a sugar acceptor.

In one embodiment, the cell comprises the expression cassette or vector as described in the aspects herein.

In another aspect, the invention features a method to of making an oligosaccharide comprising incubating a reaction mixture comprising a polypeptide fragment of an alpha 1,3 N-acetylgalactosaminyltransferase (alpha 3GalNaC T) that retains the ability to transfer a sugar with a chemically reactive functional group with a sugar donor and a sugar acceptor.

In one embodiment, the polypeptide fragment comprises a donor substrate binding site, a hinge region and a DXD motif. In another embodiment, the polypeptide fragment comprises one or more substitutions in the donor substrate binding site. In another embodiment, the polypeptide fragment comprises one or more substitutions in the hinge region. In another embodiment, the polypeptide fragment comprises one or more substitutions near the DXD motif.

In a related embodiment, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a methionine (M) at amino acid position 228 of (SEQ ID NO:21).

In another aspect, the invention features a method of making an oligosaccharide comprising incubating a reaction mixture comprising a polypeptide fragment of an alpha 1,3 N-acetylgalactosaminyltransferase (alpha 3GalNaC T) that retains the ability to transfer a sugar with a chemically reactive functional group with a sugar donor and a sugar acceptor, wherein the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In one embodiment, the sugar acceptor is selected from the group consisting of galactose beta 1,4 GlcNac and galactose beta 1,4 glucose.

In another embodiment, the sugar with a chemically reactive functional group is selected from the group consisting of UDP-GalNAc, UDP-galactose, and UDP-galactose analogues.

In a further embodiment, the UDP-galactose analogue comprises an azido group, a keto group or a thiol group. In another embodiment, the azido group, the keto group or the thiol group is substituted at the C2 position of galactose. In still a further embodiment, one or more agents are linked to a sugar moiety of the sugar donor.

In one embodiment, the one or more agents is selected from the group consisting of: single chain antibodies, bacterial toxins, growth factors, therapeutic agents, targeting agents, contrast agents, chemical labels, radiolabels, and fluorescent labels.

In another embodiment, the oligosaccharide is a disaccharide or a trisaccharide. In a related embodiment, the trisaccharide is selected from the group consisting of: GalNAc alpha1-3Galbeta 1-4Gal, GalNAc alpha1-3-Galbeta 1-4GlcNAc, 2'-modified-Gal alpha 1-3 Gal beta 1-4Gal or 2'-modified-Galalpha 1-3-Gal beta 1-4GlcNAc.

In one embodiment, the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In another aspect, the invention features an oligosaccharide synthesized by the method comprising incubating a reaction mixture comprising a polypeptide fragment of an alpha 1,3 N-acetylgalactosylaminotransferase (alpha 3GalNAc T) that retains the ability to transfer a sugar with a chemically reactive functional group with a sugar donor and a sugar acceptor.

In one embodiment, the polypeptide fragment comprises a donor substrate binding site, a hinge region and a DXD motif. In another embodiment, the polypeptide fragment comprises one or more substitutions in the donor substrate binding site. In one embodiment, the polypeptide fragment comprises one or more substitutions in the hinge region. In one embodiment, the polypeptide fragment comprises one or more substitutions near the DXD motif.

In a related embodiment, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a methionine (M) at amino acid position 228 of (SEQ ID NO:21).

In another aspect, the invention features an oligosaccharide synthesized by the method comprising incubating a reaction mixture comprising a polypeptide fragment of an alpha 1,3 N-Acetylgalactosylaminotransferase (alpha 3GalNaC T) that retains the ability to transfer a sugar with a chemically reactive functional group with a sugar donor and a sugar acceptor, wherein the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In one embodiment, the sugar acceptor is selected from the group consisting of galactose beta 1,4 GlcNAc and galactose beta 1,4 glucose. In another embodiment, the sugar with a chemically reactive functional group is selected from the group consisting of UDP-GalNAc, UDP-galactose, and UDP-galactose analogues.

In another embodiment, the UDP-galactose analogue comprises an azido group, a keto group or a thiol group. In a related embodiment, the azido group, the keto group or the thiol group is substituted at the C2 position of galactose.

In a related embodiment, one or more agents are linked to a sugar moiety of the sugar donor. In another embodiment, the one or more agents is selected from the group consisting of: single chain antibodies, bacterial toxins, growth factors, therapeutic agents, targeting agents, contrast agents, chemical labels, radiolabels, and fluorescent labels.

In one embodiment, the oligosaccharide is a disaccharide or a trisaccharide. In another embodiment, the trisaccharide is selected from the group consisting of: GalNAc alpha1-3Gal-beta 1-4Gal, GalNAc alpha1-3-Galbeta 1-4GlcNAc, 2'-modified-Gal alpha 1-3 Gal beta 1-4Gal or 2'-modified-Galalpha 1-3-Gal beta 1-4GlcNAc.

In another embodiment of the above-mentioned aspects, the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In another aspect, the invention features a composition comprising a polypeptide fragment of an alpha 1,3 N-Acetylgalactosylaminotransferase (alpha 3GalNaC T) that retains the ability to transfer a sugar with a chemically reactive functional group from a sugar donor to a sugar acceptor.

In one embodiment, the polypeptide fragment comprises a donor substrate binding site, a hinge region and a DXD motif. In another embodiment, the polypeptide fragment comprises one or more substitutions in the donor substrate binding site. In another embodiment, the polypeptide fragment comprises one or more substitutions in the hinge region. In another embodiment, the polypeptide fragment comprises one or more substitutions near the DXD motif.

In a related embodiment, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a a methionine (M) at amino acid position 228 of (SEQ ID NO:21).

In another aspect, the invention features a composition comprising a polypeptide fragment of an alpha 1,3 N-Acetylgalactosaminyltransferase (alpha3GalNac-T) that transfers a sugar with a chemically reactive functional group from a sugar donor to a sugar acceptor, wherein the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In one embodiment, the sugar acceptor is selected from the group consisting of galactose beta 1,4 GlcNAc and galactose beta 1,4 glucose. In another embodiment, the sugar with a chemically reactive functional group is selected from the group consisting of UDP-GalNAc, UDP-galactose, and UDP-galactose analogues. In another embodiment, the UDP-galactose analogue comprises an azido group, a keto group or a thiol group. In another embodiment, the keto group or the thiol group is substituted at the C2 position of galactose. In another embodiment, one or more agents are linked to a sugar moiety of the sugar donor. In a related embodiment, the one or more agents is selected from the group consisting of: single chain antibodies, bacterial toxins, growth factors, therapeutic agents, targeting agents, contrast agents, chemical labels, radiolabels, and fluorescent labels.

In another aspect, the invention features a composition comprising a polypeptide fragment of an alpha 1,3 N-Acetylgalactosaminyltransferase (alpha3GalNac-T) that retains that ability to transfer a sugar with a chemically reactive functional group from a sugar donor to a sugar acceptor and catalyzes the formation of an oligosaccharide.

In one embodiment, the oligosaccharide is a disaccharide or a trisaccharide. In another embodiment, the trisaccharide is selected from the group consisting of: GalNAc alpha1-3Galbeta 1-4Gal, GalNAc alpha1-3-Galbeta 1-4GlcNAc, 2'-modified-Gal alpha 1-3 Gal beta 1-4Gal or 2'-modified-Galalpha 1-3-Gal beta 1-4GlcNAc.

In another embodiment, the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In another aspect, the invention features an immunological composition comprising a polypeptide fragment of an alpha 1,3 N-Acetylgalactosylaminotransferase (alpha 3GalNaC T) that retains the ability to transfer a sugar with a chemically reactive functional group from a sugar donor to a sugar acceptor.

In one embodiment, the polypeptide fragment comprises a donor substrate-binding site, a hinge region and a DXD motif. In another embodiment, the polypeptide fragment comprises one or more substitutions in the donor substrate-binding site. In another embodiment, the polypeptide fragment comprises one or more substitutions in the hinge region. In another embodiment, the polypeptide fragment comprises one or more substitutions near the DXD motif.

In a related embodiment, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a methionine (M) at amino acid position 228 of (SEQ ID NO:21).

In another aspect, the invention features an immunological composition comprising a polypeptide fragment of an alpha 1,3 N-Acetylgalactosaminyltransferase (alpha3GalNac-T) that transfers a sugar with a chemically reactive functional group from a sugar donor to a sugar acceptor, wherein the polypeptide fragment comprises and one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20, and wherein one or more antibodies are conjugated to the chemically reactive functional group.

In one embodiment, the sugar acceptor is selected from the group consisting of galactose beta 1,4 GlcNac and galactose beta 1,4 glucose. In another embodiment, the sugar with a chemically reactive functional group is selected from the group consisting of UDP-GalNAc, UDP-galactose, and UDP-galactose analogues. In another embodiment, the UDP-galactose analogue comprises an azido group, a keto group or a thiol group. In another further embodiment, the azido group, the keto group or the thiol group is substituted at the C2 position of galactose.

In another embodiment, one or more agents are linked to a sugar moiety of the sugar donor. In another embodiment, the agent is selected from single chain antibodies, monoclonal antibodies, polyclonal antibodies, and chimeric antibodies.

In another aspect, the invention features an immunological composition comprising a polypeptide fragment of an alpha 1,3 N-Acetylgalactosaminyltransferase (alpha3GalNac-T) that retains that ability to transfer a sugar with a chemically reactive functional group from a sugar donor to a sugar acceptor and catalyzes the formation of an oligosaccharide, and wherein one or more antibodies are conjugated to the chemically reactive functional group.

In one embodiment, the oligosaccharide is a disaccharide or a trisaccharide. In a related embodiment, the trisaccharide is selected from the group consisting of: GalNAc alpha1-3Galbeta 1-4Gal, GalNAc alpha1-3-Galbeta 1-4GlcNAc, 2'-modified-Gal alpha 1-3 Gal beta 1-4Gal or 2'-modified-Galalpha 1-3-Gal beta 1-4GlcNAc. In another embodiment, the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In another aspect the invention features a method of coupling an agent to a carrier protein comprising incubating a reaction mixture comprising A polypeptide fragment of an alpha 1,3 N-Acetylgalactosylaminotransferase (alpha 3GalNaC T) that retains the ability to transfer a sugar with a chemically reactive functional group from a sugar donor to a sugar acceptor, wherein the sugar donor is coupled to an agent and the sugar acceptor is a carrier protein.

In another embodiment the polypeptide fragment comprises a donor substrate binding site, a hinge region and a DXD motif. In another embodiment, the polypeptide fragment comprises one or more substitutions in the donor substrate-binding site. In another embodiment, the polypeptide fragment comprises one or more substitutions in the hinge region. In another embodiment, the polypeptide fragment comprises one or more substitutions near the DXD motif.

In a related embodiment, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a a methionine (M) at amino acid position 228 of (SEQ ID NO:21).

In another embodiment, the sugar acceptor is selected from the group consisting of galactose beta 1,4 GlcNac and galactose beta 1,4 glucose.

In another embodiment, the sugar with a chemically reactive functional group is selected from the group consisting of UDP-GalNAc, UDP-galactose, and UDP-galactose analogues. In a related embodiment, the UDP-galactose analogue comprises an azido group, a keto group or a thiol group. In another related embodiment, the azido group, the keto group or the thiol group is substituted at the C2 position of galactose.

In another embodiment, one or more agents are linked to a sugar moiety of the sugar donor.

In another embodiment, the one or more agents is selected from the group consisting of: single chain antibodies, bacterial toxins, growth factors, therapeutic agents, targeting agents, contrast agents, paramagnetic contrast agents, chemical labels, radiolabels, and fluorescent labels.

In one embodiment, the oligosaccharide is a disaccharide or a trisaccharide. In another embodiment, the trisaccharide is selected from the group consisting of: GalNAc alpha1-3Galbeta 1-4Gal, GalNAc alpha1-3-Galbeta 1-4GlcNAc, 2'-modified-Gal alpha 1-3 Gal beta 1-4Gal or 2'-modified-Galalpha 1-3-Gal beta 1-4GlcNAc.

In another embodiment, the polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

In one embodiment, the carrier protein is ovalbumin.

In another embodiment, the carrier protein is an IgG.

In a related embodiment, the method of any of the above-mentioned aspects is used in imaging.

In another related embodiment, the agent is a paramagnetic imaging agent used in magnetic resonance imaging.

In another aspect, the invention features a method for the diagnosis or treatment of a subject suffering from a disease or disorder comprising administering to the subject an effective amount of an isolated glycoprotein synthesized by the method according to any one the above-mentioned aspects, wherein one or more agents are linked to the sugar donor, and thereby diagnosing or treating a subject suffering from a disease or disorder.

In one embodiment, the disease or disorder is selected from the group consisting of: proliferative diseases, cardiovascular diseases, inflammatory diseases, cancer, diseases of ageing, and metabolic diseases or disorders.

In another embodiment, the agent is selected from the group consisting of: single chain antibodies, bacterial toxins, growth factors, therapeutic agents, contrast agents, targeting agents, chemical labels, radiolabels, and fluorescent labels.

In another aspect, the invention features a method for imaging a target cell or tissue comprising administering to a subject an oligosaccharide synthesized by the method according to any one of the above-mentioned aspects, and wherein one or more imaging agents are linked to the sugar donor, thereby imaging a target cell or tissue.

In still another aspect, the invention features a method for synthesizing a detectable Gal beta 1-4GlcNAc epitope comprising synthesizing an oligosaccharide according to the method of any one of the above-mentioned aspects, wherein the sugar donor comprises a 2' modified Gal residue and wherein or more detection agents are linked to the 2' modified Gal residue and thereby synthesizing a detectable Gal beta 1-4GlcNAc epitope.

In one embodiment, the detectable Gal beta 1-4GlcNAc epitope is administered to a subject.

In another embodiment, the detectable Gal beta 1-4GlcNAc epitope is administered to a subject to diagnose a disease or disorder.

In another embodiment, the disease or disorder selected from the group consisting of: proliferative diseases, cardiovascular diseases, inflammatory diseases, cancer, diseases of ageing, and metabolic diseases or disorders.

In another aspect the invention features a method for inducing an immune response in a subject comprising administering to the subject an immunological composition according to any one of the above-mentioned aspects.

In another aspect, the invention provides a kit comprising packaging material, and an polypeptide fragment from an alpha 1,3 N-Acetylgalactosaminyltransferase (alpha3GalNac-T) according to any one of the above-mentioned aspects.

In one embodiment, the kit comprises a sugar donor.

In another embodiment, the donor is selected from the group consisting of UDP-galactose, UDP-GalNAc or UDP-GalNAc analogue. In a related embodiment, an agent is linked to the sugar donor. In another related embodiment, the agent is selected from the group consisting of: single chain antibodies, bacterial toxins, growth factors, therapeutic agents, contrast agents, targeting agents, chemical labels, a radiolabels, and fluorescent labels.

BRIEF DESCRIPTION OF THE DRAWINGS

FIG. 5 is a table showing the effect of substitutions in the donor substrate binding site, hinge region and near DXD motif on Gal activity, GalNAc activity and GalKeto activity.

DETAILED DESCRIPTION OF THE INVENTION

Figure 1:
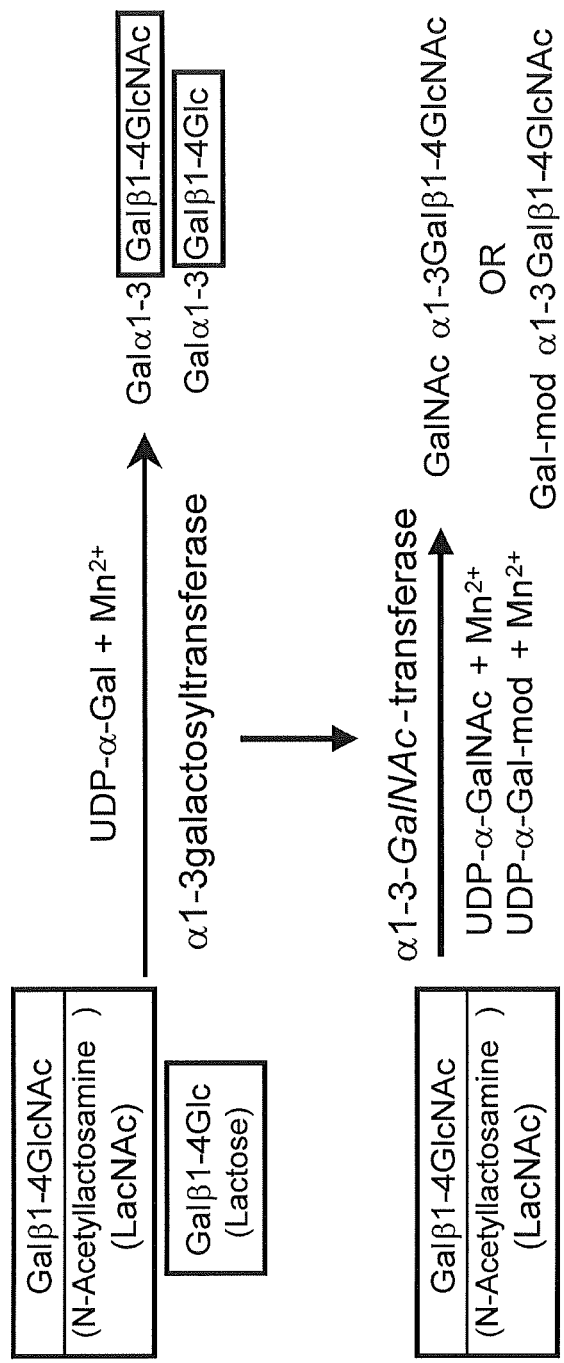
FIG. 1 is a schematic showing the structure—based design of a1-3-N-acetylgalactosaminyltransferase from a1-3-galactosyltransferase.

The invention generally features compositions and methods based on the structure-based design of alpha 1-3 N-acetylgalactosaminyltransferase (alpha 3 GalNAc-T) enzymes from alpha 1-3galactosyltransferase (a3Gal-T) that can transfer 2'-modified galactose from the corresponding UDP-derivatives due to substitutions that broaden the alpha 3Gal-T donor specificity and make the enzyme a3 GalNAc-T.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "acceptor" is meant to refer to a molecule or structure onto which a donor is actively linked through action of a catalytic domain of a galactosyltransferase, or mutant thereof. Examples of acceptors include, but are not limited to, carbohydrates, glycoproteins, glycolipids. The acceptor polypeptide can comprise, in preferred embodiments Galactose residues, free or attached to a peptide or glycopeptide.

The term "agent" or "bioactive agent" is meant to refer to any chemical or biological material or compound that is suitable for delivery that induces a desired effect in or on an organism, such as a biological or pharmacological effect, which may include, but is not limited to a prophylactic effect, alleviating a condition caused by a disease or a disorder, reducing or eliminating a disease or disorder. An agent or a bioactive agent refers to substances that are capable of exerting a biological effect in vitro and/or in vivo. Examples include diagnostic agents, pharmaceuticals, drugs, synthetic organic molecules, proteins, peptides, vitamins, steroids, genetic material including nucleotides, nucleosides, polynucleotides, RNAs, siRNAs, shRNAs, anti-sense DNA or RNA.

The term "antibody" as used herein refers to both polyclonal and monoclonal antibody. The term can also refer to single chain antibodies. The term encompasses not only intact immunoglobulin molecules, but fragments and genetically engineered derivatives of immunoglobulin molecules as may be prepared by techniques known in the art, and which retains the binding specificity of the antigen binding site.

The term "polypeptide fragment" refers to an amino acid segment which folds into a domain that is able to catalyze the linkage of a donor to an acceptor. A polypeptide fragment may be from any mammalian alpha1-3 N-acetylgalactosaminyltransferase (a3 GalNAc-T). In certain embodiments, the polypeptide fragment is from bovine a3 GalNAc-T, in other certain embodiments, the polypeptide fragment is from human a3 GalNAc-T. In preferred embodiments, the a3 GalNAc-T polypeptide fragment is selected from the nucleotide sequence comprising SEQ ID NO: 1, SEQ ID NO:3, SEQ ID NO: 5, SEQ ID NO: 7, SEQ ID NO: 9, SEQ ID NO: 11, SEQ ID NO: 15, SEQ ID NO: 17, and SEQ ID NO: 19. In other embodiments, the a3 GalNAc-T polypeptide fragment is selected from the protein corresponding to the amino acid sequence comprising SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20. The invention relates generally to the structure-based design of alpha 1-3 N-acetylgalactosaminyltransferase (a 3 GalNAc-T) enzymes from alpha 1-3galactosyltransferase (a3Gal-T) . . . . " The polypeptide fragment used for the construction of a3 GalNAc-T enzymes is, in certain examples, from bovine alpha-1,3 galactosyltransferase corresponding to the amino acid sequence NO: 21 as shown herein.

The term "donor" refers to a molecule that is actively linked to an acceptor molecule through the action of a catalytic domain of a galactosyltransferase, or mutant thereof. A donor molecule can include a sugar, or a sugar derivative. Examples of donors include, but are not limited to, UDP-GalNAc, UDP-galactose or UDP-galNAc analogues, UDP-galactose analogues. Donors include sugar derivatives that include agents, biological agents, or active groups. Accordingly, oligosaccharides may be prepared according to the methods of the invention that include a sugar derivative having any desired characteristic.

The term "DXD motif" is meant to refer to a glycosyltransferase sugar-binding region containing DXD motif. In preferred embodiments, the DXD motif is a short conserved motif found in many families of glycosyltransferases, which add a range of different sugars to other sugars, phosphates and proteins. In other certain embodiments, DXD-containing glycosyltransferases all use nucleoside diphosphate sugars as donors and require divalent cations, usually manganese. Preferred DXD motifs are represented by the NCBI conserved domain database designation pfam04488.8.

The term "effective amount" is meant to refer to a sufficient amount that is capable of providing the desired local or systemic effect.

The term "expression cassette" as used herein refers to a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The expression cassette may be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term "alpha1-3 N-acetylgalactosaminyltransferase (a3 GalNAc-T)" as used herein refers to enzymes substantially homologous to, and having substantially the same biological activity as, the enzyme coded for by the nucleotide sequence depicted in any one of SEQ ID NOs: 1, 3, 5, 7, 9, 11, 15, 17, 19 and the amino acid sequence depicted in SEQ ID NOs: 2, 4, 6, 8, 10, 12, 14, 16, 18, 20. This definition is intended to encompass natural allelic variations in the a3 GalNAc-T sequence, and all references to a3 GalNAc-T, and nucleotide and amino acid sequences thereof are intended to encompass such allelic variations, both naturally occurring and man-made. The production of proteins such as the enzyme a3 GalNAc-T from cloned genes by genetic engineering is well known.

The a3 GalNAc-T enzyme may be synthesized in host cells transformed with vectors containing DNA encoding the a3 GalNAc-T enzyme. A vector is a replicable DNA construct. Vectors are used herein either to amplify DNA encoding the a3 GalNAc-T enzyme and/or to express DNA which encodes the a3 GalNAc-T enzyme. An expression vector is a replicable DNA construct in which a DNA sequence encoding the a3 GalNAc-T enzyme is operably linked to suitable control sequences capable of effecting the expression of the a3 GalNAc-T enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

The term "homologous" is intended to include a first amino acid or nucleotide sequence which contains a sufficient or minimum number of identical or equivalent amino acid residues or nucleotides, e.g., an amino acid residue which has a similar side chain, to a second amino acid or nucleotide sequence such that the first and second amino acid or nucleotide sequences share common structural domains and/or a common functional activity.

The terms "oligosaccharide" and "polysaccharide" are used interchangeably herein. These terms refer to saccharide chains having two or more linked sugars. Oligosaccharides and polysaccharides may be homopolymers and heteropolymers having a random sugar sequence or a preselected sugar sequence. Additionally, oligosaccharides and polysaccharides may contain sugars that are normally found in nature, derivatives of sugars, and mixed polymers thereof. "saccharide" refers to any of a series of compounds of carbon, hydrogen, and oxygen in which the atoms of the latter two elements are in the ratio of 2:1, especially those containing the groupC6H1o05, including fructose, glucose, sucrose, lactose, maltose, galactose and arabinose.

The term "immunogenic" compound or composition as used herein refers to a compound or composition that is capable of stimulating production of a specific immunological response when administered to a suitable host, usually a mammal.

The term "nucleic acid" is intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene can be endogenous to the host cell or can be recombinantly introduced into the host cell, e.g., as a plasmid maintained episomally or a plasmid (or fragment thereof) that is stably integrated into the genome. In one embodiment, the gene of polynucleotide segment is involved sugar transfer. A mutant nucleic acid molecule or is intended to include a nucleic acid molecule or gene having a nucleotide sequence which includes at least one alteration (e.g., substitution, insertion, deletion) such that the polypeptide or polypeptide that can be encoded by said mutant exhibits an activity that differs from the polypeptide or polypeptide encoded by the wild-type nucleic acid molecule or gene.

The terms "polypeptides" or "isolated polypeptide" and "proteins" are used interchangeably herein. Polypeptides and proteins can be expressed in vivo through use of prokaryotic or eukaryotic expression systems. Many such expressions systems are known in the art and are commercially available. (Clontech, Palo Alto, Calif.; Stratagene, La Jolla, Calif.).

Examples of such systems include, but are not limited to, the T7-expression system in prokaryotes and the bacculovirus expression system in eukaryotes. Polypeptides can also be synthesized in vitro, e.g., by the solid phase peptide synthetic method or by in vitro transcription/translation systems. Such methods are described, for example, in U.S. Pat. Nos. 5,595,887; 5,116,750; 5,168,049 and 5,053,133; Olson et al., Peptides, 9, 301, 307 (1988). The solid phase peptide synthetic method is an established and widely used method, which is described in the following references: Stewart et al., Solid Phase Peptide Synthesis, W. H. Freeman Co., San Francisco (1969); Merrifield, J. Am. Chem. Soc., 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., Meth. Enzymol., 287, 233 (1997). These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography. The term an "isolated polypeptide" (e.g., an isolated or purified biosynthetic enzyme) is substantially free of cellular material or other contaminating polypeptides from the microorganism from which the polypeptide is derived, or substantially free from chemical precursors or other chemicals when chemically synthesized The polypeptides of the invention include polypeptides having amino acid exchanges, i.e., variant polypeptides, so long as the polypeptide variant is biologically active. The variant polypeptides include the exchange of at least one amino acid residue in the polypeptide for another amino acid residue, including exchanges that utilize the D rather than L form, as well as other well known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, N-methyl-alanine, para-benzoyl-phenylalanine, phenylglycine, propargylglycine, sarcosine, N-acetylserine, N-formylmethionine, 3-methylhistidine, 5-hydroxylysine, and other similar amino acids and imino acids and tert-butylglycine.

Conservative amino acid exchanges are preferred and include, for example; aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid exchange also includes groupings based on side chains. Members in each group can be exchanged with another. For example, a group of amino acids having aliphatic side chains is glycine, alanine, valine, leucine, and isoleucine. These may be exchanged with one another. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant polypeptide of the invention.

The term "subject" as used herein refers to any animal, including mammals, preferably humans, to which the present invention may be applied.

The term "cancer" or "tumor" refers to an aggregate of abnormal cells and/or tissue which may be associated with diseased states that are characterized by uncontrolled cell proliferation. The disease states may involve a variety of cell types, including, for example, endothelial, epithelial and myocardial cells. Included among the disease states are neoplasms, cancer, leukemia and restenosis injuries.

Alpha 1,3 N-Acetylgalactosaminyltransferase (a3 GalNAc-T)

Specific glycosyltransferases synthesize oligosaccharides by the sequential transfer of the monosaccharide moiety of an activated sugar donor to an acceptor molecule. Members of the glycosyltransferase superfamily, which are often named after the sugar moiety that they transfer, are divided into subfamilies on the basis of linkage that is generated between the donor and acceptor. Transfer of the sugar residue occurs with either the retention (by retaining glycosyltransferases) or the inversion (by inverting glycosyltransferases) of the configuration at the anomeric C1 atom. Glycosyltransferases show great structural similarity. They are all globular proteins with two types of fold, termed GT-A and GT-B, which each have an N-terminal and a C-terminal domain. The enzymes of the GT-A fold have two dissimilar domains. The N-terminal domain, which recognizes the sugar-nucleotide donor, comprises several b-strands that are each flanked by a-helices as in a Rossmann-like fold, whereas the C-terminal domain, which contains the acceptor-binding site, consists largely of mixed b-sheets. By contrast, enzymes with the GT-B fold contain two similar Rossmann-like folds, with the N-terminal domain providing the acceptor-binding site and the C-terminal domain providing the donor-binding site.

In both types of enzyme, the two domains are connected by a linker region and the active site is located between the two domains. A metal-binding site is also located in the cleft in enzymes of both the GT-B and GT-A fold (Qasba et al. 2005).

Alpha (1,3)-galactosyltransferase I (a3 Gal-T)

The alpha (1,3)-galactosyltransferase I (a3 Gal-T) enzyme mediates the formation of gal-alpha-gal moieties. A3 Gal-T uses UDP-galactose as a source of galactose, which it transfers to an acceptor oligosaccharide, usually Gal beta (1,4) GlcNAc (N-acetyl lactosamine). As used herein the term "alpha (1,3)galactosyltransferase" and the abbreviation "alpha 1,3GT" refer to the enzyme, present in non-primate mammals, that catalyzes the formation of the Gal.alpha.(1,3)Gal determinant by attaching Gal in the .alpha.(1,3) position to the Gal.beta.(1,4)GlcNAc acceptor.alpha.1,3GT has the Enzyme Commission designation EC 2.4.1.124.

The expression of alpha.1-3 galactosyltransferase is regulated both developmentally and in a tissue-specific manner. The cDNA for this enzyme has been isolated from many species, including pigs (Hoopes et al., poster presentation at the 1997 Xenotransplantation Conference, Nantes France; Katayama et al., J. Glycoconj., 15(6), 583-99 (1998); Sandrin et al., Xenotransplantation, 1, 81-88 (1994), Strahan et al., Immunogenics, 41, 101-05 (1995)), mice (Joziasse et al., J. Biol. Chem., 267, 5534-41 (1992)), and cows (Joziasse et al., J. Biol. Chem., 264, 14290-97 (1989). Some mammals do not express the Gal alpha.(1,3)Gal product, an in these organisms the alpha 1,3GT locus is inactivated (Gailili et al., Proc. Natl. Acad. Sci. USA 15:7401, 1991). There are frameshift and nonsense substitutions within the locus, turning it into a nonfunctional, processed pseudogene (Laarsen et al., J. Biol. Chem. 265:7055, 1990; Joziasse et al., J. Biol. Chem. 266: 6991, 1991). Larsen et al. (Proc. Natl. Acad. Sci. USA 86:8227, 1989) isolated and characterized a cDNA encoding murine alpha.1,3GT. Joziasse et al. (J. Biol. Chem. 267:5534, 1992) detected four distinct mRNA transcripts, which predict four different isoforms of the .alpha.1,3GT. The full-length mouse mRNA (including 5' untranslated mRNA) was reported to span at least 35-kB of genomic DNA, distributed over nine exons ranging from 36 base pairs to about 2600 base pairs in length. Numbering in the 5' to 3' direction, the coding region is distributed over Exons 4 to 9. The four transcripts are formed by alternative splicing of the pre-mRNA. Joziasse et al. (J. Biol. Chem. 264:14290, 1989) isolated and characterized a cDNA encoding bovine cDNA. The coding sequence was predicted to be a membrane-bound protein with a large glycosylated COOH-terminal domain, a transmembrane domain, and a short $NH_2$ terminal domain.

The term Gal alpha (1,3)Gal refers to an oligosaccharide determinant present on endothelial cells and other cells of most non-primate mammals, for which humans have a naturally occurring antibody. Except for Old World monkeys, apes and humans, most mammals carry glycoproteins on their cell surfaces that contain galactose alpha 1,3-galactose (Galili et al., J. Biol. Chem. 263: 17755-17762, 1988). Humans, apes and Old World monkeys have a naturally occurring anti-alpha gal antibody that is produced in high quantity (Cooper et al., Lancet 342:682-683, 1993). It binds specifically to glycoproteins and glycolipids bearing galactose alpha-1,3 galactose. In contrast, glycoproteins that contain galactose alpha 1,3-galactose are found in large amounts on cells of other mammals, such as pigs. This differential distribution of the "alpha-1,3 GT epitope" and anti-Gal antibodies (i.e., antibodies binding to glycoproteins and glycolipids bearing galactose alpha-1,3 galactose) in mammals is the result of an evolutionary process which selected for species with inactivated (i.e. mutated) alpha-1,3-galactosyltransferase in ancestral Old World primates and humans. Thus, humans are "natural knockouts" of alpha-1,3GT. A direct outcome of this event is the rejection of xenografts, such as the rejection of pig organs transplanted into humans initially via HAR.

Alpha 1,3 N-Acetylgalactosaminyltransferase (a3 GalNAc-T)

The present invention features the structure-based design of alpha 1-3 N-Acetylgalactosaminyltransferase (a3 GalNAc-T) from a3Gal-T that can transfer 2'-modified galactose from the corresponding UDP-derivatives. The genetically engineered a3Gal-T to a3GalNAc-T, which can transfer 2'N-acetygalactose (GalNAc) or 2'-modified galactose from the corresponding UDP-derivatives, is very useful for the synthesis of a trisaccharide GalNAccd-3Galβ1-4Glc or GalNAccd-3-Gal β1-4GlcNAc or 2'-modified-Galα1-3Galβ1-4Glc or 2'-modified-Galα1-3-Galβ1-4GlcNAc in an oligosaccharide chain that is otherwise difficult to be synthesized by chemical methods.

The Sugar Binding Pocket

It has been discovered that mutation of alpha 1,3 N-Acetylgalactosaminyltransferase (a3 GalNAc-T) can broaden the donor specificity of the enzyme. More specifically, it has been determined that, in certain embodiments, mutation in residues in the sugar-nucleotide binding pocket of the enzyme can broaden the donor specificity of the enzyme. In particular, substitution of amino acid residues located in the in the sugar-nucleotide binding pocket provide greater flexibility and decreased steric hindrance that allow a broader range of donor (or substrate) binding, for example UDP-GalNAc, UDP-galNAc analogues, UDP-galactose, or UDP-galactose analogues, while still preserving interaction with amino acid residues active during catalytic bond formation between the donor and the acceptor.

A three-residue motif, Asp-X-Asp (DXD) or Glu-X-Asp (EXD), or its equivalent generally participates in metal ion binding in enzymes of the GT-A fold. Enzymes of the GT-B fold such as the microbial glycosyltransferases MurG (Hu, Y. et al. (2003)) and GtfB (Mulichack et al. 2001), and BGT (Morera et al. 1999), do not have a DXD motif or its equivalent, even though some, BGT for example, require a metal ion for activity. In glycosyltransferases that require Mn2C ion as cofactor, the metal ion is bound in an octahedral coordination (Qasba et al. 2005). It interacts with one or both acidic residues of the DXD or EXD motif and with two oxygen atoms from the a-phosphate and b-phosphate of UDP. To satisfy the octahedral geometry, the three remaining metal ion links are made either to water molecules or to water in combination with other residues of the protein. In several glycosyltransferases only the first (Lobsanov, Y. D. et al. (2004)) or the second (Gastinel et al. 1999; Ramakrishnan et al. 2001; Ramakrishnan 2002; Unligil 2000) acidic residue of the motif coordinates directly with the metal ion. For example, in some enzymes, the first acidic residue of the motif either interacts directly with the sugar donor or the ribose moiety or interacts via the water molecules coordinated to the Mn2C ion. In blood group A and B and alpha 3GT transferases, by contrast, both aspartic acid residues of the DXD motif directly coordinate the metal ion.

The crystal structures of several glycosyltransferases of either the GT-A or GT-B fold show that at least one flexible loop region has a crucial role in the catalytic mechanism of the enzyme (Qasba et al. 2005). Although the exact location of this loop differs among the transferases, it is invariably located in the vicinity of the sugarnucleotide-binding site. Owing to the flexibility of this region, the loop structure cannot be traced in the apo form of the enzyme, which lacks bound substrate. In the sugar-nucleotide-bound structures, the loop either is in a closed conformation covering the bound donor substrate or is found disordered in the vicinity of the sugarnucleotide-binding site. In a3GT, the C-terminal 11-residue flexible loop changes its conformation when the sugamucleotide donor is bound (Boix et al., 2001).

Without being bound by any theory, examples of catalytic residues thought to be important for binding include Pro 191, Gln228, His280, Ala28 1, and Ala282 of bovine a3 GalT. Accordingly, the invention provides alpha 1,3 N-Acetylgalactosaminyltransferase (a3 GalNAc-T) enzymess having amino acid substitutions, insertions, and deletions that provide greater flexibility and decreased steric hindrance in the sugar nucleotide binding pocket to allow the mutated alpha 1,3 N-Acetylgalactosaminyltransferase (a3 GalNAc-T) to catalyze chemical bonding of the donor to an acceptor, such as N-acetylglucosamine (GlcNAc), galactose (Gal) and xylose residues of glycoproteins, glycolipids or proteoglycan (glycoconjugates).

Polypeptide Fragments

The invention features, in certain embodiments, polypeptide fragments from alpha 1,3 N-Acetylgalactosaminyltransferases (alpha3GalNac-T) transfer sugars with a chemically reactive functional group from a sugar donor to a sugar acceptor. The a3 GalNAc transferases described herein comprise substitutions in a3 Gal-T, in certain preferred examples, bovein a 3GalT. The substitutions have the effect of broadening the donor specificity of the transferase and make the enzyme an alpha 3 GalNAc-T.

In certain examples, the invention provides a polypeptide fragment of an alpha 1,3 N-Acetylgalactosylaminotransferase (alpha 3GalNaC T) that retains the ability to transfer a sugar with a chemically reactive functional group from a sugar donor to a sugar acceptor. The polypeptide fragments, in certain preferred examples, comprise a donor substrate-binding site, a hinge region and a DXD motif. Thr polypeptide fragment can comprise one or more substitutions in the donor substrate-binding site.

A number of substitutions of the polypeptide fragments are envisioned by the instant invention. The substitutions have the effect of broadening the donor specificity of the enzyme. In certain examples, the polypeptide fragment comprises one or more substitutions in the hinge region. In other examples, polypeptide fragment comprise one or more substitutions near the DXD motif.

the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a a methionine (M) at amino acid position 228 of (SEQ ID NO:21).

In another example, the invention features a polypeptide fragment of an alpha 1,3 N-Acetylgalactosaminyltransferase (alpha3GalNac-T) that transfers a sugar with a chemically reactive functional group from a sugar donor to a sugar acceptor, wherein the polypeptide fragment comprises and one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20. The sequences are set forth below.

In certain preferred embodiments, the one or more substitutions comprise an amino acid exchange at position 191. SEQ ID NO: 1 and SEQ ID NO: 2 correspond to the nucleotide and amino acid sequences, respectively, encoding the P191A bovine alpha3GalT.

```
                                             SEQ ID NO: 1
  1  ATGGCTAGCA TGACTGGNGN NCAGCAAATG GGTCGCGGAT
     CCCACCACCA

51  CCACCACCAC GAAAGCAAGC TTAAGCTATC GGACTGGTTC
     AACCCATTTA

101  AACGCCCCGA GGTTGTGACC ATGACGAAGT GGAAGGCTCC
     AGTGGTGTGG
```

```
151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGGCTGAGA

401 AGAGGTGGCA GGATATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC CATGCAGCCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCC ACTAAAATCT TATCCCCGGA ATACTGCTGG
    GATTATCACA

851 TAGGCCTACC TTCGGATATT AAGCTCGTCA AGATGTCTTG
    GCAGACAAAA

901 GAGTATAATG TGGTTAGAAA TAATGTC
```

```
                                              SEQ ID NO: 2
1   MASMTGXQQM GRGSHHHHHH ESKLKLSDWF NPFKRPEVVT
    MTKWKAPVVW

51  EGTYNRAVLD NYYAKQKITV GLTVFAVGRY IEHYLEEFLT
    SANKHFMVGH

101 PVIFYIMVDD VSRMPLIELG PLRSFKVFKI KAEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFYY HAAIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV
```

In certain preferred embodiments, the one or more substitutions comprise an amino acid exchange at position 280, 281 or 282. SEQ ID NO: 3 and SEQ ID NO: 4 correspond to the nucleotide and amino acid sequences, respectively, encoding the H280L A281G A282G bovine alpha3GalT.

```
                                              SEQ ID NO: 3
1 ATGGCTAGCA TGACTGGTGG NCAGCAAATG GGTCGCGGAT
  CCCACCACCA
```

```
51  CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGCCTGAGA

401 AGAGGTGGCA GGACATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC CTAGGAGGCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCC ACTAAAATCT TATCCCCGGA ATACTGCTGG
    GATTATCACA

851 TAGGCCTACC TTCGGATATT AAGCTCGTCA AGATGTCTTG
    GCAGACAAAA

901 GAGTATAATG TGGTTAGAAA TAATGTC
```

```
                                              SEQ ID NO: 4
1   MASMTGGQQM GRGSHHHHHH ESKLKLSDWF NPFKRPEVVT
    MTKWKAPVVW

51  EGTYNRAVLD NYYAKQKITV GLTVFAVGRY IEHYLEEFLT
    SANKHFMVGH

101 PVIFYIMVDD VSRMPLIELG PLRSFKVFKI KPEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFYY LGGIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV
```

In certain preferred embodiments, the one or more substitutions comprise an amino acid exchange at position 228, 280, 281, or 282. SEQ ID NO: 5 and SEQ ID NO: 6 correspond to the nucleotide and amino acid sequences, respectively, encoding the Q228M H280S A281G A282G bovine alpha3GalT.

```
                                                SEQ ID NO: 5
  1 ATGGCTAGCA TGACTGGTGG NCAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGGCTGAGA

401 AGAGGTGGCA GGATATCAGC ATGATGCGCA TGAAGACTAT
    CGGGGAGCAC

451 ATTGTGGCCC ACATCCAGCA TGAGGTTGAC TTCCTTTTCT
    GCATGGACGT

501 CGACATGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC TCCGGAGGCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCT ACTAAAATCT TATCCCCGGA ATACTGCTGG
    GATTATCACA

851 TAGGCCTACC TTCGGATATT AAGCTTGTCA AGATGTCTTG
    GCAGACAAAA

901 GAGTATAATG TGGTTAGAAA TAATGTC

SEQ ID NO: 6
  1 MASMTGGQQM GRGSHHHHHH ESKLKLSDWF NPFKRPEVVT
    MTKWKAPVVW

51 EGTYNRAVLD NYYAKQKITV GLTVFAVGRY IEHYLEEFLT
    SANKHFMVGH

101 PVIFYIMVDD VSRMPLIELG PLRSFKVFKI KAEKRWQDIS
    MMRMKTIGEH

151 IVAHIQHEVD FLFCMDVDMV FQDKFGVETL GESVAQLQAW
    WYKADPNDFT

201 YERRKESAAY IPFGEGDFYY SGGIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV
```

In certain preferred embodiments, the one or more substitutions comprise an amino acid exchange at position 280 or 282. SEQ ID NO: 7 and SEQ ID NO: 8 correspond to the nucleotide and amino acid sequences, respectively, encoding the H280S A282G bovine alpha3GalT.

```
                                                SEQ ID NO: 7
  1 ATGGCTAGCA TGACTGGTGG ACAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTGGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGCCTGAGA

401 AGAGGTGGCA GGACATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC TCCGCCGGCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCT ACTAAAATCT TATCCCCGGA ATACTGCTGG
    GATTATCACA

851 TAGGCCTACC TTCGGATATT AAGCTTGTCA AGATGTCTTG
    GCAGACAAAA

901 GAGTATAATG TGGTTAGAAA TAATGTCTGA

SEQ ID NO: 8
  1 MASMTGGQQM GRGSHHHHHH ESKLKLSDWF NPFKRPEVVT
    MTKWKAPVVW

51 EGTYNRAVLD NYYAKQKITV GLTVFAVGRY IEHYLEEFLT
    SANKHFMVGH

101 PVIFYIMVDD VSRMPLIELG PLRSFKVFKI KPEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFYY SAGIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV*
```

In certain preferred embodiments, the one or more substitutions comprise an amino acid exchange at position 191, 280, 281, or 282. SEQ ID NO: 9 and SEQ ID NO: 10 correspond to the nucleotide and amino acid sequences, respectively, encoding the P191S H280S A281G A282G bovine alpha3GalT.

```
                                         SEQ ID NO: 9
  1 ATGGCTAGCA TGACTGGTGG ACAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGTCTGAGA

401 AGAGGTGGCA GGATATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC TCCGGAGGCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCC ACTAAAATCT TATCCCCGGA ATACTGCTGG
    GATTATCACA

851 TAGGCCTACC TTCGGATATT AAGCTCGTCA AGATGTCTTG
    GCAGACAAAA

901 GAGTATAATG TGGTTAGAAA TAATGTC

SEQ ID NO: 10
  1 MASMTGGQQM GRGSHHHHHH ESKLKLSDWF NPFKRPEVVT
    MTKWKAPVVW

51 EGTYNRAVLD NYYAKQKITV GLTVFAVGRY IEHYLEEFLT
    SANKHFMVGH

101 PVIFYIMVDD VSRMPLIELG PLRSFKVFKI KSEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFYY SGGIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV
```

In certain preferred embodiments, the one or more substitutions comprise an amino acid exchange at position 191, 280, 281, or 282. SEQ ID NO: 11 and SEQ ID NO: 12 correspond to the nucleotide and amino acid sequences, respectively, encoding the P191A H280S A281G A282G bovine alpha3GalT.

```
                                         SEQ ID NO: 11
  1 ATGGCTAGCA TGACTGGTGG ACAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGGCTGAGA

401 AGAGGTGGCA GGATATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC TCCGGAGGCA TTTTTGGGGG AACACCCACT
    CANNTCCTTA

701 ACATCACCCA NGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCC ACTAAAATCT TATCCCCGGA ATACTGCTGG
    GATTATCACA

851 TAGGCCTACC TTCGGATATT AAGCTCGTCA AGATGTCTTG
    GCAGACAAAA

901 GAGTATAATG TGGTTAGAAA TAATGT

SEQ ID NO: 12
  1 MASMTGGQQM GRGSHHHHHH ESKLKLSDWF NPFKRPEVVT
    MTKWKAPVVW

51 EGTYNRAVLD NYYAKQKITV GLTVFAVGRY IEHYLEEFLT
    SANKHFMVGH
```

```
101 PVIFYIMVDD VSRMPLIELG PLRSFKVFKI KAEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFYY SGGIFGGTPT XXLNITXECF
    KGILKDKKND

251 IEAQWHDESH LNKYFLLNKP TKILSPEYCW DYHIGLPSDI
    KLVKMSWQTK

301 EYNVVRNN
```

In certain preferred embodiments, the one or more substitutions comprise an amino acid exchange at position 278, 280, 281, or 282. SEQ ID NO: 13 and SEQ ID NO: 14 correspond to the nucleotide and amino acid sequences, respectively, encoding the Y278L H280S A281G A282G bovine alpha3GalT.

```
                                          SEQ ID NO: 13
  1 ATGGCTAGCA TGACTGGTGG ACAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGCCTGAGA

401 AGAGGTGGCA GGACATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTCTTTAC TCCGGAGGCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCC ACTAAAATCT TATCCCCGGA ATACTGCTGG
    GATTATCACA

851 TAGGCCTACC TTCGGATATT AAGCTCGTCA AGATGTCTTG
    GCAGACAAAA

901 GAGTATAATG TGGTTAGAAA TAATGTCTGA
```

```
                                          SEQ ID NO: 14
  1 MASMTGGQQM GRGSHHHHHH ESKLKLSDWF NPFKRPEVVT
    MTKWKAPVVW

51 EGTYNRAVLD NYYAKQKITV GLTVFAVGRY IEHYLEEFLT
    SANKHFMVGH

101 PVIFYIMVDD VSRMPLIELG PLRSFKVFKI KPEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFLY SGGIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV*
```

In certain preferred embodiments, the one or more substitutions comprise an amino acid exchange at position 191. SEQ ID NO: 15 and SEQ ID NO: 16 correspond to the nucleotide and amino acid sequences, respectively, encoding the P191S bovine alpha3GalT.

```
                                          SEQ ID NO: 15
  1 ATGGCTAGCA TGACTGGTGG ACAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGTCTGAGA

401 AGAGGTGGCA GGATATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC CATGCAGCCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT
```

```
801 CAACAAACCC ACTAAAATCT TATCCCCGGA ATACTGCTGG
    GATTATCACA

851 TAGGCCTACC TTCGGATATT AAGCTCGTCA AGATGTCTTG
    GCAGACAAAA

901 GAGTATAATG TGGTTAGAAA TAATGTC
```

SEQ ID NO: 16
```
MASMTGGQQM GRGSHHHHHH ESKLKLSDWF NPFKRPEVVT
MTKWKAPVVW

EGTYNRAVLD NYYAKQKITV GLTVFAVGRY IEHYLEEFLT
SANKHFMVGH PVIFYIMVDD VSRMPLIELG PLRSFKVFKI
KSEKRWQDIS MMRMKTIGEH IVAHIQHEVD FLFCMDVDQV
FQDKFGVETL GESVAQLQAW WYKADPNDFT
YERRKESAAY IPFGEGDFYY HAAIFGGTPT QVLNITQECF
KGILKDKKND IEAQWHDESH LNKYFLLNKP TKILSPEYCW
DYHIGLPSDI KLVKMSWQTK EYNVVRNNV
```

In certain preferred embodiments, the one or more substitutions are amino acid exchange at position 280, 281 or 282. SEQ ID NO: 17 and SEQ ID NO: 18 correspond to the nucleotide and amino acid sequences, respectively, encoding the H280S A281G A282G bovine alpha3GalT.

SEQ ID NO: 17
```
  1 ATGGCTAGCA TGACTGGTGG NCAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGCCTGAGA

401 AGAGGTGGCA GGACATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC

601 TACGAGAGGC GGAAGGAGTC TGCAGCATAC ATTCCCTTCG
    GCGAAGGGGA

651 TTTTTATTAC TCCGGAGGCA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCC ACTAAAATCT TATCCCCGGA ATACTGCTGG
    GATTATCACA

851 TAGGCCTACC TTCGGATATT AAGCTCGTCA AGATGTCTTG
    GCAGACAAAA

901 GAGTATAATG TGGTTAGAAA TAATGTC
```

SEQ ID NO: 18
```
  1 MASMTGGQQM GRGSHHHHHH ESKLKLSDWF NPFKRPEVVT
    MTKWKAPVVW

51 EGTYNRAVLD NYYAKQKITV GLTVFAVGRY IEHYLEEFLT
    SANKHFMVGH

101 PVIFYIMVDD VSRMPLIELG PLRSFKVFKI KPEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFYY SGGIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV
```

In certain preferred embodiments, the one or more substitutions comprise an amino acid exchange at position 280, 281 or 282. SEQ ID NO: 19 and SEQ ID NO: 20 correspond to the nucleotide and amino acid sequences, respectively, encoding the H280T A281G A282G bovine alpha3GalT.

SEQ ID NO: 19
```
  1 ATGGCTAGCA TGACTGGTGG ACAGCAAATG GGTCGCGGAT
    CCCACCACCA

51 CCACCACCAC GAAAGCAAGC TTAAGCTATC GGACTGGTTC
    AACCCATTTA

101 AACGCCCCGA GGTTGTGACC ATGACGAAGT GGAAGGCTCC
    AGTGGTGTGG

151 GAAGGCACTT ACAACAGAGC CGTCTTAGAC AATTATTATG
    CCAAGCAGAA

201 AATTACCGTC GGCCTGACGG TTTTCGCCGT CGGAAGATAC
    ATTGAGCATT

251 ACTTGGAGGA GTTCTTAACG TCTGCTAATA AGCACTTCAT
    GGTTGGCCAC

301 CCAGTCATCT TTTATATCAT GGTAGATGAT GTCTCCAGGA
    TGCCTTTGAT

351 AGAGTTGGGT CCTCTGCGCT CCTTCAAAGT GTTTAAGATC
    AAGCCTGAGA

401 AGAGGTGGCA GGACATCAGC ATGATGCGCA TGAAGACTAT
    CGGGGAGCAC

451 ATTGTGGCCC ACATCCAGCA TGAGGTTGAC TTCCTTTTCT
    GCATGGATGT

501 GGACCAGGTC TTCCAAGACA AGTTTGGGGT GGAGACCCTG
    GGCGAGTCGG

551 TGGCCCAGCT ACAAGCCTGG TGGTACAAGG CAGATCCCAA
    TGACTTCACC
```

-continued

```
601 TACGAGAGGC GGAAGGAGTC TGCAGCATAC ATTCCCTTCG
    GCGAAGGGGA

651 TTTTTATTAC ACAGGAGGTA TTTTTGGGGG AACACCCACT
    CAGGTCCTTA

701 ACATCACCCA GGAATGCTTC AAAGGAATCC TCAAGGACAA
    GAAAAATGAC

751 ATAGAAGCCC AATGGCATGA TGAAAGCCAT CTAAACAAGT
    ATTTCCTTCT

801 CAACAAACCT ACTAAAATCT TATCCCCGGA ATACTGCTGG
    GATTATCACA

851 TAGGCCTACC TTCGGATATT AAGCTTGTCA AGATGTCTTG
    GCAGACAAAA

901 GAGTATAATG TGGTTAGAAA TAATGTC
```

```
                                           SEQ ID NO: 20
  1 MASMTGGQQM GRGSHHHHHH ESKLKLSDWF NPFKRPEVVT
    MTKWKAPVVW

51 EGTYNRAVLD NYYAKQKITV GLTVFAVGRY IEHYLEEFLT
    SANKHFMVGH

101 PVIFYIMVDD VSRMPLIELG PLRSFKVFKI KPEKRWQDIS
    MMRMKTIGEH

151 IVAHIQHEVD FLFCMDVDQV FQDKFGVETL GESVAQLQAW
    WYKADPNDFT

201 YERRKESAAY IPFGEGDFYY TGGIFGGTPT QVLNITQECF
    KGILKDKKND

251 IEAQWHDESH LNKYFLLNKP TKILSPEYCW DYHIGLPSDI
    KLVKMSWQTK

301 EYNVVRNNV
```

In certain preferred embodiments, SEQ ID NO: 21 corresponds to the amino acid sequence encoding the full length bovine alpha3GalT.

```
                                           SEQ ID NO: 21
  1 MNVKGKVILS MLVVSTVIVV FWEYIHSPEG SLFWINPSRN
    PEVGGSSIQK GWWLPRWFNN

61 GYHEEDGDIN EEKEQRNEDE SKLKLSDWFN PFKRPEVVTM
    TKWKAPVVWE GTYNRAVLDN

121 YYAKQKITVG LTVFAVGRYI EHYLEEFLTS ANKHFMVGHP
    VIFYIMVDDV SRMPLIELGP

181 LRSFKVFKIK PEKRWQDISM MRMKTIGEHI VAHIQHEVDF
    LFCMDVDQVF QDKFGVETLG

241 ESVAQLQAWW YKADPNDFTY ERRKESAAYI PFGEGDFYYH
    AAIFGGTPTQ VLNITQECFK

301 GILKDKKNDI EAQWHDESHL NKYFLLNKPT KILSPEYCWD
    YHIGLPSDIK LVKMSWQTKE

361 YNVVRNNV
```

An isolated gene includes a gene which is essentially free of sequences which naturally flank the gene in the chromosomal DNA of the organism from which the gene is derived (i.e., is free of adjacent coding sequences which encode a second or distinct polypeptide or RNA molecule, adjacent structural sequences or the like) and optionally includes 5' and 3' regulatory sequences, for example promoter sequences and/or terminator sequences.

The invention features, in certain embodiments, isolated nucleic acid molecules. The isolated nucleic acid molecules may, in certain examples, comprise a nucleotide sequence which is at least 60%, 70%, 80%, 90%, 95%, 96%, 97%, 98%, 99% or more homologous to the nucleotide sequence of SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19 or a complement thereof.

A nucleic acid molecule of the present invention (e.g., a nucleic acid molecule having the nucleotide sequence of SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19 or a complement thereof) can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989) or can be isolated by the polymerase chain reaction using synthetic oligonucleotide primers designed based upon the sequence of SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19 or a complement thereof. A nucleic acid of the invention can be amplified using cDNA, mRNA or alternatively, genomic DNA, as a template and appropriate oligonucleotide primers according to standard PCR amplification techniques. An isolated nucleic acid molecule of the invention can, in certain examples, comprise a nucleic acid molecule which is a complement of the nucleotide sequence shown in SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19.

In certain embodiments, the isolated nucleic acid molecule can encode a polypeptide that comprises an amino acid sequence that is at least about 50%, 60%, 70%, 80%, 90%, 95%, 96%, 97%, 98%, 99% or more homologous to the amino acid sequence of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

Nucleic Acids and Vectors

As described herein, the present invention provides isolated nucleic acid segments that encode polypeptide fragments of alpha1-3 N-Acetylgalactosaminyltransferase (alpha 3 GalNAc-T). In certain embodiments, for example, the substitutions are in bovine a3Gal-T.

In certain examples, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a methionine (M) at amino acid position 228 of (SEQ ID NO: 21).

Nucleic acid sequences encoding alpha 3 GalNAc-T enzymes, for example SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19, as well as other alpha GalNAc-T from other organisms are available. These nucleic acid sequences can be modified to encode the polypeptide fragments and amino acid segments of the invention through use of well-known techniques (Sambrook et al., Molecular Cloning: A Laboratory Manual, 3rd edition, Cold Spring Harbor Press, Cold Spring Harbor, N.Y. (2001)). For example, a portion of the nucleic acid sequence encoding alpha 1,3 GalNAc-T, for example SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19, can be inserted into an expression vector such that an amino acid segment corresponding to the polypeptide fragment of any of the alpha GalNAc-T enzymes that transfers a sugar with a chemically reactive functional group from a sugar donor to a sugar acceptor (for example, but not limited to, SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19) is expressed upon transformation of a cell with the expression vector. The nucleic acid segments of the invention may be optimized for expression in select cells. Codon optimization tables are available. Harlow and Lane, Antibodies: A Laboratory Manual, Cold Spring Harbor Laboratory Press, 1988.

The nucleic acid segments can be inserted into numerous types of vectors. A vector may include, but is not limited to, any plasmid, phagemid, F-factor, virus, cosmid, or phage in double or single stranded linear or circular form, which may or may not be self-transmissible or mobilizable. The vector can also transform a prokaryotic or eukaryotic host either by integration into the cellular genome or exist extrachromosomally (e.g. autonomous replicating plasmid with an origin of replication).

Preferably the nucleic acid segment in the vector is under the control of, and operably linked to, an appropriate promoter or other regulatory elements for transcription in vitro or in a host cell such as a eukaryotic cell or microbe, e.g. bacteria. The vector may be a bi-functional expression vector which functions in multiple hosts. In the case of genomic DNA, this may contain its own promoter or other regulatory elements and in the case of cDNA this may be under the control of a promoter or other regulatory sequences for expression in a host cell.

Specifically included are shuttle vectors by which is meant a DNA vehicle capable, naturally or by design, of replication in two different host organisms, which may be selected from bacteria and eukaryotic cells (e.g. mammalian, yeast or fungal).

The vector may also be a cloning vector which typically contains one or a small number of restriction endonuclease recognition sites at which nucleic acid segments can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance, hygromycin resistance or ampicillin resistance. Many cloning vectors are commercially available (Stratagene, New England Biolabs, Clonetech).

The nucleic acid segments of the invention may also be inserted into an expression vector. Typically an expression vector contains (1) prokaryotic DNA elements coding for a bacterial replication origin and an antibiotic resistance gene to provide for the amplification and selection of the expression vector in a bacterial host; (2) regulatory elements that control initiation of transcription such as a promoter; and (3) DNA elements that control the processing of transcripts such as introns, transcription termination/polyadenylation sequence.

Methods to introduce a nucleic acid segment into a vector are well known in the art (Sambrook et al., 1989). Briefly, a vector into which the nucleic acid segment is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid segment into the vector. The nucleic acid segment that is to be inserted into the vector is treated with one or more restriction enzymes to create a linearized segment having a blunt end, a "sticky" end with a 5' or a 3' overhang, or any combination of the above. The nucleic acid segment may also be treated with a restriction enzyme and subsequently treated with another DNA modifying enzyme. Such DNA modifying enzymes include, but are not limited to, polymerase, exonuclease, phosphatase or a kinase, to create a polynucleic acid segment that has characteristics useful for ligation of a nucleic acid segment into the vector.

The treated vector and nucleic acid segment are then ligated together to form a construct containing a nucleic acid segment according to methods known in the art (Sambrook, 2002). Briefly, the treated nucleic acid fragment and the treated vector are combined in the presence of a suitable buffer and ligase. The mixture is then incubated under appropriate conditions to allow the ligase to ligate the nucleic acid fragment into the vector. It is preferred that the nucleic acid fragment and the vector each have complimentary "sticky" ends to increase ligation efficiency, as opposed to blunt-end ligation. It is more preferred that the vector and nucleic acid fragment are each treated with two different restriction enzymes to produce two different complimentary "sticky" ends. This allows for directional ligation of the nucleic acid fragment into the vector, increases ligation efficiency and avoids ligation of the ends of the vector to reform the vector without the inserted nucleic acid fragment.

Suitable prokaryotic vectors include but are not limited to pBR322, pMB9, pUC, lambda bacteriophage, m13 bacteriophage, and Bluescript® Suitable eukaryotic vectors include but are not limited to PMSG, pAV009/A+, PMT010/A+, pMAM neo-5, bacculovirus, pDSVE, YIPS, YRP17, YEP. It will be clear to one of ordinary skill in the art which vector or promoter system should be used depending on which cell type is used for a host cell.

The invention also provides expression cassettes which contain a control sequence capable of directing expression of a particular nucleic acid segment of the invention either in vitro or in a host cell. The expression cassette is an isolatable unit such that the expression cassette may be in linear form and functional in in vitro transcription and translation assays. The materials and procedures to conduct these assays are commercially available from Promega Corp. (Madison, Wis.). For example, an in vitro transcript may be produced by placing a nucleic acid segment under the control of a T7 promoter and then using T7 RNA polymerase to produce an in vitro transcript. This transcript may then be translated in vitro through use of a rabbit reticulocyte lysate. Alternatively, the expression cassette can be incorporated into a vector allowing for replication and amplification of the expression cassette within a host cell or also in vitro transcription and translation of a nucleic acid segment.

Such an expression cassette may contain one or a plurality of restriction sites allowing for placement of the nucleic acid segment under the regulation of a regulatory sequence. The expression cassette can also contain a termination signal operably linked to the nucleic acid segment as well as regulatory sequences required for proper translation of the nucleic acid segment. Expression of the nucleic acid segment in the expression cassette may be under the control of a constitutive promoter or an inducible promoter, which initiates transcription only when the host cell is exposed to some particular external stimulus.

The expression cassette may include in the 5'-3' direction of transcription, a transcriptional and translational initiation region, a nucleic acid segment and a transcriptional and translational termination region functional in vivo and/or in vitro. The termination region may be native with the transcriptional initiation region, may be native with the nucleic acid segment, or may be derived from another source. Numerous termination regions are known in the art. Guerineau et al., Mol. Gen. Genet., 262:141 (1991); Proudfoot, Cell, 64:671 (1991); Sanfacon et al., Genes Dev., 5:141 (1991); Munroe et al., Gene, 91:151 (1990); Ballas et al., Nucleic Acids Res., 17:7891 (1989); Joshi et al., Nucleic Acid Res., 15:9627 (1987).

The regulatory sequence can be a nucleic acid sequence located upstream (5' non-coding sequences), within, or downstream (3' non-coding sequences) of a coding sequence, and which influences the transcription, RNA processing or stability, or translation of the associated coding sequence. Regulatory sequences can include, but are not limited to, enhancers, promoter and repressor binding sites, translation leader sequences, introns, and polyadenylation signal sequences. They may include natural and synthetic sequences as well as sequences that may be a combination of synthetic and natural sequences. While regulatory sequences are not limited to promoters, some useful regulatory sequences include constitutive promoters, inducible promoters, regulated promoters, tissue-specific promoters, viral promoters and synthetic promoters.

A promoter is a nucleotide sequence that controls expression of the coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be inducible. Several inducible promoters have been reported (Current Opinion in Biotechnology, 7:168 (1996)). Examples include the tetracycline repressor system, Lac repressor system, copper-inducible systems, salicylate-inducible systems (such as the PR1a system). Also included are the benzene sulphonamide—(U.S. Pat. No. 5,364,780, incorporated by reference herein) and alcohol—(WO 97/06269 and WO 97/06268, both incorporated by reference herein) inducible systems and glutathione S-transferase promoters. In the case of a multicellular organism, the promoter can also be specific to a particular tissue or organ or stage of development.

An enhancer is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects.

The expression cassette can contain a 5' non-coding sequence which is a nucleotide sequence located 5' (upstream) to the coding sequence. It is present in the fully processed mRNA upstream of the initiation codon and may affect processing of the primary transcript to mRNA, stability of the mRNA, or translation efficiency (Turner et al., Molecular Biotechnology, 3:225 (1995)).

The expression cassette may also contain a 3' non-coding sequence, which is a nucleotide sequence, located 3' (downstream) to a coding sequence and includes polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The invention also provides a construct containing a vector and an expression cassette. The vector may be selected from, but not limited to, any vector previously described. Into this vector may be inserted an expression cassette through methods known in the art and previously described (Sambrook et al., 1989). In one embodiment, the regulatory sequences of the expression cassette may be derived from a source other than the vector into which the expression cassette is inserted. In another embodiment, a construct containing a vector and an expression cassette is formed upon insertion of a nucleic acid segment of the invention into a vector that itself contains regulatory sequences. Thus, an expression cassette is formed upon insertion of the nucleic acid segment into the vector. Vectors containing regulatory sequences are available commercially and methods for their use are known in the art (Clonetech, Promega, Stratagene).

The expression cassette, or a vector construct containing the expression cassette may be inserted into a cell. The expression cassette or vector construct may be carried episomal or integrated into the genome of the cell.

A variety of techniques are available and known to those skilled in the art for introduction of constructs into a cellular host. Transformation of bacteria and many eukaryotic cells may be accomplished through use of polyethylene glycol, calcium chloride, viral infection, phage infection, electroporation and other methods known in the art. Other transformation methods are available to those skilled in the art, such as direct uptake of foreign DNA constructs (see EP 295959, incorporated by reference herein), techniques of electroporation or high velocity ballistic bombardment with metal particles coated with the nucleic acid constructs (U.S. Pat. No. 4,945,050, incorporated by reference herein).

The selection of an appropriate expression vector will depend upon the method of introducing the expression vector into host cells. Typically an expression vector contains (1) prokaryotic DNA elements coding for a bacterial origin of replication and an antibiotic resistance gene to provide for the amplification and selection of the expression vector in a bacterial host; (2) DNA elements that control initiation of transcription, such as a promoter; (3) DNA elements that control the processing of transcripts, such as introns, transcription termination/polyadenylation sequence; and (4) a reporter gene that is operatively linked to the DNA elements to control transcription initiation. Useful reporter genes include .beta.-galactosidase, chloramphenicol acetyl transferase, luciferase, green fluorescent protein (GFP) and the like.

Methods of Making and Folding

Galactosyltransferase enzymes of the invention may be produced in soluble form. Methods that may be used to produce such soluble enzymes have been described (U.S. Pat. No. 5,032,519, incorporated by reference in its entirety herein). Briefly, a hydrophobic transmembrane anchor region of a galactosyltransferase is removed to produce an enzyme that is in soluble form.

Accordingly, the invention features methods of making an oligosaccharide comprising incubating a reaction mixture comprising a polypeptide fragment of an alpha 1,3 N-Acetylgalactosylaminotransferase (alpha 3GalNaC T) that retains the ability to transfer a sugar with a chemically reactive functional group with a sugar donor and a sugar acceptor. In certain examples, the polypeptide fragment can comprise any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18, or SEQ ID NO: 20.

Alternatively, alpha 1,3 GalNAcT enzymes of the invention may be produced such that they are anchored in the membrane of a cell. Such enzymes may be produced that are anchored in the membranes of prokaryotic and eukaryotic cells. Methods to produce such enzymes have been described (U.S. Pat. No. 6,284,493, incorporated by reference in its entirety herein).

Briefly, in the case of procaryotes, the signal and transmembrane sequences of the transferase, for example the alpha 1,3 GalNAcT enzyme of the invention, are replaced by a bacterial signal sequence, capable of effecting localization of the fusion protein to the outer membrane. Suitable signal sequences include, but are not limited to those from the major E. coli lipoprotein Lpp and lam B. In addition, membrane spanning regions from Omp A, Omp C, Omp F or Pho E can be used in a tripartite fusion protein to direct proper insertion of the fusion protein into the outer membrane. Any procaryotic cells can be used in accordance with the present invention including but not limited to E. coli, Bacillus sp., and Pseudomonas sp. as representative examples.

It is also possible, in certain embodiments, that the native transmembrane domain of the glycosyltransferase, for example the engineered GalNAcT of the invention as described herein, is replaced by the transmembrane domain of a bacterial outer membrane protein. In this embodiment, the alpha 1,3 GalNAcT signal sequence and the bacterial transmembrane region act in concert to anchor the galactosyltransferase to the bacterial outer cell membrane. Nearly any outer membrane bound protein is suitable for this use including but not limited to Omp A, Omp C, and Omp F, Lpp, and Lam B. The catalytic portion of the GalNAcT should be fused to an extracellular loop in the bacterial transmembrane region in order to insure proper orientation of the fusion protein on the outer membrane surface and not in the cytoplasm or periplasm of the cell. Insertion of a protein into such a loop region has been previously reported (Charbit et al., J. Bacteriology, 173:262 (1991); Francisco et al., Proc. Natl. Acad. Sci., 89:2713 (1992)).

The present invention is also applicable for use with eukaryotic cells resulting in cell surface expression of glycosyltransferases in known culturable eucaryotic cells including but not limited to yeast cells, insect cells, chinese hamster ovary cells (CHO cells), mouse L cells, mouse A9 cells, baby hamster kidney cells, C127 cells, COS cells, Sf9 cells, and PC8 cells.

In another embodiment of the present invention, the transmembrane domain of the alpha 1,3 GalNAcT can be replaced by the transmembrane domain of a plasma membrane protein. The transmembrane domain of any resident plasma membrane protein will be appropriate for this purpose. The transmembrane portions of the M6 P/IGF-II receptor, LDL receptor or the transferrin receptor are representative examples.

In another embodiment the Golgi retention signal of the alpha 1,3 GalNAcT is disrupted by site-directed mutagenesis. This approach mutates the amino acids responsible for localizing the galactosyltransferase to the Golgi compartment. The resultant glycosyltransferase is transported to the plasma membrane where it becomes anchored via its modified transmembrane sequences.

In vitro folding of alpha 1,3 GalNAcT requires proper disulfide bond formation. Ways to ensure proper disulfide bond formation include S-sulfonation of the protein prior to disulfide formation, use of oxido-shuffling reagents, and mutation of free Cys residue to Thr. In the in vitro folding of alpha 3GalNAc-T, the stem region acts as a chaperone. Additionally, there are additives that can be used to prevent the hydrophobic collapse, including polyethylene glycol (PEG, e.g. PEG-4000) or L-arginine-HCl. PEG-4000 and L-arginine are thought to beneficially affect the solubility of folding intermediates of both catalytic domain-proteins (CD-proteins) and stem region/catalytic domain proteins (SRCD-proteins) during in vitro folding or protein obtained from inclusion bodies. In the case of catalytic domain (CD)-proteins, the majority of misfolded proteins are insoluble in the absence of PEG-4000 and L-arginine and so they precipitate out during dialysis. Thus, the process will leave behind the properly folded molecules in solution bound to UDP-agarose that are enzymatically active.

When the catalytic domain of alpha 3GalNAc-T is expressed in E. Coli, it forms insoluble inclusion bodies. These inclusion bodies can be collected and then solubilized and folded in vitro to produce catalytically active domains. General methods for isolating and folding inclusion bodies containing galactosyltransferase catalytic domains have been previously described (Ramakrishnan et al., J. Biol. Chem., 276:37665 (2001)). Thus, the in vitro folding efficiency is directly related to the quantity of active enzyme that is produced from the isolated inclusion bodies. Accordingly, methods to increase the in vitro folding efficiency would provide increased production of catalytic domains that can be used to create useful products. US Application 20060084162, incorporated by reference in its entirety herein, provides materials and methods that improve in vitro folding of catalytic domains from galactosyltransferases that are related to the use of a stem region of alpha 3GalNAc-T. Such methods are of use in the instant invention.

Methods of the Invention

The methods as described herein provide the ability to conjugate multiple agents to compounds or compositions of the invention. An embodiment of the present invention provides a glycoconjugate in which one or more bioactive agents are bound to a modified saccharide residue, e.g., a modified galactose, which is in turn bound to a targeting compound, e.g., a compound capable of binding a receptor on a cell membrane. The 2' modified galactose can be used as a handle to deliver therapeutic agents to specific tissue sites. In this manner, many targeting glycoconjugates can be constructed. For example, a gene delivery system for genetic therapy can be produced by binding a nucleotide and a ligand or antibody to the modified sugar. A therapeutic compound for cancer can be produced by binding a chemotherapeutic agent and a ligand or antibody, e.g., an antibody to a cancer antigen, to the modified sugar residue.

The glycoconjugates can be manufactured as designer glycoconjugates, according to therapeutic need. As such, the designer polypeptide itself can be used for the targeting and drug delivery. The glycoconjugates can be manufactured as nanoparticles. In certain examples, a biological substrate, such as a bioactive agent, for example a therapeutic agent, is used to engineer the nanoparticle. In other examples a second, third, fourth or more bioactive polypeptide is used in association with the nanoparticle to engineer multivalent nanoparticles. The bioactive agents do not have to be the same, for example a nanoparticle comprising three bioactive agents may comprise a chemotherapeutic, a tracking agent and a targeted delivery agent, such as an antibody.

Nanoparticles of the invention have use in methods of treating diseases. In other examples, the methods of the invention are used to engineer a glycoprotein from a magnetic resonance agent for use in diagnostic therapies. In these preferred examples, nanoparticles are engineered as described herein, where the nanoparticles are superparamagnetic nanoparticle.

Polypeptide fragments of the invention having altered donor and acceptor specificity can be used to catalyze the linkage of numerous sugars from a donor to numerous acceptor sugars. Linkage of sugar derivatives can also achieved through use of the altered catalytic domains of the invention due to their expanded donor and acceptor specificity.

The presence of modified sugar moieties on a glycoprotein makes it possible to link bioactive molecules via modified glycan chains, thereby assisting in the assembly of bionanoparticles that are useful for developing the targeted drug delivery system and contrast agents for example for use in imaging, e.g. magnetic resonance imaging. The reengineered recombinant glycosyltransferases as described herein also make it possible to remodel the oligosaccharide chains of glycoprotein drugs, and to synthesize oligosaccharides for vaccine development.

Targeted Glycoconjugates

The alpha 1-3 N-Acetylgalactosaminyltransferases (alpha 3 GalNAc-T) as described herein transfer a sugar from a sugar donor to a sugar acceptor. A sugar acceptor can be selected from galactose beta 1,4 glcNac or galactose beta 1,4 glucose. Sugars that can be transferred include UDP-galactose, UDP-galactose analogues, UDP-GalNAc and UDP-GalNAc analogues. This reaction allows galactose to be linked to a sugar acceptor, for example galactose beta 1,4 glcNAc or galactose beta 1,4 glucose, that may itself be linked to a variety of other molecules, such as sugars and proteins, e.g., therapeutic agents, imaging agents, antibodies.

As described herein, modifications in sugar donors are tolerated by the alpha 3GalNAc enzymes. The alpha 3Gal-NAc enzymes of the invention have the ability to use unnatural substrates (altered donor specificity) in sugar transfer reactions due to altered donor specificities. The alpha 3 Gal-NAc-T enzymes have a wider range of donor specificity, e.g. are able to tolerate a wider range of donors, due to substitutions in the sugar-nucleotide binding pocket. For example, in certain embodiments as described herein, substitutions in bovine a3Gal-T that broadens a3Gal-T donor specificity and makes the enzyme a3 GalNAc-T.

In certain examples, the one or more substitutions in the substrate binding site comprise an amino acid substitution at position 280, 281, or 282 corresponding to bovine alpha 1,3 galactosyltransferase (alpha 3 Gal-T) (SEQ ID NO: 21). In another related embodiment, the one or more substitutions in the substrate hinge region comprise an amino acid substitution at position 191 corresponding to bovine alpha 1,3 galactosyltransferase (alpha 3 Gal-T) (SEQ ID NO: 21). In one embodiment, the one or more substitutions close to the DXD motif comprise an amino acid substitution at position 228 corresponding to bovine alpha 1,3 galactosyltransferase (alpha 3 Gal-T) (SEQ ID NO 21). In another embodiment, wherein a serine (S) is substituted for a histidine (H) at amino acid position 280, a glycine (G) is substituted for an alanine (A) at amino acid position 281, or a glycine (G) is substituted for an alanine at amino acid position 282 of (SEQ ID NO 21). In another embodiment, a serine (S) or an alanine (A) is substituted for a proline (P) at amino acid position 191 corresponding to (SEQ ID NO: 21). In still another embodiment, a glutamine (Q) is replaced with a a methionine (M) at amino acid position 228 of (SEQ ID NO:21).

In one embodiment of the invention, the donor sugar is modified so as to include a functional group at the C2 position of the sugar ring, preferably a ketone or an azido or a thiol functionality. In another embodiment, the modified sugar is a galactose which is modified at the C2 position by the addition of ketone functionality.

WO 2005/051429, incorporated by reference in its entirety herein, describes methods used to bind a bioactive agent to the modified sugar. The bioactive compounds may preferably include a functional group which may be useful, for example, in forming covalent bonds with the sugar residue, which are not generally critical for the activity of the bioactive agent. Examples of such functional groups include, for example, amino (—NH:2), hydroxy (—OH), carboxyl (—COOH), thiol (—SH), phosphate, phosphinate, ketone group, sulfate and sulfinate groups. If the bioactive compounds do not contain a useful group, one can be added to the bioactive compound by, for example, chemical synthetic means. Where necessary and/or desired, certain moieties on the components may be protected using blocking groups, as is known in the art, see, e.g., Green & Wuts, Protective Groups in Organic Synthesis (John Wiley & Sons)(1991).

Exemplary covalent bonds by which the bioactive compounds may be associated with the sugar residue include, for example, amide (—CONH—); thioamide (—CSNH—); ether (ROR', where R and R' may be the same or different and are other than hydrogen); ester (—COO—); thioester (—COS—); -0-; —S—; —Sn—, where n is greater than 1, preferably about 2 to about 8; carbamates; —NH—; —NR—, where R is alkyl, for example, alkyl of from about 1 to about 4 carbons; urethane; and substituted imidate; and combinations of two or more of these.

Covalent bonds between a bioactive agent and a modified sugar residue may be achieved through the use of molecules that may act, for example, as spacers to increase the conformational and topographical flexibility of the compound. Examples of such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like.

One of skill in the art can easily chose suitable compatible reactive groups for the bioactive agent and the modified sugar, so as to generate a covalent bond between the bioactive agent and the modified sugar. Also, while the glycoconjugates of the invention are generally described with the targeting agent as the acceptor molecule or structure onto which a donor molecule (e.g., UDP-galactose) is actively linked through the action of a catalytic domain of a galactosyltransferase the bioactive agent can also be an acceptor molecule.

In certain embodiments, the instant method can be used to monitor glycosylation, for example the glycosylation of therapeutic glycoproteins and monoclonal antibodies. The potential of glycosyltransferase enzymes to produce glycoconjugates carrying sugar moieties with reactive groups may be a benefit to the glycotargeting of drugs to their site of action. Although a great number of pharmaceutical agents are discovered each year, the clinical application of these is many times hindered because of failure to reach the site of action. The methods described herein that include using reengineered glycosyltransferases to transfer chemically reactive sugar residues for linking of other molecules via specific glycan chains may be used as an efficient drug delivery system.

Detection

The a3 GalNAc-T as described herein have application in the detection of specific sugar residues on a glycan chain of a glycoconjugates and in the glycoconjugation and assembly of bio-nanoparticles for the targeted delivery of bioactive agents. Protein glycoslation is one of the most abundant post-translational modifications and plays a fundamental role in the control of biological systems and in disease.

Accordingly, glycosylation has been found to be a marker in disease. Additionally, carbohydrate modifications have been shown to be important for host-pathogen interactions, inflammation, development, and malignancy (Varki, 1993; Lasky, 1996).

The methods described herein offer the advantages the modification occurs in a site directed manner, only where the carbohydrate is attached to the glycoprotein. Such specificity permits, for example, the use of site-directed immunotherapy without affecting the antigen binding affinity of the immunoglobulin. Such specificity permits, further, the potential use of this approach in developing a drug delivery system or biological probes.

Imaging

Included in the invention are methods for imaging a target cell or tissue in a subject. The methods as described herein comprise administering to a subject a polypeptide fragment synthesized by the method comprising incubating a reaction mixture comprising a polypeptide fragment from a a3 GalNAc-T with a sugar donor, wherein one or more imaging agents are linked to the sugar donor, and an sugar acceptor thereby imaging a target cell or tissue.

Coupling

Methods of transfer of C2 modified galactose analogues, for example C2 keto galactose from its UDP derivative to the GlcNAc residue on the N-glycan chain of ovalbumin or to an asialo-agalacto-IgG1 molecule have been described in the art, for example in WO 2005/051429, incorporated by reference in its entirety herein. The C2 modified galactose analogues, for example C2 keto galactose can be biotinylated, thus allowing for biotinylation of carriers such as ovalbumin and IgG.

The method of coupling a target agent to a carrier protein via glycan chains, for example ovalbumin and IgG1, is advantageous over other cross-linking methods. In the instant method, the target agent is linked in a site-directed manner, only where the carbohydrate is attached to the glycoprotein, for example as in the IgG1 molecule at the Fc domain, away from the antigen binding site. A problem encountered in previous approaches using monoclonal antibodies for immunotherapy is the lack of specificity of the reactions, resulting in heterologous labeling and a decrease in the antibody affinity for the antigen. The instant invention overcomes this problem.

Accordingly, the invention features methods of coupling an agent or agents to a carrier protein. The methods described herein comprise coupling an agent to a carrier protein comprising incubating a reaction mixture comprising a polypeptide fragment of an alpha 1,3 N-Acetylgalactosylaminotransferase (alpha 3GalNaC T) that retains the ability to transfer a sugar with a chemically reactive functional group from a sugar donor to a sugar acceptor, wherein the sugar donor is coupled to an agent and the sugar acceptor is a carrier protein.

Thr polypeptide fragment can comprise in certain examples SEQ ID NO: 1, SEQ ID NO; 3, SEQ ID NO: 5, SEQ ID NO: 7, SEQ ID NO: 9, SEQ ID NO: 11, SEQ ID NO; 13, SEQ ID NO: 15, SEQ ID NO: 17, SEQ ID NO: 19, with a sugar donor, and a carrier protein, in the presence of manganese.

The sugar donor is, in certain examples, a UDP-galactose analogue, that can comprise an azido group, a keto group, or a thiol group. The azido group, the keto group or the thiol group can be substituted at the C2 position of galactose, thus allowing for linking of agents. Accordingly, in certain preferred examples, one or more agents are linked to a sugar moiety of the sugar donor. The agent can be selected from the group consisting of: antibodies, single chain antibodies, bacterial toxins, growth factors, therapeutic agents, targeting agents, contrast agents, chemical labels, a radiolabels, and fluorescent labels.

The carrier protein, in preferred examples, is ovalbumin. The carrier protein, in other preferred examples, is an IgG. In certain instances, it is advantageous to couple the C2 UDP-galactose analogue to biotin for detection. Subsequent detection of biotin can be carried out by chemiluminescent assay. The method as described herein is useful for imaging procedures, for example in magnetic resonance imaging.

Carbohydrate Synthesis

Enzymatic carbohydrate synthesis using glycosyltransferases is regio- and stereospecific and does not require extensive protecting group designs. Naturally occurring carbohydrates have been successfully prepared by this biomimetic pathway. The novel alpha(1-3)galactosylaminotransferases described herein have use in, for example, the design and synthesis of natural and non-natural carbohydrate libraries for pharmaceutical purposes, for example, the synthesis of sialyl-Lewis(a)- and sialyl-Lewis(x)-libraries. Baisch et al. (Carbohydr Res. 1998 November; 312(1-2): 61-72, incorporated by reference in its entirety herein).

Mimetics of a terminal tetrasaccharide region of many cellular glycoproteins and glycolipids (sialyl Lewis X) have demonstrated to inhibit angiogenesis both in vitro and in vivo and this may be used for cancer treatment Antibodies and Applications As described herein, the targeting compound may be an antibody or a fragment thereof. The term"antibody" (Ab) or"monoclonal antibody" (Mab) is meant to include intact molecules as well as antibody portions (e.g., Fab and F (ab')$_2$ portions and Fv fragments) which are capable of specifically binding to a cell surface marker. Such portions are typically produced by proteolytic cleavage, using enzymes such as papain (to produce Fab portions) or pepsin (to produce F (ab')$_2$ portions). Alternatively, antigen-binding portions can be produced through the application of recombinant DNA technology.

The immunoglobulin can be a "chimeric antibody" as that term is recognized in the art. Also, the immunoglobulin may be a bifunction or a hybrid antibody, that is, an antibody which may have one arm having a specificity for one antigenic site, such as a tumor associated antigen, while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, which is incorporated herein by reference. Hybrid or bifunctional antibodies may be derived biologically, by cell fusion techniques, or chemically, especially with cross-linking agents or disulfide bridge-forming reagents, and may be comprised of those antibodies and/or fragments thereof. Methods for obtaining such hybrid antibodies are disclosed, for example, in PCT application WO83/03679, published Oct. 27, 1983, and published European Application EPA 0 217 577, published Apr. 8, 1987, which are incorporated herein by reference. In one embodiment, the bifunctional antibodies are biologically prepared from a polydome or a quadroma, or are synthetically prepared with cross-linking agents such as bis-(maleimideo)-methyl ether("BMME"), or with other cross-linking agents familiar to those skilled in the art.

In addition, the immunoglobin may be a single chain antibody ("SCA"). These may consist of single chain Fv fragments ("scFv") in which the variable light ("V [L]") and variable heavy ("V [H]") domains are linked by a peptide bridge or by disulfide bonds. Also, the immunoglobulin may consist of single V [H] domains (dAbs) which possess antigen-binding activity. See, e.g., G. Winter and C. Milstein, Nature, 349: 295 (1991); R. Glockshuber et al., Biochemistry, 29: 1362 (1990); and, E. S. Ward et al., Nature, 341: 544 (1989).

The antibodies may, in certain embodiments, be chimeric monoclonal antibodies. As used herein, the term "chimeric antibody" refers to a monoclonal antibody comprising a variable region, i.e., binding region, from one source or species and at least a portion of a constant region derived from a different source or species, usually prepared by recombinant DNA techniques.

Chimeric antibodies comprising a murine variable region and a human constant region are preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies." Methods for producing chimeric antibodies involve conventional recombinant DNA and genetransfection techniques well known in the art. See, e.g., Morrison, S. L. et al., Proc. Nat'l Acad. Sci., 81: 6851 (1984).

Encompassed by the term "chimeric antibody" is the concept of "humanized antibody," that is those antibodies in which the framework or "complementarity" determining regions ("CDR") have been modified to comprise the CDR of an immunoglobulin of different specificity as compared to that of the parent immunoglobulin. (See, e.g., EPA 0 239 400 (published Sep. 30, 1987)) In a preferred embodiment, a murine CDR is grafted into the framework region of a human antibody to prepare the "humanized antibody." See, e.g., L. Riechmann et al., Nature, 332: 323 (1988); M. S, Neuberger et al., Nature, 314: 268 (1985). Furthermore, the immunoglobulin (antibody), or fragment thereof, used in the present invention may be polyclonal or monoclonal in nature. Monoclonal antibodies are the preferred immunoglobulins. The preparation of such polyclonal or monoclonal antibodies is well known to those skilled in the art. See, e.g., G. Kohler and C. Milstein, Nature, 256: 495 (1975). The antibodies of the present invention may be prepared by any of a variety of methods. For example, cells expressing the cell surface marker or an antigenic portion thereof can be administered to an animal in order to induce the production of sera containing polyclonal antibodies. In a preferred method, a preparation of protein is prepared and purified so as to render it substantially free of natural contaminants. Such a preparation is then introduced into an animal in order to produce polyclonal antisera of greater specific activity. However, the present invention should not be construed as limited in scope by any particular method of production of an antibody whether bifunctional, chimeric, bifunctional-chimeric, humanized, or an antigen-recognizing fragment or derivative thereof.

In a preferred embodiment, the antibodies of the present invention are monoclonal antibodies (or portions thereof). Such monoclonal antibodies can be prepared using hybridoma technology (Kohler et al., Nature, 256: 495 (1975); Kohler et al., Eur. J. Immunol., 6: 511 (1976); Kohler et al, Eur. J. Immunol., 6: 292 (1976); Hammerling et al., In: "Monoclonal Antibodies and T-Cell Hybridomas," Elsevier, N.Y., pp. 563-681 (1981)). In general, such procedures involve immunizing an animal (preferably a mouse) with a protein antigen or with a protein-expressing cell (suitable cells can be recognized by their capacity to bind antibody). The splenocytes of such immunized mice are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands et al., Gastroenterology, 80: 225-232 (1981). The hybridoma cells obtained through such a selection are then assayed to identify clones which secrete antibodies capable of binding the antigen. In addition, hybridomas and/or monoclonal antibodies which are produced by such
hybridomas and which are useful in the practice of the present invention are publicly available from sources such as the American Type Culture Collection or commercial retailers.

The antibodies of the present invention may be labeled, for example, for detection or diagnostic purposes, e.g., imaging. Labels for the antibodies of the present invention include, but are not limited to, the following: examples of enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase; examples of radioisotopic labels include 3H, 111In, 125I, 131I, 32p, 35S, 14c, 51Cr, 57To, 58Co, 59Fe, 75Se, 152Eu, 90Y, 67Cu, 217Ci, 211At, 212Pb, 47Sc, and 109Pd; examples of suitable non-radioactive isotopic labels include 157Gd, 55Mn, 52Tr, and 56Fe; examples of fluorescent labels include an 152 Eu label, a fluorescein label, an isothiocyanate label, a rhodamine label, a phycoerythrin label, aphycocyanin label, an allophycocyanin label, an o-phthaldehyde label, and a fluorescamine label; examples of toxin labels include diphtheria toxin, ricin, and cholera toxin; examples of chemiluminescent labels include a luminal label, an isoluminal label, an aromatic acridinium ester label, an imidazole label, an acridinium salt label, an oxalate ester label, a luciferin label, a luciferase label, and an aequorin label; and examples of nuclear magnetic resonance contrasting agents include heavy metal nuclei such as Gd, Mn, and Fe. Typical techniques for binding the above-described labels to antibodies are provided by Kennedy et al., Clin. Chim Acta, 70:1-31 (1976), and Schurs et al., Clin. Chim. Acta, 81: 1-40 (1977), which are incorporated by reference In one embodiment, the glycoconjugates of the invention include monoclonal antibodies, such as those directed against tumor antigens, for use as cancer therapeutics. Generally, monoclonal antibodies have one N-linked bi-antennary oligosaccharide attached at the IgG-Fc region. The terminal sugars of the oligosaccharide moiety come in several glycoforms, for example, some are desialated, degalactosylated, with only terminal N-acetylglucosaminyl residues.

The monoclonal antibodies carrying only terminal N-acetylgucosamine on the bi-antennary oligosaccharide moieties, the Goglycoform, can be generated by de-sialylation and de-galactosylation of the monoclonal antibodies. With the Tyr289Leu-Gal-T1 (Y289LGalT1) enzyme and UDP-a-galactose-C-2-modified, a galactose moiety that has a chemically reactive group attached at the C2 position of galactose, can then be transferred to Go glycoform of the monoclonal antibody. The chemically reactive group can include, for example, a ketone moiety that can serve as a neutral, yet versatile chemical handle to add other agents, such as bioactive agents, to the compound.

Methods of Treatment

The instant invention provides enzymes and methods that can be used to promote the chemical linkage of biologically important molecules that have previously been difficult to link, and thus provides a means to link agents for therapeutic application. Moreover, the instant invention provides a means to carry out the method in a physiological setting.

Accordingly, the invention features methods for the diagnosis or treatment of a subject suffering from a disease or disorder. The methods comprise administering to the subject an effective amount of polypeptide fragment synthesized by the method comprising incubating a reaction mixture comprising an isolated catalytic domain from an alpha 1,3 N-Acetylgalactosaminyltransferase (alpha3GalNac-T) with a sugar donor, wherein one or more agents are linked to the sugar donor, and an sugar acceptor thereby diagnosing or treating the subject.

In certain preferred embodiments, the polypeptide fragment is encoded by a nucleotide sequence that encodes an alpha 1,3 N-Acetylgalactosaminyltransferase (alpha3GalNac-T) that transfers a sugar with a chemically reactive functional group from a sugar donor to a sugar acceptor. In other certain preferred embodiments, the polypeptide fragment is encoded by a nucleotide sequence which is at least 60%, 70%, 80%, 90%, 95%, 96%, 97%, 98%, 99% or more homologous to the nucleotide sequence of SEQ ID NO: 1, SEQ ID NO: 3, SEQ ID NO: 5, SEQ ID NO: 7, SEQ ID NO: 9, SEQ ID NO; 11, SEQ ID NO: 13, SEQ ID NO: 15, SEQ ID NO: 17, or SEQ ID NO: 19 or a complement thereof.

Disease states needing treatment are only limited by current available therapeutics. As described herein, the methods of the invention are useful for engineering of nanoparticles, including multivalent nanoparticles, carrying any number of therapeutic agents. For example, the nanoparticles can be used to treat cancer, inflammatory disease, cardiovascular disease, obesity, ageing, bacterial infection, or any other disease amenable to therapy.

The glycoconjugates compositions of the invention can be used to treat and/or diagnose a variety of diseases and/or disorders. For example, the glycoconjugates compositions of the invention are used for specific, targeted delivery of bioactive agents, including toxic drugs, agents for imaging or diagnostics, (e.g., toxins, radionuclides), to therapeutically-relevant tissues or cells of the body, for example, tumors. In another embodiment of the invention, the glycoconjugates compositions of the invention are used to deliver bioactive agents, including DNA vectors, to cells.

As further examples, the glycoconjugates compositions of the invention are useful for the treatment of a number of diseases and/or disorders including, but not limited to: cancer, both solid tumors as well as blood-borne cancers, such as leukemia; hyperproliferative disorders that can be treated by the compounds of the invention include, but are not limited to, neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

The glycoconjugates of the invention can be used to treat cardiovascular diseases and disorders including, but not limited to, myocardial infarction (heart attack), cerebrovascular diseases (stroke), transient ischaemic attacks (TIA), peripheral vascular diseases, arteriosclerosis, angina, high blood pressure, high cholesterol, arrhythmia.

The glycoconjugates of the invention can be used to treat genetic diseases, such as enzyme deficiency diseases.

The glycoconjugates of the invention can be used to treat hyperproliferative disorders. Examples of such hyperproliferative disorders that can be treated by the glycoconjugates of the invention are as described in Application WO 2005/051429, and are incorporated by reference in its entirety herein.

The glycoconjugates of the present invention are also useful for raising an immune response against infectious agents. Viruses are one example of an infectious agent that can cause disease or symptoms that can be treated by the compounds of the invention. Examples of viruses that can cause disease or symptoms and that can be treated by the glycoconjugates of the invention are as described in Application WO 2005/051429, and are incorporated by reference in its entirety herein.

Similarly, bacterial or fungal agents that can cause disease or symptoms and that can be treated by the glycoconjugates of the invention are as described in Application WO 2005/051429, and are incorporated by reference in its entirety herein.

Additionally, the glycoconjugates of the invention are useful for treating autoimmune diseases. An autoimmune disease is characterized by the attack by the immune system on the tissues of the victim. Autoimmune disease is characterized by the inability of the recocognition of "self" and the tissue of the afflicted subject is treated as a foreign target. The compounds of the present invention are therefore useful for treating autoimmune diseases by desensitizing the immune system to these self antigens by provided a TCR signal to T cells without a costimulatory signal or with an inhibitory signal. Examples of autoimmune diseases which may be treated using the glycoconjugates of the present invention are as described in Application WO 2005/051429, and are incorporated by reference in its entirety herein.

Similarly, allergic reactions and conditions, such as asthma (particularly allergic asthma) or other respiratory problems, may also be treated by glycoconjugates of the invention. Moreover, the glycoconjugates of the invention can be used to treat anaphylaxis, hypersensitivity to an antigenic molecule, or blood group incompatibility.

The glycoconjugates of the invention which can inhibit an immune response are also useful for treating and/or preventing organ rejection or graft versus host disease, atherosclerosis; olitis; regional enteritis; adult respiratory distress syndrome; local manifestations of drug reactions, such as dermatitis, etc.; inflammation-associated or allergic reaction patterns of the skin; atopic dermatitis and infantile eczema; contact dermatitis; psoriasis; lichen planus; allergic enteropathies; allergic rhinitis; bronchial asthma; hypersensitivity or destructive responses to infectious agents; poststreptococcal diseases, e.g. cardiac manifestations of rheumatic fever, and the like.

Vaccines

The invention also provides methods for eliciting an immune response in a mammal such as a human, including administering to a subject an immunological composition comprising a compound or composition as described herein. Therefore, one embodiment of the present invention is to use the glycoconjugates described herein in an immunological preparation.

The immunological composition according to the instant invention may be prepared by any method known in the art. For example, glycoconjugates of the present invention are prepared and are then injected into an appropriate animal. The compositions according to the present invention may be administered in a single dose or they may be administered in multiple doses, spaced over a suitable time scale to fully utilize the secondary immunization response. For example, antibody titers may be maintained by administering boosters once a month. The vaccine may further comprise a pharmaceutically acceptable adjuvant, including, but not limited to Freund's complete adjuvant, Freund's incomplete adjuvant, lipopolysaccharide, monophosphoryl lipid A, muramyl dipeptide, liposomes containing lipid A, alum,muramyl tripeptide-phosphatidylethanoloamine, keyhole and limpet hemocyanin.

Administration

The compositions of the present invention may be administered by any means that results in the contact of the bioactive agent with the agent's site or site (s) of action on or in a subject, e.g., a patient. The compositions may be administered alone or in conjunction with one or more other therapies or treatments.

The targeted glycoconjugates produced according to the present invention, can be administered to a mammalian host by any route. Thus, as appropriate, administration can be orally, intravenously, rectally, parenterally, intracisternally, intradermally, intravaginally, intraperitoneally, topically (as by powders, ointments, gels, creams, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

In addition, administration can be by periodic injections of a bolus of the therapeutic or can be made more continuous by intravenous or intraperitoneal administration from an external source. In certain embodiments, the therapeutics of the instant invention can be pharmaceutical-grade and incompliance with the standards of purity and quality control required for administration to humans. Veterinary applications are also within the intended meaning as used herein.

The formulations, both for veterinary and for human medical use, of the therapeutics according to the present invention typically include such therapeutics in association with a pharmaceutically acceptable carrier therefor and optionally other ingredient (s). The carrier (s) can be acceptable in the sense of being compatible with the other ingredients of the formulations and not deleterious to the recipient thereof. Pharmaceutically acceptable carriers are intended to include any and all solvents, dispersion media, coatings, antibacterial and antifungal agents, isotonic and absorption delaying agents, and the like, compatible with pharmaceutical administration.

A pharmaceutical composition of the invention is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such asethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences. Formulations for parenteral administration also can include glycocholate for buccal administration, methoxysalicylate for rectal administration, or citric acid for vaginal administration. The parenteral preparation can be enclosed in ampoules, disposable syringes or multiple dose vials made of glass or plastic.

Formulations of the present invention suitable for oral administration can be in the form of discrete units such as capsules, gelatin capsules, sachets, tablets, troches, or lozenges, each containing a predetermined amount of the drug; in the form of a powder or granules; in the form of a solution or a suspension in an aqueous liquid or non-aqueous liquid; or in the form of an oil-in-water emulsion or a water-in-oil emulsion. The therapeutic can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier.

For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gumtragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by sterilization, e.g., filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient.

Formulations suitable for topical administration, including eye treatment, include liquid or semi-liquid preparations such as liniments, lotions, gels, applicants, oil-in-water or water-in-oil emulsions such as creams, ointments or pasts; or solutions or suspensions such as drops. Formulations for topical administration to the skin surface can be prepared by dispersing the therapeutic with a dermatologically acceptable carrier such as a lotion, cream, ointment or soap. In some embodiments, useful are carriers capable of forming a film or layer over the skin to localize application and inhibit removal.

For inhalation treatments, such as for asthma, inhalation of powder (self-propelling or spray formulations) dispensed with a spray can, a nebulizer, or an atomizer can be used. Such formulations can be in the form of a finely comminuted powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the therapeutics also can be delivered in the form of an aerosol spray from a pressured container or dispenser which contains a suitable propellant, e.g., a gas such as carbon dioxide, or a nebulizer. Nasal drops also can be used.

Systemic administration also can be by transmucosal ortransdermal means. For transmucosal or transdermal administration, penetrants appropriate to the barrier to be permeated are used in the formulation. Such penetrants generally are known in the art, and include, for example, for transmucosal administration, detergents, bile salts, and filsidic acid derivatives. Transmucosal administration can be accomplished through the use of nasal sprays or suppositories. Fortransdermal administration, the therapeutics typically are formulated into ointments, salves, gels, or creams as generally known in the art.

The therapeutics can be prepared with carriers that will protect against rapid elimination from the body, such as a controlled release formulation, including implants and microencapsulated delivery systems.

The compounds of the invention may also suitably be administered by sustained-release systems. Suitable examples of sustained-release compositions include semipermeable polymer matrices in the form of shaped articles, e.g., films, or mirocapsules. Sustained-release matrices include polylactides (U.S. Pat. No. 3,773,919, EP 58, 481), copolymers of L-glutamic acid and gamma-ethyl-L-glutamate (U. Sidman et al., Biopolymers 22: 547-556 (1983)), poly (2-hydroxyethyl methacrylate) (R. Langer et al., J. Biomed. Mater. Res. 15: 167-277 (1981), and R. Langer, Chem. Tech. 12: 98-105 (1982)), ethylene vinyl acetate (R. Langer et al., Id.) or poly-D-(–)-3-hydroxybutyric acid (EP 133,988). Sustained-release compositions also include liposomally entrapped compositions of the present invention (Epstein, et al., Proc. Natl. Acad. Sci. USA 82: 3688-3692 (1985); Hwang et al., Proc. Natl. Acad. Sci. USA 77: 4030-4034 (1980).

The compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, the therapeutics identified according to the invention can be formulated for administration to humans or other mammals, for example, in therapeutically effective amounts, e.g., amounts which provide appropriate concentrations of the bioactive agent to target tissue/cells for a time sufficient to induce the desired effect. Additionally, the therapeutics of the present invention can be administered alone or in combination with other molecules known to have a beneficial effect on the particular disease or indication of interest. By way of example only, useful cofactors include symptom-alleviating cofactors, including antiseptics, antibiotics, antiviral and antifungal agents and analgesics and anesthetics.

The effective concentration of the therapeutics identified according to the invention that is to be delivered in a therapeutic composition will vary depending upon a number of factors, including the final desired dosage of the drug to be administered and the route of administration. The preferred dosage to be administered also is likely to depend on such variables as the type and degree of the response to be achieved; the specific composition of another agent, if any, employed; the age, body weight, general health, sex and diet of the patient; the time of administration, route of administration, and rate of excretion of the composition; the duration of the treatment; bioactive agent (such as a chemotherapeutic agent) used in combination or coincidental with the specific composition; and like factors well known in the medical arts. In some embodiments, the therapeutics of this invention can be provided to an individual using typical dose units deduced from the earlier-described mammalian studies using non-human primates and rodents. As described above, a dosage unit refers to a unitary, i.e. a single dose which is capable of being administered to a patient, and which can be readily handled and packed, remaining as a physically and biologically stable unit dose comprising either the therapeutic as such or a mixture of it with solid or liquid pharmaceutical diluents or carriers.

Therapeutics of the invention also include "prodrug" derivatives. The term prodrug refers to a pharmacologically inactive (or partially inactive) derivative of a parent molecule that requires biotransformation, either spontaneous or enzymatic, within the organism to release or activate the active component. Prodrugs are variations or derivatives of the therapeutics of the invention which have groups cleavable under metabolic conditions. Prodrugs become the therapeutics of the invention which are pharmaceutically active in vivo, when they undergo solvolysis under physiological conditions or undergo enzymatic degradation. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992).

Therapeutic or Diagnostic Agents

A wide variety of agents may be included in the compounds of the present invention, such as any biologically active, therapeutic or diagnostic compound or composition. In general, the term bioactive agent includes, but is not limited to: polypeptides, including proteins and peptides (e.g., insulin); releasing factors and releasing factor inhibitors, including Luteinizing Hormone Releasing Hormone (LHRH) and gonadotropin releasing hormone (GnRH) inhibitors; carbohydrates (e.g., heparin); nucleic acids; vaccines; and pharmacologically active agents such as anti-infectives such as antibiotics and antiviral agents; anti-fungal agents; analgesics and analgesic combinations; anesthetics; anorexics; anti-helminthics; anti-arthritic agents; respiratory drugs, including anti-asthmatic agents and drugs for preventing reactive airway disease; anticonvulsants; antidepressants; anti-diabetic agents; anti-diarrheals; anticonvulsants; antihistamines; anti-inflammatory agents; toxins, anti-migraine preparations; anti-nauseants; anticancer agents, including anti-neoplastic drugs; anti-parkinsonism drugs; anti-pruritics; anti-psychotics; antipyretics; antispasmodics; anticholinergics; sympathomimetics; xanthine derivatives; cardiovascular preparations including potassium and calcium channel blockers, beta-blockers, alpha-blockers, cardioprotective agents; anti-arrhythmics; anti-hyperlipidemic agents; anti-hypertensives; diuretics; anti-diuretics; receptor agonists, antagonists, and/or mixed function agonist/antagonists; vasodilators including general coronary, peripheral and cerebral; central nervous system stimulants; vasoconstrictors; cough and cold preparations, including decongestants; enzyme inhibitors; hormones such as estradiol, testosterone, progesterone and other steroids and derivatives and analogs, including corticosteroids; hypnotics; hormonolytics; immunosuppressive agents; muscle relaxants; parasympatholytics; central nervous system stimulants; diuretics; hypnotics leukotriene inhibitors; mitotic inhibitors; muscle relaxants; genetic material, including nucleic acid, RNA, DNA, recombinant RNA, recombinant DNA, antisense RNA, antisense DNA, hammerhead RNA, a ribozyme, a hammerheadribozyme, an antigene nucleic acid, a ribo-oligonucleotide, a deoxyribonucleotide, an antisense ribo-oligonucleotide, and/or an antisense deoxyribo-oligonucleotide; psychostimulants; sedatives; anabolic agents; vitamins; herbal remedies; anti-metabolic agents; anxiolytics; attention deficit disorder (ADD) and attention deficit hyperactivity disorder (ADHD) drugs; neuroleptics; and tranquilizers.

Application No. WO 2005/051429, incorporated by reference in its entirety herein, provides a list of exemplary agents that can be conjugated to the compositions of the instant invention.

Kits

Also included in the invention are kits. Preferably, kits comprise a packaging material, and a polypeptide fragment from an alpha 1,3 N-Acetylgalactosaminyltransferase (alpha3GalNac-T) according to any one of the aspects of the invention as described herein. The kits, in certain preferred embodiments, comprise a sugar donor. The donor can be any one of UDP-galactose, UDP-GalNAc, UDP-GalNAc analogues or UDP-Galactose analogues. The kits can also comprise an agent. In preferred examples, the agent is linked to the sugar donor. Exemplary agents are described in this disclosure. Certain agents can be selected from antibodies, single chain antibodies, bacterial toxins, growth factors, therapeutic agents, contrast agents, targeting agents, chemical labels, a radiolabels, and fluorescent labels.

EXAMPLES

It should be appreciated that the invention should not be construed to be limited to the examples that are now described; rather, the invention should be construed to include any and all applications provided herein and all equivalent variations within the skill of the ordinary artisan.

As described in more detail below, the experiments reported herein are based on the structure-based design of a 1,3 N-Acetylgalactosaminyltransferase (a3 GalNac-T) from a 1,3 galactosyltransferase (a3 Gal-T) which was mutated at seven positions to broaden a3Gal-T donor specificity and make it a3GalNac-T.

Example 1

Mutation of a3Gal-T Broadens a3Gal-T Donor Specificity and Makes it a3GalNac-T

X-ray crystal structures of the catalytic domain of many glycosyltransferases have been determined in recent years, and these studies show that the specificity of the sugar donor is determined by residues in the sugar-nucleotide binding pocket of glycosyltransferases. This structural information has made it possible to reengineer the existing glycosyltransferases.

Figure 2:
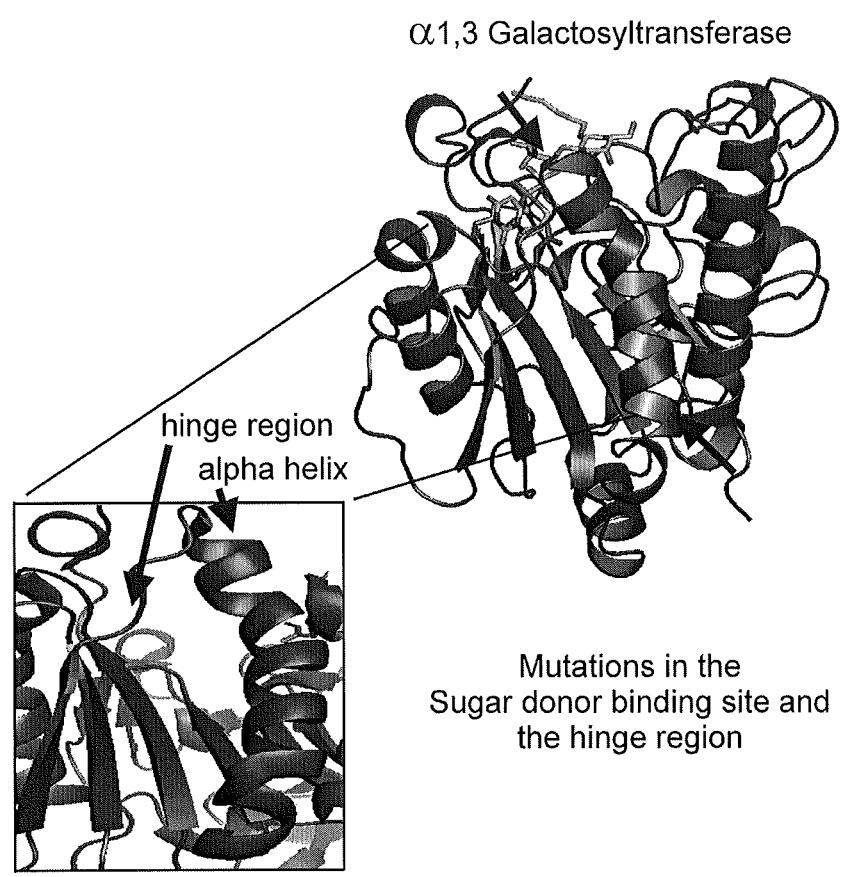
FIG. 2 is a diagram illustrating the structure-based design of a1-3 N-acetylgalactosaminyltransferase (a3GalNAc-T) from a1-3galactosyltransferase (a3Gal-T). The boxed region shows a magnification of the sugar donor binding site and the hinge region where the substitutions occur.

Described herein is the stricture based design of an alpha 1-3-N-acetylgalactosaminyltransferase from a1-3-galactosyltransferase. FIG. 1 is a schematic showing the structure—based design of a1-3-N-acetylgalactosaminyltransferase from a1-3-galactosyltransferase. In FIG. 2, the sugar sugar donor binding site and the hinge region where the substitutions occur are shown. These regions are the regions where the substitutions occur in the a1-3-galactosyltransferase.

Mutation of residues in these regions leads to the novel alpha 1-3 GalNAc-transferases described herein that can transfer 2'-modified galactose.

Figure 3:
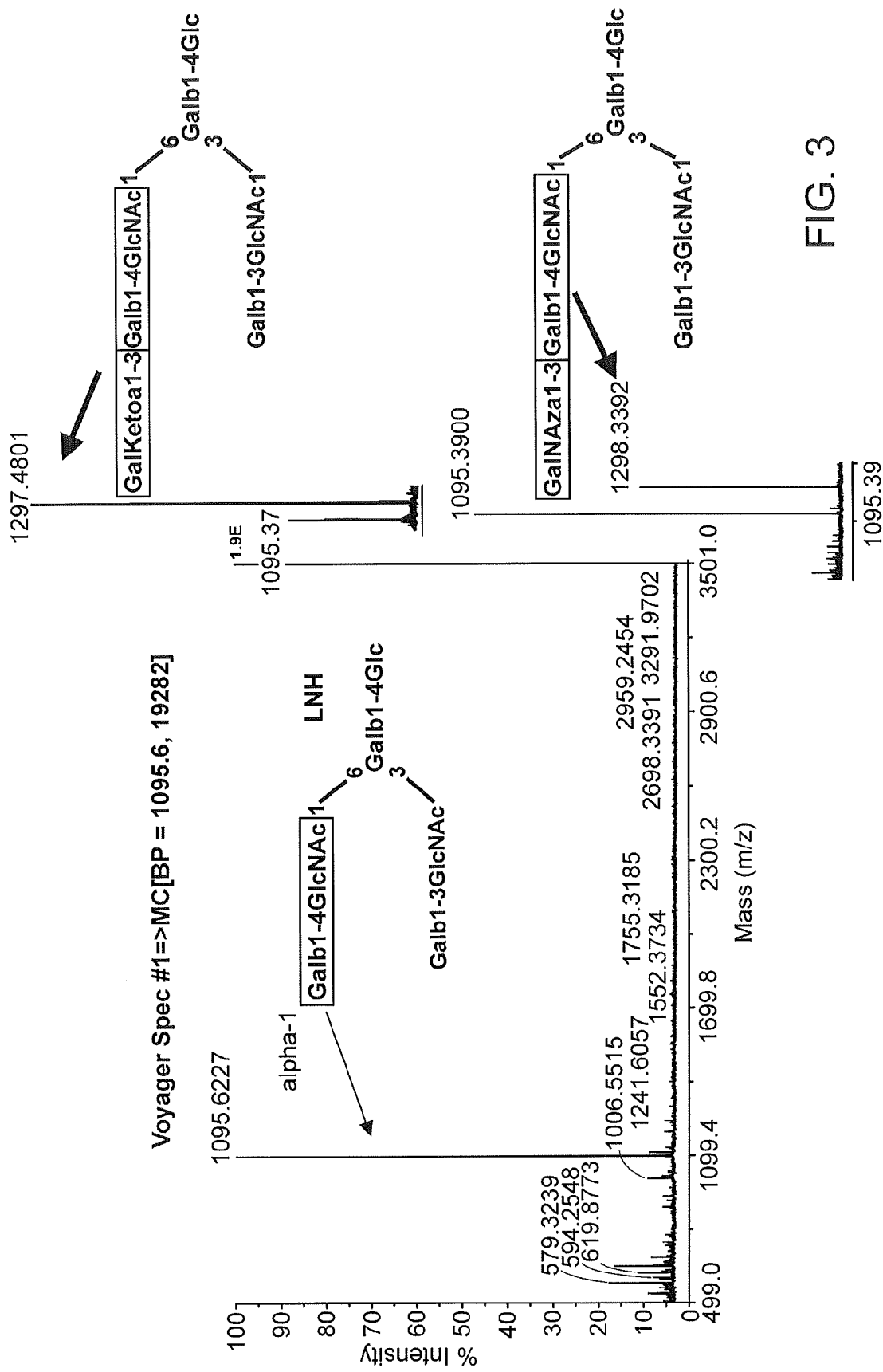
FIG. 3 shows transfer of UDP— modified sugars by the alpha 1,3 Gal-T-191A . . . 280SGG282.
Figure 4:
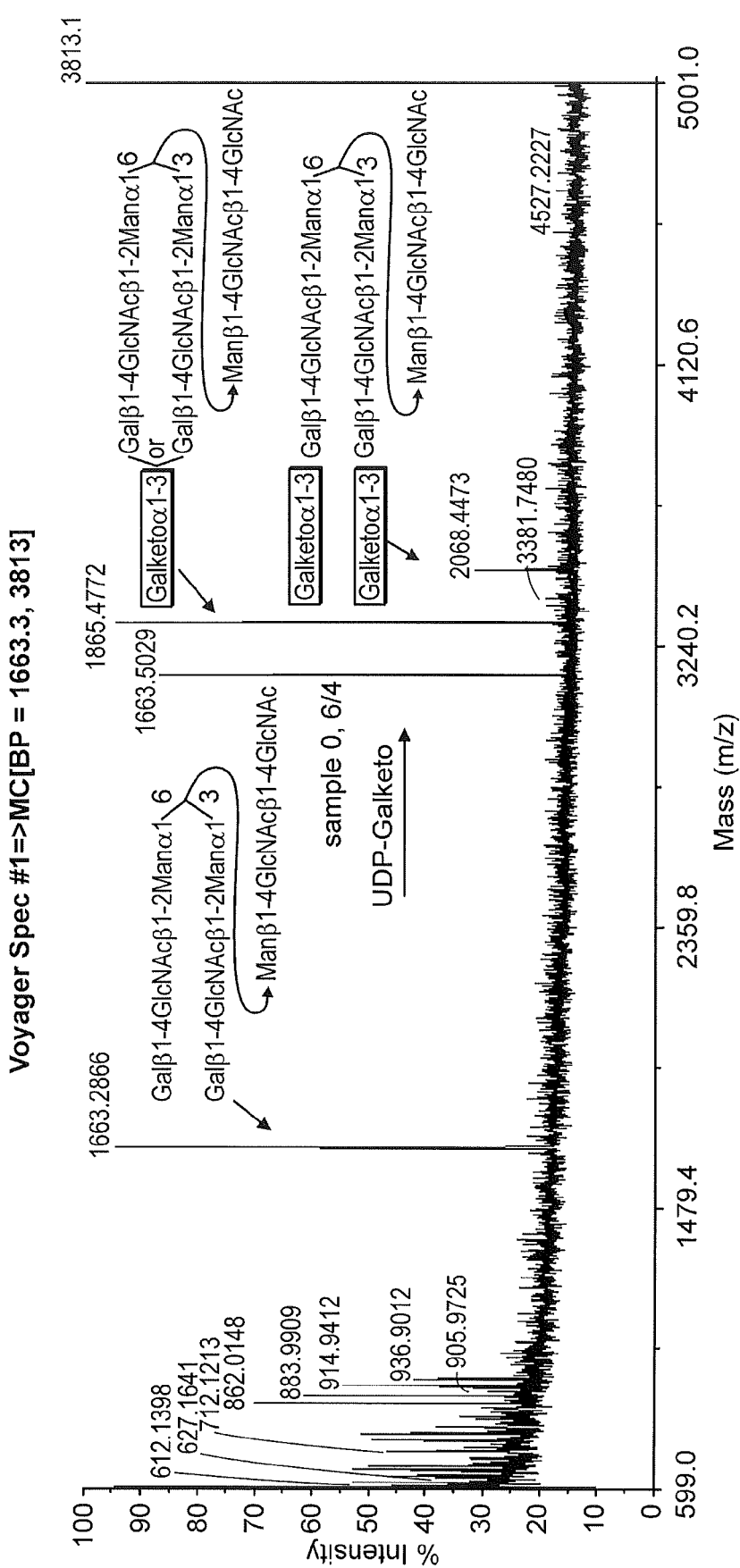
FIG. 4 shows transfer of UDP— modified sugars by the alpha 1,3 Gal-T-191A . . . 280SGG282.

FIG. 3 and FIG. 4 shows transfer of UDP-modified sugars by the alpha 1,3 Gal-T-191A . . . 280SGG282 enzyme. FIG. 5 is a Table showing the effect of substitutions in the donor substrate binding site, hinge region and near DXD motif on Gal activity, GalNAc activity and GalKeto activity is shown.

Methods

The invention was performed using the following methods:
Met344His Mutant

Site-directed mutagenesis was performed using the PCR method. Construction of the enzymes was carried out as described previously in Qasba et al. (Biochemistry 2004, 43, 12513-12522), incorporated by reference in its entirety herein.

Bacterial Growth and Plasmid Transformation

Bacterial growth and plasmid transformations can be performed using standard procedures (Ausubel et al., Current Protocols in Molecular Biology, Greene Publishing Associates and Wiley-Interscience, New York (1987)). US Published Application 20060084162, incorporated by reference in its entirety herein, describes methods for bacterial growth and transformation using the plasmid pEGT-d129, which encodes the catalytic domain (residues 130-402) of bovine .beta.(1,4)-galactosyltransferase I. Site-directed mutagenesis can be performed using a CLONTECH site-directed mutagenesis transformer kit. Thus, the transformation mixture contains the template pEGT-d129, a selection primer, and a mutagenic primer for creation of a desired enzyme. Enzymes are screened for the incorporated substitutions by looking for changes in restriction enzyme digestion patterns and confirmed by DNA sequencing. The positive clones were transformed into B834(DE3)pLysS cells.

Expression and Purification of Inclusion Bodies

The expression and purification of the inclusion bodies can be carried out as described previously (Ausubel et al., Current Protocols in Molecular Biology, Greene Publishing Associates and Wiley-Interscience, New York (1987)). The inclusion bodies are S-sulfonated by dissolving in 5 M GdnHCl, 0.3 M sodium sulfite, and the addition of di-sodium 2-nitro-5-thio-sulfobenzoate to a final concentration of 5 mM. The sulfonated protein is precipitated by dilution with water, and the precipitate was washed thoroughly.

Briefly, 100 mg of sulfonated protein is folded in one liter folding solution for 48 hours. Inclusion of 10% glycerol and 10 mM lactose in the folding solution enhances the folding efficiency of the galactosyltransferase, e.g. beta-1,4-galactosyltransferase (beta4Gal-T1). After refolding the protein, the folding solution is extensively dialyzed against water. During dialysis the misfolded protein precipitates out, while the folded protein remains soluble. The soluble protein is first concentrated and then purified on a Ni-column Nearly 2 mg of folded ppGalNAc-T2 protein is obtained form 1 liter of folding solution. Purified protein may be tested for catalytic activity using a 13 amino acid peptide, PTTDSTTPAPTTK, as an acceptor using methods described previously (Fritz. T. A et al. J Biol. Chem. 2006).

Improving the folding conditions: In recent years factorial folding screens (Rudolph and Lilie, FASEB J., 10:40-56 (1996); Chen and Gouaux, Proc. Natl. Acad. Sci., 94:13431-13436 (1997); Armstrong et al., Prot. Sci., 8:1475-1483 (1999)) have been developed for examining the folding efficiencies of proteins from inclusion bodies. To improve the in vitro folding efficiency, 8 different folding conditions similar to the formulations described in the FoldIt Screen kit (Hampton Research, Calif.) with certain modifications were tested. Condition I: 50 mM Tris-HCl pH 8.0, 5 mM EDTA, 0.5 M guanidine-HCl, 8 mM cysteamine and 4 mM cystamine. Condition II: 55 mM Mes pH 6.5, 10.56 mM NaCl, 0.44 mM KCl, 2.2 mM MgCl.sub.2, 2.2 mM CaCl.sub.2, 0.5 M guanidine-HCl. Condition III: similar to condition II with respect to the buffer, pH, chaotrope and salt condition, but it had 0.055% PEG-4000, 1.1 mM EDTA, 0.44 M sucrose and 0.55 M L-arginine. Condition IV: 55 mM Mes pH 6.5, 264 mM NaCl, 11 mM KCl, 0.055% PEG-4000, 0.5 M guanidine-HCl, 2.2 mM MgCl$_2$, 2.2 mM CaCl.sub.2 and 0.44 M sucrose. Condition V: 55 mM Tris pH 8.2, 10.56 mM NaCl, 0.44 mM KCl, 1.1 mM EDTA, 0.44 M sucrose. Conditions VI and VIII are similar except for the presence of redox agents. Condition VII: 55 mM Mes pH 6.5, 264 mM NaCl, 11 mM KCl, 1.1 mM EDTA, 0.5 M guanidine-HCl, and 0.55 M L-arginine. The buffers II through VII had 100 mM GSH and 10 mM GSSG. Conditions I and VIII, had 8 mM cysteamine and 4 mM cystamine. Condition VIII, gave the highest enzymatic activity, soluble and folded protein, was 50 mM Tris-HCl pH 8.0, 10.56 mM NaCl, 0.44 mM KCl, 2.2 mM MgCl$_2$, 2.2 mM CaCl.sub.2 0.5 M guanidine-HCl, 8 mM cysteamine and 4 mM cystamine, 0.055% PEG-4000 and 0.55 M L-arginine.

Mutation

Mutation of certain amino acid residues as described herein is, in certain examples, performed site-directed mutagenesis. US Published Application 20060084162 describes methods for site directed mutagensis of amino acid position 289 of the bovine .beta.(1,4)-galactosyltransferase I, performed using the PCR method. The method is easily adapted by one of skill in the art to the instant invention for engineering of 1,3 N-Acetylgalactosylaminotransferase (alpha 3GalNaC T) enzymes from the alpha Gal T.

Gal-T and GalNAc-T Enzyme Assays

Gal-T and GalNAc T enzyme assays are easily performed according to methods described in the art, for example US Published Application 20060084162. Protein concentrations are measured using the Bio-Rad protein assay kit, based on the method of Bradford and further verified on SDS gel. An in vitro assay procedure for the Gal-T1 has been reported previously (Ramakrishnan et al., J. Biol. Chem., 270, 87665-376717 (2001)). The activities were measured using UDP-Gal or UDP-GalNAc as sugar nucleotide donors, and GlcNAc and Glc as the acceptor sugars. For the specific activity measurements, a 100-.mu.l incubation mixture containing 50 mM .beta.-benzyl-GlcNAc, 10 mM MnCl.sub.2, 10 mM Tris-HCl, pH 8.0, 500 .mu.M UDP-Gal or UDP-GalNAc, 20 ng of Gal-T1, and 0.5 .mu.Cl of [.sup.3H]UDP-Gal or [.sup.3H]UDP-GalNAc was used for each Gal-T or GalNAc-T reaction. The incubation was carried out at 37.degree. C. for 10 mM The reaction was terminated by adding 200 .mu.l of cold 50 mM EDTA, and the mixture was passed through a 0.5-ml bed volume column of AG1-X8 cation resin (Bio-Rad) to remove any unreacted [.sup.3H]UDP-Gal or [.sup.3H]UDP-GalNAc. The column was washed successfully with 300, 400, and 500 .mu.l of water, and the column flow-through was diluted with Biosafe scintillation fluid; radioactivity was measured with a Beckman counter. A reaction without the acceptor sugar was used as a control. A similar assay was carried out to measure the GalNAc-T activity with Glc and other acceptors in the presence of 50 .mu.M bovine LA (Sigma).

The in vitro assay for enzyme activity (beta Gal T1, double mutant beta-gal) can be performed as described (Boeggeman et al., Glycobiology, 12:395-407 (2002)). The .sup.3H-labeled-UDP-Gal or UDP-Galactose was used as sugar donor and GlcNAc as the sugar acceptor. A reaction without GlcNAc was used as a control.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

Amado, M., Almeida, R., Schwientek, T., and Clausen, H. (1999) Identification and characterization of large galactosyltransferase gene families: galactosyltransferases for all functions. Biochim Biophys. Acta 1473, 35-53.

Bell, J. E., Beyer, T. A., and Hill, R. (1976) The kinetic mechanism of bovine milk galactosyltransferase. The role of R-lactalbumin, J. Biol. Chem. 251, 3003-3013.

Berger, E. G. and Rohrer, J. (2003) Galactosyltransferase—still up and running Biochimie 85, 261-274.

Boeggeman, E., and Qasba, P. K. (2002) Studies on the metal binding sites in the catalytic domain of â1,4-galactosyltransferase, Glycobiology 12, 395-407.

Boeggeman, E., Balaji, P. V., Sethi, N., Masibay, A. S., and Qasba, P. K. (1993) Expression of deletion constructs of bovine beta-1,4-galactosyltransferase in *Escherichia coli*: importance of Cys 134 for its activity, Protein Eng. 6, 779-785.

Boeggeman, E. E., Ramakrishnan, B. and Qasba, P. K. The N-terminal stem region of bovine and human beta1,4-galactosyltransferase I increases the in vitro folding efficiency of their catalytic domain from inclusion bodies. Protein Expr Purif. (2003) 30, 219-29.

Boeggeman E. E., Ramakrishnan B., Kilgore C., Khidekel N., Hsieh-Wilson L. C., Simpson J. T., and Qasba P. K. (1993) Direct Identification of Nonreducing GlcNAc Residues on N-Glycans of Glycoproteins Using a Novel Chemoenzymatic Method. Bioconjugate Chem. 2007, 18, 806-814.

Boix, E. et al. (2001) Structure of UDP complex of UDP-galactose: b-galactoside-a-1,3-galactosyltransferase at 1.53-A° resolution reveals a conformational change in the catalytically important C terminus. J. Biol. Chem. 276, 48608-48614

Brew, K., Vanaman, T. C., and Hill, R. L. (1968) The role of R-lactalbumin and the A protein in lactose synthetase: a unique mechanism for the control of a biological reaction, Proc. Natl. Acad. Sci. U.S.A. 59, 491-497.

Brodbeck, U., Denton, W. L., Tanahashi, N., and Ebner, K. E. (1967) The isolation and identification of the B protein of lactose synthetase as R-lactalbumin, J. Biol. Chem. 242, 1391-1397.

Fritz. T. A., Raman, J., and Tabak, L. A. Dynamic association between the catalytic and lectin domains of human UDP-GalNAc:polypeptide alpha-N-acetylgalactosaminyltransferase-2. J Biol. Chem. (2006) 281, 8613-9.

Gastinel, L. N., Cambillau, C., and Bourne, Y. (1999) Crystal structures of the bovine â4-galactosyltransferase catalytic domain and its complex with uridine diphosphogalactose, EMBO J. 18, 3546-3557.

Geren, C. R., Magee, S. C., and Ebner, K. E. (1975) Circular dichroism changes in galactosyltransferase upon substrate binding, Biochemistry 14, 1461-1463.

Gunasekaran, K., Buyong, M., Ramakrishnan, B., Qasba, P. K., and Nussinov, R. (2003) Interdependence of backbone flexibility, residue conservation, and enzyme function: a case study on beta-1,4-galactosyltransferase-I, Biochemistry 42, 3674-3687.

Hennet, T. (2002) The galactosyltransferase family. Cell. Mol. Life. Sci. 59, 1081-1095.

Hu, Y. et al. (2003) Crystal structure of the MurG:UDP-GlcNAc complex reveals common structural principles of a superfamily of glycosyltransferases. Proc. Natl. Acad. Sci. U.S.A. 100, 845-849

Kakuda, S., Shiba, T., Ishiguro, M., Tagawa, H., Oka, S., Kajihara, Y., Kawasaki, T., Wakatsuki, S., and Kato, R. (2004) Structural basis for acceptor substrate recognition of a human glucuronyltransferase, GlcAT-P, an enzyme critical in the biosynthesis of the carbohydrate epitope HNK-1. J. Biol. Chem. 279, 22693-22703.

Lobsanov, Y. D. et al. (2004) Structure of Kre2p/Mntlp: a yeast a1,2-mannosyltransferase involved in mannoprotein biosynthesis. J. Biol. Chem. 279, 17921-17931

Lowe, J. B., and Marth, J. D. (2003) A genetic approach to mammalian glycan function. Annu. ReV. Biochem. 72, 643-691.

Marcus, S. L., Polakowski, R., Seto, N. O. L., Leinala, E., Borisova, S., Blancher, A., Roubinet, F., Evans, S. V., and Palcic, M. M. (2003) A single point mutation reverses the donor specificity of human blood group B-synthesizing galactosyltransferase. J. Biol. Chem. 278, 12403-12405.

Morera, S. et al. (1999) T4 phage b-glucosyltransferase: substrate binding and proposed catalytic mechanism. J. Mol. Biol. 292, 717-730.

Mulichak, A. M. et al. (2001) Structure of the UDP-glucosyltransferase GtfB that modifies the heptapeptide aglycone in the biosynthesis of vancomycin group antibiotics. Structure 9, 547-557.

Negishi, M. et al. (2003) Glucosaminylglycan biosynthesis: what we can learn from the X-ray crystal structures of glycosyltransferases GlcAT1 and EXTL2. Biochem. Biophys. Res. Commun. 303, 393-398.

Powell, J. T., and Brew, K. (1976) Metal ion activation of galactosyltransferase, J. Biol. Chem. 251, 3645-3652.

Pedersen, L. C., Darden, T. A., and Negishi, M. (2002) Crystal structure of beta 1,3 glucuronyltransferase I in complex with active donor substrate UDP-GlcUA. J. Biol. Chem. 277, 21869-21873.

Powell, J. T., and Brew, K. (1976) A comparison of the interactions of galactosyltransferase with a glycoprotein substrate (ovalbumin) and with R-lactalbumin, J. Biol. Chem. 251, 3653-3663.

Qasba, P. K., Ramakrishnan, B., and Boeggeman, E. (2005) Substrate-induced conformational changes in glycosyltransferases. Trends Biochem. Sci. 30, 53-62.

Ramakrishnan, B., Boeggeman, E, and Qasba P. K. (2004), Effect of the Met344His Mutation on the Conformational Dynamics of Bovine beta-1,4-Galactosyltransferase: Crystal Structure of the Met344His Mutant in Complex with Chitobiose. Biochemistry 2004, 43, 12513-12522.

Ramakrishnan, B., and Qasba, P. K. (2001) Crystal structure of lactose synthase reveals a large conformational change in its catalytic component, the beta-1,4-galactosyltransferase-I, J. Mol. Biol. 310, 205-218.

Ramakrishnan, B., Shah, P. S., and Qasba, P. K. (2001a) R-Lactalbumin (LA) stimulates milk beta-1,4-galactosyltransferase I (beta4Gal-T1) to transfer glucose from UDP-glucose to N-acetylglucosamine. Crystal structure of beta4Gal-T1âLA complex with UDP-Glc, J. Biol. Chem. 276, 37665-37671.

Ramakrishnan, B., and Qasba, P. K. (2002) Structure-based design of beta1,4-galactosyltransferase I (beta4Gal-T1) with equally efficient N-acetylgalactosaminyltransferase activity: point mutation broadens beta4Gal-T1 donor specificity, J. Biol. Chem. 277, 20833-20839.

Ramakrishnan, B., Balaji, P. V., and Qasba, P. K. (2002a) Crystal structure of beta 1,4-galactosyltransferase complex with UDP-Gal reveals an oligosaccharide acceptor binding site, J. Mol. Biol. 318, 491-502.

Ramakrishnan, B., and Qasba, P. K. (2003) Comparison of the closed conformation of the beta1,4-galactosyltransferase-1 (beta4Gal-T1) in the presence and absence of R-lactalbumin (LA), J. Biomol. Struct. Dyn. 21, 1-8.

Ramakrishnan, B., Boeggeman, E., Ramasamy, V., and Qasba, P. K. (2004a) Structure and catalytic cycle of beta-1,4-galactosyltransferrase. Curr. Opin. Struct. Biol. 14, 593-600

Raman, R., Sasisekharan, V., and Sasisekharan, R. (2005) Structural insights into biological roles of protein-glycosaminoglycan interactions. Chem. Biol. 12, 267-277.

Ramasamy, V., Ramakrishnan, B., Boeggeman, E., and Qasba, P. K. (2003) The role of tryptophan 314 in the conformational changes of â1,4-galactosyltransferase-I, J. Mol. Biol. 331, 1065-1076.

Takase, K., and Ebner, K. E. (1984) Interaction of galactosyltransferase with R-lactalbumin and substrates, Curr. Top. Cell Regul. 24, 51-62.

Unligil, U. M. and Rini, J. M. (2000) Glycosyltransferase structure and mechanism. Curr. Opin. Struct. Biol. 10, 510-517.

---

What is claimed is:

1. A method of coupling an agent to a carrier protein comprising:

incubating a reaction mixture comprising a bioactive agent, a carrier protein and a polypeptide fragment of a mutated alpha 1,3 N-acetylgalactosaminyltransferase (alpha 3GalNAc T) that is a mutated form of a 1,3 galactosyltransferase (alpha 3 Gal-T) comprising one or more mutations in the sugar donor binding site or hinge region of the alpha 3 Gal-T and that retains the ability to transfer a donor sugar with a chemically reactive functional group to a sugar acceptor, wherein said sugar acceptor is attached to the carrier protein and wherein said donor sugar is transferred to said sugar acceptor and said transferred donor sugar is then coupled to the bioactive agent having a group that reacts with said chemically reactive functional group, thereby forming an oligosaccharide that couples said bioactive agent to said carrier protein.

2. The method of claim 1, wherein said oligosaccharide is a trisaccharide.

3. The method of claim 2, wherein the trisaccharide is selected from the group consisting of GalNAc alpha1-3-Gal beta 1-4GlcNAc and 2'-modified-Gal alpha 1-3-Gal beta 1-4GlcNAc.

4. The method of claim 1, wherein said polypeptide fragment comprises any one of SEQ ID NO: 2, SEQ ID NO: 4, SEQ ID NO: 6, SEQ ID NO: 8, SEQ ID NO: 10, SEQ ID NO; 12, SEQ ID NO: 14, SEQ ID NO: 16, SEQ ID NO: 18 and SEQ ID NO: 20.

5. The method of claim 1, wherein said chemically reactive functional group of said donor sugar is selected from the group consisting of a ketone, an azido and a thiol functionality.

6. The method of claim 1, wherein said donor sugar is a galactose which is modified at the C2 position by the addition of ketone functionality.

7. The method of claim 1, wherein said donor sugar is a galactose which is modified by the addition of an azido group.

8. The method of claim 1, wherein said agent is selected from the group consisting of a single chain antibody, a bacterial toxin, a growth factor, a therapeutic agent, a targeting agent, a contrast agent, a chemical label, a radiolabel, and a fluorescent label.

9. The method of claim 1, wherein said carrier protein is selected from the group consisting of ovalbumin and IgG1.

* * * * *

SEQUENCE LISTING

<160> NUMBER OF SEQ ID NOS: 21

<210> SEQ ID NO 1
<211> LENGTH: 927
<212> TYPE: DNA
<213> ORGANISM: Bos sp.
<220> FEATURE:
<221> NAME/KEY: modified_base
<222> LOCATION: (18)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other

<400> SEQUENCE: 1

```
atggctagca tgactggngn ncagcaaatg ggtcgcggat cccaccacca ccaccaccac    60
gaaagcaagc ttaagctatc ggactggttc aacccattta aacgcccccga ggttgtgacc   120 atgacgaagt ggaaggctcc agtggtgtgg gaaggcactt acaacagagc cgtcttagac   180
aattattatg ccaagcagaa aattaccgtc ggcctgacgg ttttcgccgt cggaagatac   240
attgagcatt acttggagga gttcttaacg tctgctaata agcacttcat ggttggccac   300
ccagtcatct tttatatcat ggtagatgat gtctccagga tgcctttgat agagtttgggt   360 cctctgcgct ccttcaaagt gtttaagatc aaggctgaga agaggtggca ggatatcagc   420
atgatgcgca tgaagactat cggggagcac attgtggccc acatccagca tgaggttgac   480 ttcctttct gcatggatgt ggaccaggtc ttccaagaca gtttggggt ggagaccctg   540 ggcgagtcgg tggcccagct acaagcctgg tggtacaagg cagatcccaa tgacttcacc   600
tacgagaggc ggaaggagtc tgcagcatac attcccttcg gcgaagggga tttttattac   660
catgcagcca tttttggggg aacacccact caggtcctta acatcaccca ggaatgcttc   720
aaaggaatcc tcaaggacaa gaaaaatgac atagaagccc aatggcatga tgaaagccat   780
ctaaacaagt atttccttct caacaaaccc actaaaatct tatccccgga atactgctgg   840
gattatcaca taggcctacc ttcggatatt aagctcgtca agatgtcttg gcagacaaaa   900
gagtataatg tggttagaaa taatgtc                                        927
```

<210> SEQ ID NO 2
<211> LENGTH: 309
<212> TYPE: PRT

```
<213> ORGANISM: Bos sp.
<220> FEATURE:
<221> NAME/KEY: MOD_RES
<222> LOCATION: (7)
<223> OTHER INFORMATION: Any amino acid

<400> SEQUENCE: 2
```

Met Ala Ser Met Thr Gly Xaa Gln Gln Met Gly Arg Gly Ser His His
 1               5                  10                  15

His His His Glu Ser Lys Leu Lys Leu Ser Asp Trp Phe Asn Pro
        20                  25                  30

Phe Lys Arg Pro Glu Val Val Thr Met Thr Lys Trp Lys Ala Pro Val
            35                  40                  45

Val Trp Glu Gly Thr Tyr Asn Arg Ala Val Leu Asp Asn Tyr Tyr Ala
 50                  55                  60

Lys Gln Lys Ile Thr Val Gly Leu Thr Val Phe Ala Val Gly Arg Tyr
 65                  70                  75                  80

Ile Glu His Tyr Leu Glu Glu Phe Leu Thr Ser Ala Asn Lys His Phe
                85                  90                  95

Met Val Gly His Pro Val Ile Phe Tyr Ile Met Val Asp Asp Val Ser
            100                 105                 110

Arg Met Pro Leu Ile Glu Leu Gly Pro Leu Arg Ser Phe Lys Val Phe
        115                 120                 125

Lys Ile Lys Ala Glu Lys Arg Trp Gln Asp Ile Ser Met Met Arg Met
130                 135                 140

Lys Thr Ile Gly Glu His Ile Val Ala His Ile Gln His Glu Val Asp
145                 150                 155                 160

Phe Leu Phe Cys Met Asp Val Asp Gln Val Phe Gln Asp Lys Phe Gly
                165                 170                 175

Val Glu Thr Leu Gly Glu Ser Val Ala Gln Leu Gln Ala Trp Trp Tyr
            180                 185                 190

Lys Ala Asp Pro Asn Asp Phe Thr Tyr Glu Arg Arg Lys Glu Ser Ala
        195                 200                 205

Ala Tyr Ile Pro Phe Gly Glu Gly Asp Phe Tyr Tyr His Ala Ala Ile
    210                 215                 220

Phe Gly Gly Thr Pro Thr Gln Val Leu Asn Ile Thr Gln Glu Cys Phe
225                 230                 235                 240

Lys Gly Ile Leu Lys Asp Lys Lys Asn Asp Ile Glu Ala Gln Trp His
                245                 250                 255

Asp Glu Ser His Leu Asn Lys Tyr Phe Leu Leu Asn Lys Pro Thr Lys
            260                 265                 270

Ile Leu Ser Pro Glu Tyr Cys Trp Asp Tyr His Ile Gly Leu Pro Ser
        275                 280                 285

Asp Ile Lys Leu Val Lys Met Ser Trp Gln Thr Lys Glu Tyr Asn Val
    290                 295                 300

Val Arg Asn Asn Val
305

```
<210> SEQ ID NO 3
<211> LENGTH: 927
<212> TYPE: DNA
<213> ORGANISM: Bos sp.
<220> FEATURE:
<221> NAME/KEY: modified_base
<222> LOCATION: (21)
<223> OTHER INFORMATION: a, c, t, g, unknown or other

<400> SEQUENCE: 3
```

```
atggctagca tgactggtgg ncagcaaatg ggtcgcggat cccaccacca ccaccaccac    60
gaaagcaagc ttaagctatc ggactggttc aacccattta aacgccccga ggttgtgacc   120
atgacgaagt ggaaggctcc agtggtgtgg aaggcactt  acaacagagc cgtcttagac   180
aattattatg ccaagcagaa aattaccgtc ggcctgacgg ttttcgccgt cggaagatac   240
attgagcatt acttggagga gttcttaacg tctgctaata agcacttcat ggttggccac   300
ccagtcatct tttatatcat ggtagatgat gtctccagga tgcctttgat agagttgggt   360
cctctgcgct ccttcaaagt gtttaagatc aagcctgaga gaggtggca  ggacatcagc   420 atgatgcgca tgaagactat cggggagcac attgtggccc acatccagca tgaggttgac   480
ttccttttct gcatggatgt ggaccaggtc ttccaagaca gtttggggt  ggagaccctg   540 ggcgagtcgg tggcccagct acaagcctgg tggtacaagg cagatcccaa tgacttcacc   600
tacgagaggc ggaaggagtc tgcagcatac attcccttcg gcgaagggga ttttattac   660 ctaggaggca ttttggggg  aacacccact caggtcctta acatcaccca ggaatgcttc   720
aaaggaatcc tcaaggacaa gaaaaatgac atagaagccc aatggcatga tgaaagccat   780
ctaaacaagt atttccttct caacaaaccc actaaaatct atccccgga  atactgctgg   840 gattatcaca taggcctacc ttcggatatt aagctcgtca agatgtcttg gcagacaaaa   900
gagtataatg tggttagaaa taatgtc                                      927
```

<210> SEQ ID NO 4
<211> LENGTH: 309
<212> TYPE: PRT
<213> ORGANISM: Bos sp.

<400> SEQUENCE: 4

```
Met Ala Ser Met Thr Gly Gly Gln Gln Met Gly Arg Gly Ser His His
  1               5                  10                  15

His His His His Glu Ser Lys Leu Lys Leu Ser Asp Trp Phe Asn Pro
             20                  25                  30

Phe Lys Arg Pro Glu Val Val Thr Met Thr Lys Trp Lys Ala Pro Val
         35                  40                  45

Val Trp Glu Gly Thr Tyr Asn Arg Ala Val Leu Asp Asn Tyr Tyr Ala
     50                  55                  60

Lys Gln Lys Ile Thr Val Gly Leu Thr Val Phe Ala Val Gly Arg Tyr
 65                  70                  75                  80

Ile Glu His Tyr Leu Glu Glu Phe Leu Thr Ser Ala Asn Lys His Phe
                 85                  90                  95

Met Val Gly His Pro Val Ile Phe Tyr Ile Met Val Asp Asp Val Ser
            100                 105                 110

Arg Met Pro Leu Ile Glu Leu Gly Pro Leu Arg Ser Phe Lys Val Phe
        115                 120                 125

Lys Ile Lys Pro Glu Lys Arg Trp Gln Asp Ile Ser Met Met Arg Met
    130                 135                 140

Lys Thr Ile Gly Glu His Ile Val Ala His Ile Gln His Glu Val Asp
145                 150                 155                 160

Phe Leu Phe Cys Met Asp Val Asp Gln Val Phe Gln Asp Lys Phe Gly
                165                 170                 175

Val Glu Thr Leu Gly Glu Ser Val Ala Gln Leu Gln Ala Trp Trp Tyr
            180                 185                 190

Lys Ala Asp Pro Asn Asp Phe Thr Tyr Glu Arg Arg Lys Glu Ser Ala
        195                 200                 205
```

```
Ala Tyr Ile Pro Phe Gly Glu Gly Asp Phe Tyr Tyr Leu Gly Gly Ile
            210                 215                 220

Phe Gly Gly Thr Pro Thr Gln Val Leu Asn Ile Thr Gln Glu Cys Phe
225                 230                 235                 240

Lys Gly Ile Leu Lys Asp Lys Asn Asp Ile Glu Ala Gln Trp His
            245                 250                 255

Asp Glu Ser His Leu Asn Lys Tyr Phe Leu Leu Asn Lys Pro Thr Lys
            260                 265                 270

Ile Leu Ser Pro Glu Tyr Cys Trp Asp Tyr His Ile Gly Leu Pro Ser
        275                 280                 285

Asp Ile Lys Leu Val Lys Met Ser Trp Gln Thr Lys Glu Tyr Asn Val
    290                 295                 300

Val Arg Asn Asn Val
305

<210> SEQ ID NO 5
<211> LENGTH: 927
<212> TYPE: DNA
<213> ORGANISM: Bos sp.
<220> FEATURE:
<221> NAME/KEY: modified_base
<222> LOCATION: (21)
<223> OTHER INFORMATION: a, c, t, g, unknown or other

<400> SEQUENCE: 5
atggctagca tgactggtgg ncagcaaatg ggtcgcggat cccaccacca ccaccaccac     60
gaaagcaagc ttaagctatc ggactggttc aacccattta acgccccgga ggttgtgacc    120
atgacgaagt ggaaggctcc agtggtgtgg aaggcactt acaacagagc cgtcttagac     180
aattattatg ccaagcagaa aattaccgtc ggcctgacgg ttttcgccgt cggaagatac    240
attgagcatt acttggagga gttcttaacg tctgctaata agcacttcat ggttggccac    300
ccagtcatct tttatatcat ggtagatgat gtctccagga tgcctttgat agagttgggt    360
cctctgcgct ccttcaaagt gtttaagatc aaggctgaga gaggtggca ggatatcagc     420 atgatgcgca tgaagactat cggggagcac attgtggccc acatccagca tgaggttgac    480 ttcctttct gcatggacgt cgacatggtc ttccaagaca gtttgggt ggagaccctg       540 ggcgagtcgg tggcccagct acaagcctgg tggtacaagg cagatcccaa tgacttcacc    600
tacgagaggc ggaaggagtc tgcagcatac attcccttcg gcgaagggga ttttattac    660 tccggaggca ttttggggg aacacccact caggtcctta acatcaccca ggaatgcttc    720
aaaggaatcc tcaaggacaa gaaaaatgac atagaagccc aatggcatga tgaaagccat    780
ctaaacaagt atttccttct caacaaacct actaaaatct tatccccgga atactgctgg    840
gattatcaca taggcctacc ttcggatatt aagcttgtca gatgtcttg gcagacaaaa    900 gagtataatg tggttagaaa taatgtc                                        927

<210> SEQ ID NO 6
<211> LENGTH: 309
<212> TYPE: PRT
<213> ORGANISM: Bos sp.

<400> SEQUENCE: 6

Met Ala Ser Met Thr Gly Gly Gln Gln Met Gly Arg Gly Ser His His
1               5                   10                  15

His His His His Glu Ser Lys Leu Lys Leu Ser Asp Trp Phe Asn Pro
            20                  25                  30
```

Phe Lys Arg Pro Glu Val Val Thr Met Thr Lys Trp Lys Ala Pro Val
                 35                  40                  45

Val Trp Glu Gly Thr Tyr Asn Arg Ala Val Leu Asp Asn Tyr Tyr Ala
     50                  55                  60

Lys Gln Lys Ile Thr Val Gly Leu Thr Val Phe Ala Val Gly Arg Tyr
 65                  70                  75                  80

Ile Glu His Tyr Leu Glu Glu Phe Leu Thr Ser Ala Asn Lys His Phe
                 85                  90                  95

Met Val Gly His Pro Val Ile Phe Tyr Ile Met Val Asp Asp Val Ser
                100                 105                 110

Arg Met Pro Leu Ile Glu Leu Gly Pro Leu Arg Ser Phe Lys Val Phe
                115                 120                 125

Lys Ile Lys Ala Glu Lys Arg Trp Gln Asp Ile Ser Met Met Arg Met
130                 135                 140

Lys Thr Ile Gly Glu His Ile Val Ala His Ile Gln His Glu Val Asp
145                 150                 155                 160

Phe Leu Phe Cys Met Asp Val Asp Met Val Phe Gln Asp Lys Phe Gly
                165                 170                 175

Val Glu Thr Leu Gly Glu Ser Val Ala Gln Leu Gln Ala Trp Trp Tyr
                180                 185                 190

Lys Ala Asp Pro Asn Asp Phe Thr Tyr Glu Arg Arg Lys Glu Ser Ala
                195                 200                 205

Ala Tyr Ile Pro Phe Gly Glu Gly Asp Phe Tyr Tyr Ser Gly Gly Ile
                210                 215                 220

Phe Gly Gly Thr Pro Thr Gln Val Leu Asn Ile Thr Gln Glu Cys Phe
225                 230                 235                 240

Lys Gly Ile Leu Lys Asp Lys Lys Asn Asp Ile Glu Ala Gln Trp His
                245                 250                 255

Asp Glu Ser His Leu Asn Lys Tyr Phe Leu Leu Asn Lys Pro Thr Lys
                260                 265                 270

Ile Leu Ser Pro Glu Tyr Cys Trp Asp Tyr His Ile Gly Leu Pro Ser
                275                 280                 285

Asp Ile Lys Leu Val Lys Met Ser Trp Gln Thr Lys Glu Tyr Asn Val
                290                 295                 300

Val Arg Asn Asn Val
305

<210> SEQ ID NO 7
<211> LENGTH: 930
<212> TYPE: DNA
<213> ORGANISM: Bos sp.

<400> SEQUENCE: 7
atggctagca tgactggtgg acagcaaatg ggtcgcggat cccaccacca ccaccaccac      60
gaaagcaagc ttaagctatc ggactggttc aacccattta acgccccga ggttgtgacc     120 atgacgaagt ggaaggctcc agtggtgtgg aaggcactt acaacagagc cgtcttagac      180
aattattatg ccaagcagaa aattaccgtc ggcctgacgg ttttcgccgt cggaagatac     240
attgagcatt acttggagga gttcttaacg tctgctaata gcacttcat ggtgggccac      300 ccagtcatct tttatatcat ggtagatgat gtctccagga tgcctttgat agagttgggt     360
cctctgcgct ccttcaaagt gtttaagatc aagcctgaga gaggtggca ggacatcagc      420 atgatgcgca tgaagactat cggggagcac attgtggccc acatccagca tgaggttgac     480

-continued

```
ttccttttct gcatggatgt ggaccaggtc ttccaagaca agtttggggt ggagaccctg      540
ggcgagtcgg tggcccagct acaagcctgg tggtacaagg cagatcccaa tgacttcacc      600
tacgagaggc ggaaggagtc tgcagcatac attcccttcg gcgaagggga ttttttattac    660
tccgccggca ttttgggggg aacacccact caggtcctta acatcaccca ggaatgcttc     720
aaaggaatcc tcaaggacaa gaaaaatgac atagaagccc aatggcatga tgaaagccat     780
ctaaacaagt atttccttct caacaaacct actaaaatct atccccggga atactgctgg     840
gattatcaca taggcctacc ttcggatatt aagcttgtca agatgtcttg gcagacaaaa     900
gagtataatg tggttagaaa taatgtctga                                       930
```

```
<210> SEQ ID NO 8
<211> LENGTH: 309
<212> TYPE: PRT
<213> ORGANISM: Bos sp.

<400> SEQUENCE: 8
```

```
Met Ala Ser Met Thr Gly Gly Gln Gln Met Gly Arg Gly Ser His His
1               5                   10                  15

His His His His Glu Ser Lys Leu Lys Leu Ser Asp Trp Phe Asn Pro
            20                  25                  30

Phe Lys Arg Pro Glu Val Val Thr Met Thr Lys Trp Lys Ala Pro Val
        35                  40                  45

Val Trp Glu Gly Thr Tyr Asn Arg Ala Val Leu Asp Asn Tyr Tyr Ala
    50                  55                  60

Lys Gln Lys Ile Thr Val Gly Leu Thr Val Phe Ala Val Gly Arg Tyr
65                  70                  75                  80

Ile Glu His Tyr Leu Glu Glu Phe Leu Thr Ser Ala Asn Lys His Phe
                85                  90                  95

Met Val Gly His Pro Val Ile Phe Tyr Ile Met Val Asp Asp Val Ser
            100                 105                 110

Arg Met Pro Leu Ile Glu Leu Gly Pro Leu Arg Ser Phe Lys Val Phe
        115                 120                 125

Lys Ile Lys Pro Glu Lys Arg Trp Gln Asp Ile Ser Met Met Arg Met
    130                 135                 140

Lys Thr Ile Gly Glu His Ile Val Ala His Ile Gln His Glu Val Asp
145                 150                 155                 160

Phe Leu Phe Cys Met Asp Val Asp Gln Val Phe Gln Asp Lys Phe Gly
                165                 170                 175

Val Glu Thr Leu Gly Glu Ser Val Ala Gln Leu Gln Ala Trp Trp Tyr
            180                 185                 190

Lys Ala Asp Pro Asn Asp Phe Thr Tyr Glu Arg Arg Lys Glu Ser Ala
        195                 200                 205

Ala Tyr Ile Pro Phe Gly Glu Gly Asp Phe Tyr Tyr Ser Ala Gly Ile
    210                 215                 220

Phe Gly Gly Thr Pro Thr Gln Val Leu Asn Ile Thr Gln Glu Cys Phe
225                 230                 235                 240

Lys Gly Ile Leu Lys Asp Lys Lys Asn Asp Ile Glu Ala Gln Trp His
                245                 250                 255

Asp Glu Ser His Leu Asn Lys Tyr Phe Leu Leu Asn Lys Pro Thr Lys
            260                 265                 270

Ile Leu Ser Pro Glu Tyr Cys Trp Asp Tyr His Ile Gly Leu Pro Ser
        275                 280                 285

Asp Ile Lys Leu Val Lys Met Ser Trp Gln Thr Lys Glu Tyr Asn Val
```

Val Arg Asn Asn Val
305

<210> SEQ ID NO 9
<211> LENGTH: 927
<212> TYPE: DNA
<213> ORGANISM: Bos sp.

<400> SEQUENCE: 9

```
atggctagca tgactggtgg acagcaaatg ggtcgcggat cccaccacca ccaccaccac      60
gaaagcaagc ttaagctatc ggactggttc aacccattta acgccccga ggttgtgacc      120
atgacgaagt ggaaggctcc agtggtgtgg aaggcactt acaacagagc cgtcttagac      180
aattattatg ccaagcagaa aattaccgtc ggcctgacgg ttttcgccgt cggaagatac     240
attgagcatt acttggagga gttcttaacg tctgctaata agcacttcat ggttggccac     300
ccagtcatct tttatatcat ggtagatgat gtctccagga tgcctttgat agagttgggt     360
cctctgcgct ccttcaaagt gtttaagatc aagtctgaga gaggtggca ggatatcagc      420
atgatgcgca tgaagactat cggggagcac attgtggccc acatccagca tgaggttgac     480
ttccttttct gcatggatgt ggaccaggtc ttccaagaca gtttggggt ggagaccctg      540
ggcgagtcgg tggcccagct acaagcctgg tggtacaagg cagatcccaa tgacttcacc     600
tacgagaggc ggaaggagtc tgcagcatac attcccttcg gcgaagggga ttttattac      660
tccggaggca ttttggggg aacacccact caggtcctta acatcaccca ggaatgcttc     720
aaaggaatcc tcaaggacaa gaaaaatgac atagaagccc aatggcatga tgaaagccat     780
ctaaacaagt atttccttct caacaaaccc actaaaatct tatccccgga atactgctgg     840
gattatcaca taggcctacc ttcggatatt aagctcgtca gatgtcttg gcagacaaaa      900
gagtataatg tggttagaaa taatgtc                                         927
```

<210> SEQ ID NO 10
<211> LENGTH: 309
<212> TYPE: PRT
<213> ORGANISM: Bos sp.

<400> SEQUENCE: 10

Met Ala Ser Met Thr Gly Gly Gln Gln Met Gly Arg Gly Ser His His
1               5                   10                  15

His His His His Glu Ser Lys Leu Lys Leu Ser Asp Trp Phe Asn Pro
            20                  25                  30

Phe Lys Arg Pro Glu Val Val Thr Met Thr Lys Trp Lys Ala Pro Val
        35                  40                  45

Val Trp Glu Gly Thr Tyr Asn Arg Ala Val Leu Asp Asn Tyr Tyr Ala
    50                  55                  60

Lys Gln Lys Ile Thr Val Gly Leu Thr Val Phe Ala Val Gly Arg Tyr
65                  70                  75                  80

Ile Glu His Tyr Leu Glu Glu Phe Leu Thr Ser Ala Asn Lys His Phe
                85                  90                  95

Met Val Gly His Pro Val Ile Phe Tyr Ile Met Val Asp Asp Val Ser
            100                 105                 110

Arg Met Pro Leu Ile Glu Leu Gly Pro Leu Arg Ser Phe Lys Val Phe
        115                 120                 125

Lys Ile Lys Ser Glu Lys Arg Trp Gln Asp Ile Ser Met Met Arg Met
    130                 135                 140

```
Lys Thr Ile Gly Glu His Ile Val Ala His Ile Gln His Glu Val Asp
145                 150                 155                 160

Phe Leu Phe Cys Met Asp Val Asp Gln Val Phe Gln Asp Lys Phe Gly
                165                 170                 175

Val Glu Thr Leu Gly Glu Ser Val Ala Gln Leu Gln Ala Trp Trp Tyr
            180                 185                 190

Lys Ala Asp Pro Asn Asp Phe Thr Tyr Glu Arg Arg Lys Glu Ser Ala
        195                 200                 205

Ala Tyr Ile Pro Phe Gly Glu Gly Asp Phe Tyr Tyr Ser Gly Gly Ile
    210                 215                 220

Phe Gly Gly Thr Pro Thr Gln Val Leu Asn Ile Thr Gln Glu Cys Phe
225                 230                 235                 240

Lys Gly Ile Leu Lys Asp Lys Lys Asn Asp Ile Glu Ala Gln Trp His
                245                 250                 255

Asp Glu Ser His Leu Asn Lys Tyr Phe Leu Leu Asn Lys Pro Thr Lys
                260                 265                 270

Ile Leu Ser Pro Glu Tyr Cys Trp Asp Tyr His Ile Gly Leu Pro Ser
            275                 280                 285

Asp Ile Lys Leu Val Lys Met Ser Trp Gln Thr Lys Glu Tyr Asn Val
        290                 295                 300

Val Arg Asn Asn Val
305

<210> SEQ ID NO 11
<211> LENGTH: 926
<212> TYPE: DNA
<213> ORGANISM: Bos sp.
<220> FEATURE:
<221> NAME/KEY: modified_base
<222> LOCATION: (693)..(694)
<223> OTHER INFORMATION: a, c, t, g, unknown or other
<220> FEATURE:
<221> NAME/KEY: modified_base
<222> LOCATION: (711)
<223> OTHER INFORMATION: a, c, t, g, unknown or other

<400> SEQUENCE: 11
atggctagca tgactggtgg acagcaaatg ggtcgcggat cccaccacca ccaccaccac    60
gaaagcaagc ttaagctatc ggactggttc aacccattta acgccccga ggttgtgacc     120 atgacgaagt ggaaggctcc agtggtgtgg aaggcactt acaacagagc cgtcttagac     180
aattattatg ccaagcagaa aattaccgtc ggcctgacgg ttttcgccgt cggaagatac    240
attgagcatt acttggagga gttcttaacg tctgctaata agcacttcat ggttggccac    300
ccagtcatct tttatatcat ggtagatgat gtctccagga tgcctttgat agagttgggt    360
cctctgcgct ccttcaaagt gtttaagatc aaggctgaga gaggtggca ggatatcagc     420 atgatgcgca tgaagactat cggggagcac attgtgcccc acatccagca tgaggttgac    480
ttccttttct gcatggatgt ggaccaggtc ttccaagaca gtttggggt ggagaccctg     540 ggcgagtcgg tggcccagct acaagcctgg tggtacaagg cagatcccaa tgacttcacc    600
tacgagaggc ggaaggagtc tgcagcatac attcccttcg gcgaagggga ttttattac    660 tccggaggca ttttggggg aacacccact canntcctta acatcaccca ngaatgcttc    720
aaaggaatcc tcaaggacaa gaaaaatgac atagaagccc aatggcatga tgaaagccat    780
ctaaacaagt atttccttct caacaaaccc actaaaatct atccccgga atactgctgg     840 gattatcaca taggcctacc ttcggatatt aagctcgtca agatgtcttg gcagacaaaa    900
```
gagtataatg tggttagaaa taatgt 926

```
<210> SEQ ID NO 12
<211> LENGTH: 308
<212> TYPE: PRT
<213> ORGANISM: Bos sp.
<220> FEATURE:
<221> NAME/KEY: MOD_RES
<222> LOCATION: (231)..(232)
<223> OTHER INFORMATION: Any amino acid
<220> FEATURE:
<221> NAME/KEY: MOD_RES
<222> LOCATION: (237)
<223> OTHER INFORMATION: Any amino acid

<400> SEQUENCE: 12
```

Met Ala Ser Met Thr Gly Gly Gln Gln Met Gly Arg Gly Ser His His
 1               5                  10                  15

His His His His Glu Ser Lys Leu Lys Leu Ser Asp Trp Phe Asn Pro
             20                  25                  30

Phe Lys Arg Pro Glu Val Val Thr Met Thr Lys Trp Lys Ala Pro Val
         35                  40                  45

Val Trp Glu Gly Thr Tyr Asn Arg Ala Val Leu Asp Asn Tyr Tyr Ala
     50                  55                  60

Lys Gln Lys Ile Thr Val Gly Leu Thr Val Phe Ala Val Gly Arg Tyr
 65                  70                  75                  80

Ile Glu His Tyr Leu Glu Glu Phe Leu Thr Ser Ala Asn Lys His Phe
                 85                  90                  95

Met Val Gly His Pro Val Ile Phe Tyr Ile Met Val Asp Asp Val Ser
            100                 105                 110

Arg Met Pro Leu Ile Glu Leu Gly Pro Leu Arg Ser Phe Lys Val Phe
        115                 120                 125

Lys Ile Lys Ala Glu Lys Arg Trp Gln Asp Ile Ser Met Met Arg Met
    130                 135                 140

Lys Thr Ile Gly Glu His Ile Val Ala His Ile Gln His Glu Val Asp
145                 150                 155                 160

Phe Leu Phe Cys Met Asp Val Asp Gln Val Phe Gln Asp Lys Phe Gly
                165                 170                 175

Val Glu Thr Leu Gly Glu Ser Val Ala Gln Leu Gln Ala Trp Trp Tyr
            180                 185                 190

Lys Ala Asp Pro Asn Asp Phe Thr Tyr Glu Arg Arg Lys Glu Ser Ala
        195                 200                 205

Ala Tyr Ile Pro Phe Gly Glu Gly Asp Phe Tyr Tyr Ser Gly Gly Ile
    210                 215                 220

Phe Gly Gly Thr Pro Thr Xaa Xaa Leu Asn Ile Thr Xaa Glu Cys Phe
225                 230                 235                 240

Lys Gly Ile Leu Lys Asp Lys Lys Asn Asp Ile Glu Ala Gln Trp His
                245                 250                 255

Asp Glu Ser His Leu Asn Lys Tyr Phe Leu Leu Asn Lys Pro Thr Lys
            260                 265                 270

Ile Leu Ser Pro Glu Tyr Cys Trp Asp Tyr His Ile Gly Leu Pro Ser
        275                 280                 285

Asp Ile Lys Leu Val Lys Met Ser Trp Gln Thr Lys Glu Tyr Asn Val
    290                 295                 300

Val Arg Asn Asn
305

<210> SEQ ID NO 13
<211> LENGTH: 930
<212> TYPE: DNA
<213> ORGANISM: Bos sp.

<400> SEQUENCE: 13

```
atggctagca tgactggtgg acagcaaatg ggtcgcggat cccaccacca ccaccaccac      60
gaaagcaagc ttaagctatc ggactggttc aacccattta acgccccga ggttgtgacc      120
atgacgaagt ggaaggctcc agtggtgtgg aaggcactt acaacagagc cgtcttagac      180
aattattatg ccaagcagaa aattaccgtc ggcctgacgg ttttcgccgt cggaagatac      240
attgagcatt acttggagga gttcttaacg tctgctaata agcacttcat ggttggccac      300
ccagtcatct tttatatcat ggtagatgat gtctccagga tgcctttgat agagttgggt      360
cctctgcgct ccttcaaagt gtttaagatc aagcctgaga gaggtggca ggacatcagc      420
atgatgcgca tgaagactat cggggagcac attgtggccc acatccagca tgaggttgac      480
ttccttttct gcatggatgt ggaccaggtc ttccaagaca gtttggggt ggagaccctg      540
ggcgagtcgg tggcccagct acaagcctgg tggtacaagg cagatcccaa tgacttcacc      600
tacgagaggc ggaaggagtc tgcagcatac attcccttcg gcgaagggga ttttctttac      660
tccggaggca ttttgggggg aacacccact caggtcctta acatcaccca ggaatgcttc      720
aaaggaatcc tcaaggacaa gaaaaatgac atagaagccc aatggcatga tgaaagccat      780
ctaaacaagt atttccttct caacaaaccc actaaaatct tatccccgga atactgctgg      840
gattatcaca taggcctacc ttcggatatt aagctcgtca gatgtcttg gcagacaaaa      900
gagtataatg tggttagaaa taatgtctga                                       930
```

<210> SEQ ID NO 14
<211> LENGTH: 309
<212> TYPE: PRT
<213> ORGANISM: Bos sp.

<400> SEQUENCE: 14

```
Met Ala Ser Met Thr Gly Gly Gln Gln Met Gly Arg Gly Ser His His
  1               5                  10                  15

His His His His Glu Ser Lys Leu Lys Leu Ser Asp Trp Phe Asn Pro
                 20                  25                  30

Phe Lys Arg Pro Glu Val Val Thr Met Thr Lys Trp Lys Ala Pro Val
             35                  40                  45

Val Trp Glu Gly Thr Tyr Asn Arg Ala Val Leu Asp Asn Tyr Tyr Ala
     50                  55                  60

Lys Gln Lys Ile Thr Val Gly Leu Thr Val Phe Ala Val Gly Arg Tyr
 65                  70                  75                  80

Ile Glu His Tyr Leu Glu Glu Phe Leu Thr Ser Ala Asn Lys His Phe
                 85                  90                  95

Met Val Gly His Pro Val Ile Phe Tyr Ile Met Val Asp Asp Val Ser
            100                 105                 110

Arg Met Pro Leu Ile Glu Leu Gly Pro Leu Arg Ser Phe Lys Val Phe
        115                 120                 125

Lys Ile Lys Pro Glu Lys Arg Trp Gln Asp Ile Ser Met Met Arg Met
    130                 135                 140

Lys Thr Ile Gly Glu His Ile Val Ala His Ile Gln His Glu Val Asp
145                 150                 155                 160

Phe Leu Phe Cys Met Asp Val Asp Gln Val Phe Gln Asp Lys Phe Gly
```

```
                165                 170                 175
Val Glu Thr Leu Gly Glu Ser Val Ala Gln Leu Gln Ala Trp Trp Tyr
            180                 185                 190

Lys Ala Asp Pro Asn Asp Phe Thr Tyr Glu Arg Arg Lys Glu Ser Ala
        195                 200                 205

Ala Tyr Ile Pro Phe Gly Glu Gly Asp Phe Leu Tyr Ser Gly Gly Ile
    210                 215                 220

Phe Gly Gly Thr Pro Thr Gln Val Leu Asn Ile Thr Gln Glu Cys Phe
225                 230                 235                 240

Lys Gly Ile Leu Lys Asp Lys Lys Asn Asp Ile Glu Ala Gln Trp His
                245                 250                 255

Asp Glu Ser His Leu Asn Lys Tyr Phe Leu Leu Asn Lys Pro Thr Lys
            260                 265                 270

Ile Leu Ser Pro Glu Tyr Cys Trp Asp Tyr His Ile Gly Leu Pro Ser
        275                 280                 285

Asp Ile Lys Leu Val Lys Met Ser Trp Gln Thr Lys Glu Tyr Asn Val
    290                 295                 300

Val Arg Asn Asn Val
305
```

```
<210> SEQ ID NO 15
<211> LENGTH: 927
<212> TYPE: DNA
<213> ORGANISM: Bos sp.

<400> SEQUENCE: 15
atggctagca tgactggtgg acagcaaatg ggtcgcggat cccaccacca ccaccaccac     60
gaaagcaagc ttaagctatc ggactggttc aacccattta acgccccga ggttgtgacc    120 atgacgaagt ggaaggctcc agtggtgtgg aaggcactt acaacagagc cgtcttagac    180
aattattatg ccaagcagaa aattaccgtc ggcctgacgg ttttcgccgt cggaagatac    240
attgagcatt acttggagga gttcttaacg tctgctaata agcacttcat ggttggccac    300
ccagtcatct tttatatcat ggtagatgat gtctccagga tgccttttgat agagttgggt    360 cctctgcgct ccttcaaagt gtttaagatc aagtctgaga gaggtggca ggatatcagc    420 atgatgcgca tgaagactat cggggagcac attgtggccc acatccagca tgaggttgac    480
ttccttttct gcatggatgt ggaccaggtc ttccaagaca gtttggggt ggagaccctg    540 ggcgagtcgg tggcccagct acaagcctgg tggtacaagg cagatcccaa tgacttcacc    600
tacgagaggc ggaaggagtc tgcagcatac attcccttcg gcgaagggga ttttattac    660 catgcagcca tttttggggg aacacccact caggtcctta acatcaccca ggaatgcttc    720
aaaggaatcc tcaaggacaa gaaaaatgac atagaagccc aatggcatga tgaaagccat    780
ctaaacaagt atttccttct caacaaaccc actaaaatct atccccggaa atactgctgg    840
gattatcaca taggcctacc ttcggatatt aagctcgtca agatgtcttg gcagacaaaa    900
gagtataatg tggttagaaa taatgtc                                        927
```

```
<210> SEQ ID NO 16
<211> LENGTH: 309
<212> TYPE: PRT
<213> ORGANISM: Bos sp.

<400> SEQUENCE: 16

Met Ala Ser Met Thr Gly Gly Gln Gln Met Gly Arg Gly Ser His His
1               5                   10                  15
```

```
His His His His Glu Ser Lys Leu Lys Leu Ser Asp Trp Phe Asn Pro
             20                  25                  30

Phe Lys Arg Pro Glu Val Val Thr Met Thr Lys Trp Lys Ala Pro Val
         35                  40                  45

Val Trp Glu Gly Thr Tyr Asn Arg Ala Val Leu Asp Asn Tyr Tyr Ala
     50                  55                  60

Lys Gln Lys Ile Thr Val Gly Leu Thr Val Phe Ala Val Gly Arg Tyr
 65                  70                  75                  80

Ile Glu His Tyr Leu Glu Glu Phe Leu Thr Ser Ala Asn Lys His Phe
                 85                  90                  95

Met Val Gly His Pro Val Ile Phe Tyr Ile Met Val Asp Asp Val Ser
                100                 105                 110

Arg Met Pro Leu Ile Glu Leu Gly Pro Leu Arg Ser Phe Lys Val Phe
            115                 120                 125

Lys Ile Lys Ser Glu Lys Arg Trp Gln Asp Ile Ser Met Met Arg Met
130                 135                 140

Lys Thr Ile Gly Glu His Ile Val Ala His Ile Gln His Glu Val Asp
145                 150                 155                 160

Phe Leu Phe Cys Met Asp Val Asp Gln Val Phe Gln Asp Lys Phe Gly
                165                 170                 175

Val Glu Thr Leu Gly Glu Ser Val Ala Gln Leu Gln Ala Trp Trp Tyr
            180                 185                 190

Lys Ala Asp Pro Asn Asp Phe Thr Tyr Glu Arg Arg Lys Glu Ser Ala
        195                 200                 205

Ala Tyr Ile Pro Phe Gly Glu Gly Asp Phe Tyr Tyr His Ala Ala Ile
    210                 215                 220

Phe Gly Gly Thr Pro Thr Gln Val Leu Asn Ile Thr Gln Glu Cys Phe
225                 230                 235                 240

Lys Gly Ile Leu Lys Asp Lys Lys Asn Asp Ile Glu Ala Gln Trp His
                245                 250                 255

Asp Glu Ser His Leu Asn Lys Tyr Phe Leu Leu Asn Lys Pro Thr Lys
            260                 265                 270

Ile Leu Ser Pro Glu Tyr Cys Trp Asp Tyr His Ile Gly Leu Pro Ser
        275                 280                 285

Asp Ile Lys Leu Val Lys Met Ser Trp Gln Thr Lys Glu Tyr Asn Val
    290                 295                 300

Val Arg Asn Asn Val
305

<210> SEQ ID NO 17
<211> LENGTH: 927
<212> TYPE: DNA
<213> ORGANISM: Bos sp.
<220> FEATURE:
<221> NAME/KEY: modified_base
<222> LOCATION: (21)
<223> OTHER INFORMATION: a, c, t, g, unknown or other

<400> SEQUENCE: 17
atggctagca tgactggtgg ncagcaaatg ggtcgcggat cccaccacca ccaccaccac      60
gaaagcaagc ttaagctatc ggactggttc aacccattta acgccccga ggttgtgacc     120 atgacgaagt ggaaggctcc agtggtgtgg gaaggcactt acaacagagc cgtcttagac     180
aattattatg ccaagcagaa aattaccgtc ggcctgacgg ttttcgccgt cggaagatac     240
attgagcatt acttggagga gttcttaacg tctgctaata agcacttcat ggttggccac     300
```

```
ccagtcatct tttatatcat ggtagatgat gtctccagga tgcctttgat agagttgggt    360
cctctgcgct ccttcaaagt gtttaagatc aagcctgaga gaggtggca ggacatcagc     420
atgatgcgca tgaagactat cggggagcac attgtggccc acatccagca tgaggttgac    480
ttccttttct gcatggatgt ggaccaggtc ttccaagaca agtttggggt ggagaccctg    540
ggcgagtcgg tggcccagct acaagcctgg tggtacaagg cagatcccaa tgacttcacc    600
tacgagaggc ggaaggagtc tgcagcatac attcccttcg gcgaagggga ttttattac    660
tccggaggca ttttgggggg aacacccact caggtcctta acatcaccca ggaatgcttc    720
aaaggaatcc tcaaggacaa gaaaaatgac atagaagccc aatggcatga tgaaagccat    780
ctaaacaagt atttccttct caacaaaccc actaaaatct tatccccgga atactgctgg    840
gattatcaca taggcctacc ttcggatatt aagctcgtca agatgtcttg gcagacaaaa    900
gagtataatg tggttagaaa taatgtc                                        927
```

```
<210> SEQ ID NO 18
<211> LENGTH: 309
<212> TYPE: PRT
<213> ORGANISM: Bos sp.

<400> SEQUENCE: 18
```

| | | | | | | | | | | | | | | |
|---|---|---|---|---|---|---|---|---|---|---|---|---|---|---|
| Met | Ala | Ser | Met | Thr | Gly | Gly | Gln | Gln | Met | Gly | Arg | Gly | Ser | His |
| 1 | | | | 5 | | | | | 10 | | | | | 15 |
| His | His | His | His | Glu | Ser | Lys | Leu | Lys | Leu | Ser | Asp | Trp | Phe | Asn | Pro
| | | | 20 | | | | | 25 | | | | | 30 | |
| Phe | Lys | Arg | Pro | Glu | Val | Val | Thr | Met | Thr | Lys | Trp | Lys | Ala | Pro | Val
| | | 35 | | | | | 40 | | | | | 45 | | |
| Val | Trp | Glu | Gly | Thr | Tyr | Asn | Arg | Ala | Val | Leu | Asp | Asn | Tyr | Tyr | Ala
| | 50 | | | | | 55 | | | | | 60 | | | | |
| Lys | Gln | Lys | Ile | Thr | Val | Gly | Leu | Thr | Val | Phe | Ala | Val | Gly | Arg | Tyr
| 65 | | | | | 70 | | | | | 75 | | | | | 80
| Ile | Glu | His | Tyr | Leu | Glu | Glu | Phe | Leu | Thr | Ser | Ala | Asn | Lys | His | Phe
| | | | | 85 | | | | | 90 | | | | | 95 | |
| Met | Val | Gly | His | Pro | Val | Ile | Phe | Tyr | Ile | Met | Val | Asp | Asp | Val | Ser
| | | | 100 | | | | | 105 | | | | | 110 | | |
| Arg | Met | Pro | Leu | Ile | Glu | Leu | Gly | Pro | Leu | Arg | Ser | Phe | Lys | Val | Phe
| | | 115 | | | | | 120 | | | | | 125 | | | |
| Lys | Ile | Lys | Pro | Glu | Lys | Arg | Trp | Gln | Asp | Ile | Ser | Met | Met | Arg | Met
| 130 | | | | | 135 | | | | | 140 | | | | | |
| Lys | Thr | Ile | Gly | Glu | His | Ile | Val | Ala | His | Ile | Gln | His | Glu | Val | Asp
| 145 | | | | | 150 | | | | | 155 | | | | | 160
| Phe | Leu | Phe | Cys | Met | Asp | Val | Asp | Gln | Val | Phe | Gln | Asp | Lys | Phe | Gly
| | | | | 165 | | | | | 170 | | | | | 175 | |
| Val | Glu | Thr | Leu | Gly | Glu | Ser | Val | Ala | Gln | Leu | Gln | Ala | Trp | Trp | Tyr
| | | | 180 | | | | | 185 | | | | | 190 | | |
| Lys | Ala | Asp | Pro | Asn | Asp | Phe | Thr | Tyr | Glu | Arg | Arg | Lys | Glu | Ser | Ala
| | | 195 | | | | | 200 | | | | | 205 | | | |
| Ala | Tyr | Ile | Pro | Phe | Gly | Glu | Gly | Asp | Phe | Tyr | Tyr | Ser | Gly | Gly | Ile
| | 210 | | | | | 215 | | | | | 220 | | | | |
| Phe | Gly | Gly | Thr | Pro | Thr | Gln | Val | Leu | Asn | Ile | Thr | Gln | Glu | Cys | Phe
| 225 | | | | | 230 | | | | | 235 | | | | | 240
| Lys | Gly | Ile | Leu | Lys | Asp | Lys | Lys | Asn | Asp | Ile | Glu | Ala | Gln | Trp | His
| | | | | 245 | | | | | 250 | | | | | 255 | |

Asp Glu Ser His Leu Asn Lys Tyr Phe Leu Leu Asn Lys Pro Thr Lys
            260                 265                 270

Ile Leu Ser Pro Glu Tyr Cys Trp Asp Tyr His Ile Gly Leu Pro Ser
        275                 280                 285

Asp Ile Lys Leu Val Lys Met Ser Trp Gln Thr Lys Glu Tyr Asn Val
        290                 295                 300

Val Arg Asn Asn Val
305

<210> SEQ ID NO 19
<211> LENGTH: 927
<212> TYPE: DNA
<213> ORGANISM: Bos sp.

<400> SEQUENCE: 19

```
atggctagca tgactggtgg acagcaaatg ggtcgcggat cccaccacca ccaccaccac   60
gaaagcaagc ttaagctatc ggactggttc aacccattta acgccccga ggttgtgacc  120
atgacgaagt ggaaggctcc agtggtgtgg aaggcactt acaacagagc cgtcttagac  180
aattattatg ccaagcagaa aattaccgtc ggcctgacgg ttttcgccgt cggaagatac  240
attgagcatt acttggagga gttcttaacg tctgctaata agcacttcat ggtgggccac  300
ccagtcatct tttatatcat ggtagatgat gtctccagga tgcctttgat agagttgggt  360
cctctgcgct ccttcaaagt gtttaagatc aagcctgaga gaggtggca ggacatcagc  420
atgatgcgca tgaagactat cggggagcac attgtggccc acatccagca tgaggttgac  480
ttcctttttct gcatggatgt ggaccaggtc ttccaagaca gtttggggt ggagaccctg  540
ggcgagtcgg tggcccagct acaagcctgg tggtacaagg cagatcccaa tgacttcacc  600
tacgagaggc ggaaggagtc tgcagcatac attccctgg gcgaagggga tttttattac  660
acaggaggta ttttggggg aacacccact caggtcctta acatcaccca ggaatgcttc  720
aaaggaatcc tcaaggacaa gaaaaatgac atagaagccc aatggcatga tgaaagccat  780
ctaaacaagt atttccttct caacaaacct actaaaatct tatccccgga atactgctgg  840
gattatcaca taggcctacc ttcggatatt aagcttgtca agatgtcttg gcagacaaaa  900
gagtataatg tggttagaaa taatgtc                                     927
```

<210> SEQ ID NO 20
<211> LENGTH: 309
<212> TYPE: PRT
<213> ORGANISM: Bos sp.

<400> SEQUENCE: 20

Met Ala Ser Met Thr Gly Gly Gln Gln Met Gly Arg Gly Ser His His
1               5                   10                  15

His His His His Glu Ser Lys Leu Lys Leu Ser Asp Trp Phe Asn Pro
                20                  25                  30

Phe Lys Arg Pro Glu Val Val Thr Met Thr Lys Trp Lys Ala Pro Val
            35                  40                  45

Val Trp Glu Gly Thr Tyr Asn Arg Ala Val Leu Asp Asn Tyr Tyr Ala
        50                  55                  60

Lys Gln Lys Ile Thr Val Gly Leu Thr Val Phe Ala Val Gly Arg Tyr
65                  70                  75                  80

Ile Glu His Tyr Leu Glu Glu Phe Leu Thr Ser Ala Asn Lys His Phe
                85                  90                  95

Met Val Gly His Pro Val Ile Phe Tyr Ile Met Val Asp Asp Val Ser

-continued

```
                100             105             110
Arg Met Pro Leu Ile Glu Leu Gly Pro Leu Arg Ser Phe Lys Val Phe
            115             120             125
Lys Ile Lys Pro Glu Lys Arg Trp Gln Asp Ile Ser Met Met Arg Met
        130             135             140
Lys Thr Ile Gly Glu His Ile Val Ala His Ile Gln His Glu Val Asp
145             150             155             160
Phe Leu Phe Cys Met Asp Val Asp Gln Val Phe Gln Asp Lys Phe Gly
                165             170             175
Val Glu Thr Leu Gly Glu Ser Val Ala Gln Leu Gln Ala Trp Trp Tyr
            180             185             190
Lys Ala Asp Pro Asn Asp Phe Thr Tyr Glu Arg Arg Lys Glu Ser Ala
        195             200             205
Ala Tyr Ile Pro Phe Gly Glu Gly Asp Phe Tyr Tyr Thr Gly Gly Ile
210             215             220
Phe Gly Gly Thr Pro Thr Gln Val Leu Asn Ile Thr Gln Glu Cys Phe
225             230             235             240
Lys Gly Ile Leu Lys Asp Lys Lys Asn Asp Ile Glu Ala Gln Trp His
                245             250             255
Asp Glu Ser His Leu Asn Lys Tyr Phe Leu Leu Asn Lys Pro Thr Lys
            260             265             270
Ile Leu Ser Pro Glu Tyr Cys Trp Asp Tyr His Ile Gly Leu Pro Ser
        275             280             285
Asp Ile Lys Leu Val Lys Met Ser Trp Gln Thr Lys Glu Tyr Asn Val
    290             295             300
Val Arg Asn Asn Val
305

<210> SEQ ID NO 21
<211> LENGTH: 368
<212> TYPE: PRT
<213> ORGANISM: Bos sp.

<400> SEQUENCE: 21

Met Asn Val Lys Gly Lys Val Ile Leu Ser Met Leu Val Val Ser Thr
1               5               10              15
Val Ile Val Val Phe Trp Glu Tyr Ile His Ser Pro Glu Gly Ser Leu
            20              25              30
Phe Trp Ile Asn Pro Ser Arg Asn Pro Glu Val Gly Gly Ser Ser Ile
        35              40              45
Gln Lys Gly Trp Trp Leu Pro Arg Trp Phe Asn Asn Gly Tyr His Glu
    50              55              60
Glu Asp Gly Asp Ile Asn Glu Glu Lys Glu Gln Arg Asn Glu Asp Glu
65              70              75              80
Ser Lys Leu Lys Leu Ser Asp Trp Phe Asn Pro Phe Lys Arg Pro Glu
                85              90              95
Val Val Thr Met Thr Lys Trp Lys Ala Pro Val Val Trp Glu Gly Thr
            100             105             110
Tyr Asn Arg Ala Val Leu Asp Asn Tyr Ala Lys Gln Lys Ile Thr
        115             120             125
Val Gly Leu Thr Val Phe Ala Val Gly Arg Tyr Ile Glu His Tyr Leu
    130             135             140
Glu Glu Phe Leu Thr Ser Ala Asn Lys His Phe Met Val Gly His Pro
145             150             155             160
```

-continued

```
Val Ile Phe Tyr Ile Met Val Asp Asp Val Ser Arg Met Pro Leu Ile
                165                 170                 175

Glu Leu Gly Pro Leu Arg Ser Phe Lys Val Phe Lys Ile Lys Pro Glu
            180                 185                 190

Lys Arg Trp Gln Asp Ile Ser Met Met Arg Met Lys Thr Ile Gly Glu
        195                 200                 205

His Ile Val Ala His Ile Gln His Glu Val Asp Phe Leu Phe Cys Met
    210                 215                 220

Asp Val Asp Gln Val Phe Gln Asp Lys Phe Gly Val Glu Thr Leu Gly
225                 230                 235                 240

Glu Ser Val Ala Gln Leu Gln Ala Trp Trp Tyr Lys Ala Asp Pro Asn
                245                 250                 255

Asp Phe Thr Tyr Glu Arg Arg Lys Glu Ser Ala Ala Tyr Ile Pro Phe
            260                 265                 270

Gly Glu Gly Asp Phe Tyr Tyr His Ala Ala Ile Phe Gly Gly Thr Pro
        275                 280                 285

Thr Gln Val Leu Asn Ile Thr Gln Glu Cys Phe Lys Gly Ile Leu Lys
    290                 295                 300

Asp Lys Lys Asn Asp Ile Glu Ala Gln Trp His Asp Glu Ser His Leu
305                 310                 315                 320

Asn Lys Tyr Phe Leu Leu Asn Lys Pro Thr Lys Ile Leu Ser Pro Glu
                325                 330                 335

Tyr Cys Trp Asp Tyr His Ile Gly Leu Pro Ser Asp Ile Lys Leu Val
            340                 345                 350

Lys Met Ser Trp Gln Thr Lys Glu Tyr Asn Val Val Arg Asn Asn Val
        355                 360                 365
```